United States Patent
Walensky et al.

(10) Patent No.: US 10,259,848 B2
(45) Date of Patent: *Apr. 16, 2019

(54) COMPOSITIONS AND METHODS COMPRISING HYDROCARBON-STAPLED POLYPEPTIDES

(71) Applicant: Dana-Farber Cancer Institute, Inc., Boston, MA (US)

(72) Inventors: Loren D. Walensky, Newton, MA (US); Gregory H. Bird, Pelham, NH (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/146,511

(22) Filed: May 4, 2016

(65) Prior Publication Data

US 2016/0237123 A1   Aug. 18, 2016

Related U.S. Application Data

(63) Continuation of application No. 15/019,558, filed on Feb. 9, 2016, now abandoned, which is a continuation of application No. 12/864,375, filed on Jul. 23, 2010, now Pat. No. 9,290,545, which is a continuation of application No. PCT/US2009/000438, filed on Jan. 23, 2009.

(60) Provisional application No. 61/062,007, filed on Jan. 23, 2008.

(51) Int. Cl.
| | | |
|---|---|---|
| C07K 14/005 | (2006.01) | |
| A61K 38/16 | (2006.01) | |
| A61K 39/145 | (2006.01) | |
| A61K 39/155 | (2006.01) | |
| A61K 39/21 | (2006.01) | |
| C07K 16/10 | (2006.01) | |

(52) U.S. Cl.
CPC .......... *C07K 14/005* (2013.01); *A61K 38/162* (2013.01); *A61K 39/145* (2013.01); *A61K 39/155* (2013.01); *A61K 39/21* (2013.01); *C07K 16/1063* (2013.01); *C07K 2317/76* (2013.01); *C12N 2740/15022* (2013.01); *C12N 2740/15034* (2013.01); *C12N 2740/15071* (2013.01); *C12N 2740/16122* (2013.01); *C12N 2740/16134* (2013.01); *C12N 2740/16171* (2013.01); *C12N 2740/16222* (2013.01); *C12N 2740/16234* (2013.01); *C12N 2740/16271* (2013.01); *C12N 2760/14022* (2013.01); *C12N 2760/14034* (2013.01); *C12N 2760/14071* (2013.01); *C12N 2760/16022* (2013.01); *C12N 2760/16034* (2013.01); *C12N 2760/16071* (2013.01); *C12N 2760/18022* (2013.01); *C12N 2760/18034* (2013.01); *C12N 2760/18071* (2013.01); *C12N 2760/18522* (2013.01); *C12N 2760/18534* (2013.01); *C12N 2760/18571* (2013.01); *C12N 2760/18622* (2013.01); *C12N 2760/18634* (2013.01); *C12N 2760/18671* (2013.01)

(58) Field of Classification Search
None
See application file for complete search history.

(56) References Cited

U.S. PATENT DOCUMENTS

| | | | |
|---|---|---|---|
| 6,271,198 B1 | 8/2001 | Braisted et al. | |
| 9,290,545 B2 | 3/2016 | Walensky | |
| 2005/0250680 A1 | 11/2005 | Walensky et al. | |
| 2006/0241027 A1 | 10/2006 | Hauser et al. | |
| 2006/0247416 A1 | 11/2006 | Delmedico | |
| 2009/0149630 A1 | 6/2009 | Walensky et al. | |
| 2010/0286057 A1* | 11/2010 | Walensky .......... | C07K 14/4747 514/18.9 |

FOREIGN PATENT DOCUMENTS

| | | |
|---|---|---|
| JP | 2001-503064 A | 3/2001 |
| JP | 2003-529319 A | 10/2003 |
| WO | WO-98/20036 A1 | 5/1998 |
| WO | WO-00/40616 A1 | 7/2000 |
| WO | WO-2004-103312 | 12/2004 |
| WO | 2005044839 | 5/2005 |
| WO | WO-2006-121809 | 11/2006 |
| WO | 2009042895 | 4/2009 |
| WO | 2009108261 | 9/2009 |

OTHER PUBLICATIONS

Lambert et al., PNAS, Mar. 1996, 93:2186-2191.*
GenBank Accession No. 1701388A (Apr. 29, 1993) and alignment.*
Venter et al. (Journal of General Virology, 2001, 82:2117-2124.*
Andrews et al., Tetrahedron, 1999, 55:11711-11743.
Dwyer et al., "Design of Helical, Oligomeric HIV-1 Fusion Inhibitor Peptides with Potent Activity Against Enfuvirtide-Resistant Virus," PNAS (2007), 104(31):12772-12777.
Jin et al. "Design of a Peptide Inhibitor that Blocks the Cell Fusion Mediated by Glycoprotein 41 of Human Immunodeficiency Virus Type 1", AIDS Research and Human Retroviruses, vol. 16, No. 17, 2000, pp. 1797-1804.

(Continued)

*Primary Examiner* — Nicole Kinsey White
(74) *Attorney, Agent, or Firm* — Burns & Levinson, LLP; Daniel W. Clarke

(57) ABSTRACT

The invention provides compositions, kits and methods utilizing polypeptides having a viral alpha-helix heptad repeat domain in a stabilized α-helical structure (herein also referred to as SAH). The compositions are useful for treating and/or preventing viral infections. The invention is based, at least in part, on the result provided herein demonstrating that viral hydrocarbon stapled alpha helical peptides display excellent proteolytic, acid, and thermal stability, restore the native alpha-helical structure of the peptide, are highly effective in interfering with the viral fusogenic process, and possess superior pharmacokinetic properties compared to the corresponding unmodified peptides.

15 Claims, 36 Drawing Sheets

Specification includes a Sequence Listing.

(56) References Cited

OTHER PUBLICATIONS

Judice et al. "Inhibition of HIV type 1 infectivity by constrained α-helical peptides: Implications for the viral fusion mechanism", Proc. Natl. Acad, Sci, USA, vol. 94, pp. 13426-13430, Dec. 1997.
Liu et al., "HIV gp41 C-terminal Heptad Repeat Contains Multifunctional Domains," Journal of Biological Chemistry (2007), 282(13):9612-9620.
Long et al., "α-Helix Stabilized Peptides via an all Hydrocarbon-staple Conferring an Improved Inhibitory Activity Against 3'-Processing of HIV-1 Integrase," Proceedings of the 4th International Peptide Symposium (2007), pp. 1-2.
Schafmeister et al., J. Am. Chem. Soc., 2000, 122:5891-5892.
Walensky et al., "Activation of Apoptosis In Vivo by a Hydrocarbon-Stapled BH3 Helix," Science (2004), 305:1466-1470.
Written Opinion of the International Searching Authority in related application PCT/US2009/000438, dated Aug. 5, 2010.
Barouch, D.H., "Challenges in the Development of an HIV-1 Vaccine", Oct. 2008, Nature 455:613-619.
Bird, et al., "Hydrocarbon Double-Stapling Remedies the Proteolytic Instability of a Lengthy Peptide Therapeutic", PNAS, Aug. 10, 2010, vol. 107, No. 32, pp. 14093-14098.
Bird, et al. "Stapled HIV-1 Peptides Recapitulate Antigenic Structures and Engage Broadly Neutralizing Antibodies" Nat Struct Mol Biol. 2014; 21(12): pp. 1058-1067.
Cardoso, et al., Structural Basis of Enhanced Binding of Extended and Helically Constrained Peptide Epitopes of the Broadly Neutralizing HIV-1 Antibody 4E10, J. Mol. Biol. Feb. 2, 2007;365(5):1533-44, Epub Nov. 10, 2006.
Gray, E. S., et al., "4E10-Resistant Variants in a Human Immunodeficiency Virus Type 1 Subtype C-Infected Indivisual with an Anti-Membrane-Proximal External Region-Neutralizing Antibody Response", Mar. 2008, J. Virol. 82 (5):2367-2375.
Ingale, S., et al., "Synthesis and Analysis of the Membrane Proxial External Region Epitopes of HIV-1", 2010, J. Pept. Sci. 16:716-722.
Johnston, M.I., et al., "An HIV Vaccine-Challenges and Prospects", 2008, The New England Journal of Medicine 359 (9):888-890.

Joyce, et al., "Enhancement of Alpha-Helicity in the HIV-1 Inhibitory Peptide DP178 Leads to an Increased Affinity for Human Monoclonal Antibody 2F5 But Does Not Elicit Neutralizing Responses in Vitro", Implications for Vaccine Design, J. Biol. Chem. Nov. 29, 2002;277(48):45811-20.
Kim, M., et al., Immunogenicity of Membrane-Bound HIV-1 gp41 Membrane-Proximal External Region (MPER) Segments is Dominated by Residue Accessibility and Modulated by Stereochemistry, J. Biol. Chem. 288 (44):31888-31901, 2013.
Lewis, G. K., et al., "Antibody Persistence and T-Cell Balance: Two Key Factors Confronting HIV Vaccine Development", Nov. 2014, Proc. Natl. Acad. Sci. 111(44):15614-15621.
Nelson, et al., "An Affinity-Enhanced Neutralizing Antibody Against the Membrane-Proximal External Region of Human Immunodeficiency Virus Type 1 GP41 Recognizes an Epitope Between Those of 2F5 and 4E10", J. Virol. Apr. 2007;81 (8):4033-43.
Noah, et al., "The Membrane Proximal External Region of the HIV-1 Envelope Glycoprotein GP41 Contributes to the Stabilization of the Six-Helix Bundle Formed with a Matching N' Peptide", Biochemistry, vol. 47, No. 26, Jul. 2008, pp. 6782-6792.
Penn-Nicholson, Adam, et al., "Assessment of Antibody Responses Agains GP41 in HIV-1-Infected Patients Using Soluble GP41 Fusion Proteins and Peptides Derived from M Group Consensus Envelope", Virology, Mar. 15, 2008, 372(2), pp. 442-456.
Sawyer, AILERON Therapeutics., Chem. Biol. & Drug Des. Dec. 18, 2008;73(1):3-6.
Sen J., et al., "Alaine Scanning Mutagenesis of HIV-1 GP41 Heptad Repeat 1: Insight into the GP120-GP41 Interaction", Biochem. 2010 49:5057-5056.
Walensky, et al. "Hydrocarbon-Stapled Peptides: Principles, Practice, and Progress", Journal of Medicinal Chemistry, 2014, 57, pp. 6275-6288.
Walker, B.D., et al., "Toward an AIDS Vaccine", May 2008, Science 320:760-764.
Wang, et al., "Inhibition of HIV-1 Fusion by Hydrogen-Bond-Surrogate-Based a Helics", Angew, Chem., Int. Ed., vol. 47, pp. 1879-1882 (2008).

\* cited by examiner

FIGURE 1

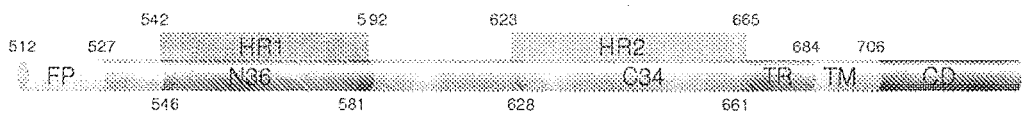

FIGURE 2A (SEQ ID NO: 49)

MRVKEKYQHLWRWGWRWGTMLLGMLMICSATEKLWVTVYYGVPVWKEATTTLFCASD
AKAYDTEVHNVWATHACVPTDPNPQEVVLVNVTENFNMWKNDMVEQMHEDIISLWDQ
SLKPCVKLTPLCVSLKCTDLKNDTNTNSSSGRMIMEKGEIKNCSFNISTSIRGKVQK
EYAFFYKLDIIPIDNDTTSYKLTSCNTSVITQACPKVSFEPIPIHYCAPAGFAILKC
NNKTFNGTGPCTNVSTVQCTHGIRPVVSTQLLLNGSLAEEEVVIRSVNFTDNAKTII
VQLNTSVEINCTRPNNNTRKRIRIQRGPGRAFVTIGKIGNMRQAHCNISRAKWNNTL
KQIASKLREQFGNNKTIIFKQSSGGDPEIVTHSFNCGGEFFYCNSTQLFNSTWFNST
WSTEGSNNTEGSDTITLPCRIKQIINMWQKVGKAMYAPPISGQIRCSSNITGLLLTR
DGGNSNNESEIFRPGGGDMRDNWRSELYKYKVVKIEPLGVAPTKAKRRVVQREKRAV
GIGALFLGFLGAAGSTMGAASMTLTVQA<u>RQLLSGIVQQQNNLLRAIEAQQHLLQLTV</u>
<u>WGIKQLQARILAVERYLKDQQL</u>LGIWGCSGKLICTTAVPWNASWSNKSLE*QIWNHTT*
*WMEWDREINNYTSLIHSLIEESQNQQEKNEQELLELDKWASLWNWF*NITNWLWYIKL
FIMIVGGLVGLRIVFAVLSIVNRVRQGYSPLSFQTHLPTPRGPDRPEGIEEEGGERD
RDRSIRLVNGSLALIWDDLRSLCLFSYHRLRDLLLIVTRIVELLGRRGWEALKYWWN
LLQYWSQELKNSAVSLLNATAIAVAEGTDRVIEVVQGACRAIRHIPRRIRQGLERIL
L

FIGURE 2B (SEQ ID NO: 50)

MRATEIRKNYQHLWKGGTLLLGMLMICSAAEQLWVTVYYGVPVWKEATTTLFCASDA
KAYDTEVHNVWATHACVPTDPNPQEVKLENVTENFNMWKNNMVEQMHEDIISLWDQS
LKPCVKLTPLCVTLNCTDLRNATNTTSSSWETMEKGEIKNCSFNITTSIRDKVQKEY
ALFYNLDVVPIDNASYRLISCNTSVITQACPKVSFEPIPIHYCAPAGFAILKCNDKK
FNGTGPCTNVSTVQCTHGIRPVVSTQLLLNGSLAEEEIVIRSENFTNNAKTIIVQLN
ESVVINCTRPNNNTRKSINIGPGRALYTTGEIIGDIRQAHCNLSKTQWENTLEQIAI
KLKEQFGNNKTIIFNPSSGGDPEIVTHSFNCGGEFFYCNSTQLFTWNDTRKLNNTGR
NITLPCRIKQIINMWQEVGKAMYAPPIRGQIRCSSNITGLLLTRDGGKDTNGTEIFR
PGGGDMRDNWRSELYKYKVVKIEPLGVAPTKAKRRVVQREKRAVGLGALFLGFLGAA
GSTMGAASITLTVQA<u>RQLLSGIVQQQNNLLRAIEAQQHLLQLTVWGIKQLQARVLAV</u>
<u>ERYLRDQQL</u>LGIWGCSGKLICTTTVPWNTSWSNKSLN*EIWDNMTWMKWEREIDNYTH*
*IIYSLIEQSQNQQEKNEQELLALDKWASLWNWF*DITKWLWYIKIFIMIVGGLIGLRI
VFVVLSIVNRVRQGYSPLSFQTHLPAQRGPDRPDGIEEEGGERDRSGPLVDGFLA
IIWVDLRSLCLFSYHRLRDLLLIVTRIVELLGRRGWGVLKYWWNLLQYWIQELKNSA
VSLLNATAIAVAEGTDRVIEILQRAFRAVLHIPVRIRQGLERALL

FIGURE 3

Heptad-repeat domain 1 (HR1)

| Virus | Sequence |
|---|---|
| HIV gp41 | 542 SQLLSGIVQQQNNLLRAIEAQQHLLQLTVWGIKQLQARILAVERYLQQQL 592 |
| SARS coronavirus spike protein | 896 NVLYENQKQIANQFNKAISQIQESLTTTSTALGKLQDVVNQNAQALNTLVKQLSSNFGAISSVLNDILSRLDKVEAE 972 |
| Ebolavirus spike protein | 546 DGLICGLRQLANETTQALQLFLRATTELRTFSILNRKAIDFLL 594 |
| RSV F protein | 150 SGIAVSKVLHLEGEVNKIKNALLSTNKAVVSLSNGVSVLTSKVLDLKNYIDKQLLPI 206 |
| Human parainfluenza virus | 119 ALGVATSAQITAAVALVEAKQARSDIEKLKEAIRDTNKAVQSVQSSIGNLIVAIKSVQDYVNKEI 183 |
| T-cell leukemia virus | 338 MSLASQKSLLHEVDKDISQLTQAIVKNHKNLLKIAQYAAQNRRGLDLLFW 387 |
| Marburg virus | 553 NNLVCRIRRLANQTAKSLELLLRVVTTEERTFSLINRHAIDFL 594 |

Heptad-repeat domain 2 (HR2)

| Virus | Sequence |
|---|---|
| HIV gp41 | 623 WNNMTWMEWEREIDNYTSLIYTLLEETSQNQQEKNEQELLELDK 665 |
| SARS coronavirus spike protein | 1142 TSPDVDFGDISGINASVVNIQKEIDRLNEVAKNLNESLIDLQELGKY 1188 |
| Ebolavirus spike protein | 614 IMTKNITDKIDQIIHDFVDKTLPD 637 |
| RSV F protein | 473 PIINYYDPLVFPSDEFDASISQVNEKINQSLAFIRRSDELLANWTGKSTTNIM 526 |
| Human parainfluenza virus | 438 YTENDITTLMNSVALDPIDISIELNKAKSDLEESKEWIRRSNQKLDSIGNWHQSSTT 493 |
| T-cell leukemia virus | 400 CCFLNITNSHVSILQERPPLENRVLTGWGL 429 |
| Marburg virus | 613 IEPLSRNISEQIDQIKKDEQ 632 |

(SEQ ID NOS 14, 7, 9, 11, 51-54, 8, 10, 12 and 55-57, respectively, in order of appearance)

FIGURE 5A

```
YTS
YTSL
YTSLI
YTSLIH
YTSLIHS
YTSLIHSL
YTSLIHSLI
YTSLIHSLIE
YTSLIHSLIEE
YTSLIHSLIEES
YTSLIHSLIEESQ
YTSLIHSLIEESQN
YTSLIHSLIEESQNQ
YTSLIHSLIEESQNQQ
YTSLIHSLIEESQNQQE
YTSLIHSLIEESQNQQEK
YTSLIHSLIEESQNQQEKN
YTSLIHSLIEESQNQQEKNE
YTSLIHSLIEESQNQQEKNEQ
YTSLIHSLIEESQNQQEKNEQE
YTSLIHSLIEESQNQQEKNEQEL
YTSLIHSLIEESQNQQEKNEQELL
YTSLIHSLIEESQNQQEKNEQELLE
YTSLIHSLIEESQNQQEKNEQELLEL
YTSLIHSLIEESQNQQEKNEQELLELD
YTSLIHSLIEESQNQQEKNEQELLELDK
YTSLIHSLIEESQNQQEKNEQELLELDKW
YTSLIHSLIEESQNQQEKNEQELLELDKWA
YTSLIHSLIEESQNQQEKNEQELLELDKWAS
YTSLIHSLIEESQNQQEKNEQELLELDKWASL
YTSLIHSLIEESQNQQEKNEQELLELDKWASLW
YTSLIHSLIEESQNQQEKNEQELLELDKWASLWN
YTSLIHSLIEESQNQQEKNEQELLELDKWASLWNW
YTSLIHSLIEESQNQQEKNEQELLELDKWASLWNWF
```

(Figure discloses residues 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34 and 1-35 of SEQ ID NO: 1 and SEQ ID NO: 1, respectively, in order of appearance)

FIGURE 5A (continued)

```
MTW
MTWM
MTWME
MTWMEW
MTWMEWD
MTWMEWDR
MTWMEWDRE
MTWMEWDREI
MTWMEWDREIN
MTWMEWDREINN
MTWMEWDREINNY
MTWMEWDREINNYT
MTWMEWDREINNYTS
MTWMEWDREINNYTSL
MTWMEWDREINNYTSLI
MTWMEWDREINNYTSLIH
MTWMEWDREINNYTSLIHS
MTWMEWDREINNYTSLIHSL
MTWMEWDREINNYTSLIHSLI
MTWMEWDREINNYTSLIHSLIE
MTWMEWDREINNYTSLIHSLIEE
MTWMEWDREINNYTSLIHSLIEES
MTWMEWDREINNYTSLIHSLIEESQ
MTWMEWDREINNYTSLIHSLIEESQN
MTWMEWDREINNYTSLIHSLIEESQNQ
MTWMEWDREINNYTSLIHSLIEESQNQQ
MTWMEWDREINNYTSLIHSLIEESQNQQE
MTWMEWDREINNYTSLIHSLIEESQNQQEK
MTWMEWDREINNYTSLIHSLIEESQNQQEKN
MTWMEWDREINNYTSLIHSLIEESQNQQEKNE
MTWMEWDREINNYTSLIHSLIEESQNQQEKNEQ
MTWMEWDREINNYTSLIHSLIEESQNQQEKNEQE
MTWMEWDREINNYTSLIHSLIEESQNQQEKNEQEL
MTWMEWDREINNYTSLIHSLIEESQNQQEKNEQELL
```

(Figure discloses residues 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35 and 1-36 of SEQ ID NO: 13, respectively, in order of appearance)

FIGURE 5A (continued)

```
YTH
YTHI
YTHIY
YTHIIY
YTHIIYS
YTHIIYSL
YTHIIYSLI
YTHIIYSLIE
YTHIIYSLIEQ
YTHIIYSLIEQS
YTHIIYSLIEQSQ
YTHIIYSLIEQSQN
YTHIIYSLIEQSQNQ
YTHIIYSLIEQSQNQQ
YTHIIYSLIEQSQNQQE
YTHIIYSLIEQSQNQQEK
YTHIIYSLIEQSQNQQEKN
YTHIIYSLIEQSQNQQEKNE
YTHIIYSLIEQSQNQQEKNEQ
YTHIIYSLIEQSQNQQEKNEQE
YTHIIYSLIEQSQNQQEKNEQEL
YTHIIYSLIEQSQNQQEKNEQELL
YTHIIYSLIEQSQNQQEKNEQELLA
YTHIIYSLIEQSQNQQEKNEQELLAL
YTHIIYSLIEQSQNQQEKNEQELLALD
YTHIIYSLIEQSQNQQEKNEQELLALDK
YTHIIYSLIEQSQNQQEKNEQELLALDKW
YTHIIYSLIEQSQNQQEKNEQELLALDKWA
YTHIIYSLIEQSQNQQEKNEQELLALDKWAS
YTHIIYSLIEQSQNQQEKNEQELLALDKWASL
YTHIIYSLIEQSQNQQEKNEQELLALDKWASLW
YTHIIYSLIEQSQNQQEKNEQELLALDKWASLWN
YTHIIYSLIEQSQNQQEKNEQELLALDKWASLWNW
YTHIIYSLIEQSQNQQEKNEQELLALDKWASLWNWF
```

(Figure discloses residues 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34 and 1-35 of SEQ ID NO: 58 and SEQ ID NO: 58, respectively, in order of appearance)

FIGURE 5A (continued)

```
MTM
MTMK
MTMKW
MTMKWE
MTMKWER
MTMKWERE
MTMKWEREI
MTMKWEREID
MTMKWEREIDN
MTMKWEREIDNY
MTMKWEREIDNYT
MTMKWEREIDNYTH
MTMKWEREIDNYTHI
MTMKWEREIDNYTHII
MTMKWEREIDNYTHIIY
MTMKWEREIDNYTHIIYS
MTMKWEREIDNYTHIIYSL
MTMKWEREIDNYTHIIYSLI
MTMKWEREIDNYTHIIYSLIE
MTMKWEREIDNYTHIIYSLIEQ
MTMKWEREIDNYTHIIYSLIEQS
MTMKWEREIDNYTHIIYSLIEQSQ
MTMKWEREIDNYTHIIYSLIEQSQN
MTMKWEREIDNYTHIIYSLIEQSQNQ
MTMKWEREIDNYTHIIYSLIEQSQNQQ
MTMKWEREIDNYTHIIYSLIEQSQNQQE
MTMKWEREIDNYTHIIYSLIEQSQNQQEK
MTMKWEREIDNYTHIIYSLIEQSQNQQEKN
MTMKWEREIDNYTHIIYSLIEQSQNQQEKNE
MTMKWEREIDNYTHIIYSLIEQSQNQQEKNEQ
MTMKWEREIDNYTHIIYSLIEQSQNQQEKNEQE
MTMKWEREIDNYTHIIYSLIEQSQNQQEKNEQEL
MTMKWEREIDNYTHIIYSLIEQSQNQQEKNEQELL
MTMKWEREIDNYTHIIYSLIEQSQNQQEKNEQELLA
```

(Figure discloses residues 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34 and 1-35 of SEQ ID NO: 59 and SEQ ID NO: 59, respectively, in order of appearance)

FIGURE 5B

```
                              NWF
                             WNWF
                            LWNWF
                           SLWNWF
                          ASLWNWF
                         WASLWNWF
                        KWASLWNWF
                       DKWASLWNWF
                      LDKWASLWNWF
                     ELDKWASLWNWF
                    LELDKWASLWNWF
                   LLELDKWASLWNWF
                  ELLELDKWASLWNWF
                 QELLELDKWASLWNWF
                EQELLELDKWASLWNWF
               NEQELLELDKWASLWNWF
              KNEQELLELDKWASLWNWF
             EKNEQELLELDKWASLWNWF
            QEKNEQELLELDKWASLWNWF
           QQEKNEQELLELDKWASLWNWF
          NQQEKNEQELLELDKWASLWNWF
         QNQQEKNEQELLELDKWASLWNWF
        SQNQQEKNEQELLELDKWASLWNWF
       ESQNQQEKNEQELLELDKWASLWNWF
      EESQNQQEKNEQELLELDKWASLWNWF
     IEESQNQQEKNEQELLELDKWASLWNWF
    LIEESQNQQEKNEQELLELDKWASLWNWF
   SLIEESQNQQEKNEQELLELDKWASLWNWF
  HSLIEESQNQQEKNEQELLELDKWASLWNWF
 IHSLIEESQNQQEKNEQELLELDKWASLWNWF
LIHSLIEESQNQQEKNEQELLELDKWASLWNWF
SLIHSLIEESQNQQEKNEQELLELDKWASLWNWF
TSLIHSLIEESQNQQEKNEQELLELDKWASLWNWF
YTSLIHSLIEESQNQQEKNEQELLELDKWASLWNWF
```

(Figure discloses residues 33-36, 32-36, 31-36, 30-36, 29-36, 28-36, 27-36, 26-36, 25-36, 24-36, 23-36, 22-36, 21-36, 20-36, 19-36, 18-36, 17-36, 16-36, 15-36, 14-36, 13-36, 12-36, 11-36, 10-36, 9-36, 8-36, 7-36, 6-36, 5-36, 4-36, 3-36 and 2-36 of SEQ ID NO: 1 and SEQ ID NO: 1, respectively, in order of appearance)

FIGURE 5B (continued)

```
                              LLE
                             ELLE
                            QELLE
                           EQELLE
                          NEQELLE
                         KNEQELLE
                        EKNEQELLE
                       QEKNEQELLE
                      QQEKNEQELLE
                     NQQEKNEQELLE
                    QNQQEKNEQELLE
                   SQNQQEKNEQELLE
                  ESQNQQEKNEQELLE
                 EESQNQQEKNEQELLE
                IEESQNQQEKNEQELLE
               LIEESQNQQEKNEQELLE
              SLIEESQNQQEKNEQELLE
             HSLIEESQNQQEKNEQELLE
            IHSLIEESQNQQEKNEQELLE
           LIHSLIEESQNQQEKNEQELLE
          SLIHSLIEESQNQQEKNEQELLE
         TSLIHSLIEESQNQQEKNEQELLE
        YTSLIHSLIEESQNQQEKNEQELLE
       NYTSLIHSLIEESQNQQEKNEQELLE
      NNYTSLIHSLIEESQNQQEKNEQELLE
     INNYTSLIHSLIEESQNQQEKNEQELLE
    EINNYTSLIHSLIEESQNQQEKNEQELLE
   REINNYTSLIHSLIEESQNQQEKNEQELLE
  DREINNYTSLIHSLIEESQNQQEKNEQELLE
 WDREINNYTSLIHSLIEESQNQQEKNEQELLE
EWDREINNYTSLIHSLIEESQNQQEKNEQELLE
MEWDREINNYTSLIHSLIEESQNQQEKNEQELLE
WMEWDREINNYTSLIHSLIEESQNQQEKNEQELLE
TWMEWDREINNYTSLIHSLIEESQNQQEKNEQELLE
MTWMEWDREINNYTSLIHSLIEESQNQQEKNEQELLE
```

(Figure discloses residues 34-37, 33-37, 32-37, 31-37, 30-37, 29-37, 28-37, 27-37, 26-37, 25-37, 24-37, 23-37, 22-37, 21-37, 20-37, 19-37, 18-37, 17-37, 16-37, 15-37, 14-37, 13-37, 12-37, 11-37, 10-37, 9-37, 8-37, 7-37, 6-37, 5-37, 4-37, 3-37 and 2-37 of SEQ ID NO: 13 and SEQ ID NO: 13, respectively, in order of appearance)

FIGURE 5B (continued)

```
                              NWF
                             WNWF
                            LWNWF
                           SLWNWF
                          ASLWNWF
                         WASLWNWF
                        KWASLWNWF
                       DKWASLWNWF
                      LDKWASLWNWF
                     ALDKWASLWNWF
                    LALDKWASLWNWF
                   LLALDKWASLWNWF
                  ELLALDKWASLWNWF
                 QELLALDKWASLWNWF
                EQELLALDKWASLWNWF
               NEQELLALDKWASLWNWF
              KNEQELLALDKWASLWNWF
             EKNEQELLALDKWASLWNWF
            QEKNEQELLALDKWASLWNWF
           QQEKNEQELLALDKWASLWNWF
          NQQEKNEQELLALDKWASLWNWF
         QNQQEKNEQELLALDKWASLWNWF
        SQNQQEKNEQELLALDKWASLWNWF
       QSQNQQEKNEQELLALDKWASLWNWF
      EQSQNQQEKNEQELLALDKWASLWNWF
     IEQSQNQQEKNEQELLALDKWASLWNWF
    LIEQSQNQQEKNEQELLALDKWASLWNWF
   SLIEQSQNQQEKNEQELLALDKWASLWNWF
  YSLIEQSQNQQEKNEQELLALDKWASLWNWF
 TYSLIEQSQNQQEKNEQELLALDKWASLWNWF
ITYSLIEQSQNQQEKNEQELLALDKWASLWNWF
HITYSLIEQSQNQQEKNEQELLALDKWASLWNWF
THITYSLIEQSQNQQEKNEQELLALDKWASLWNWF
YTHITYSLIEQSQNQQEKNEQELLALDKWASLWNWF
```

(Figure discloses residues 33-36, 32-36, 31-36, 30-36, 29-36, 28-36, 27-36, 26-36, 25-36, 24-36, 23-36, 22-36, 21-36, 20-36, 19-36, 18-36, 17-36, 16-36, 15-36, 14-36, 13-36, 12-36, 11-36, 10-36, 9-36, 8-36, 7-36, 6-36, 5-36, 4-36, 3-36 and 2-36 of SEQ ID NO: 58 and SEQ ID NO: 58, respectively, in order of appearance)

FIGURE 5B (continued)

```
                            LLA
                           ELLA
                          QELLA
                         EQELLA
                        NEQELLA
                       KNEQELLA
                      EKNEQELLA
                     QEKNEQELLA
                    QQEKNEQELLA
                   NQQEKNEQELLA
                  QNQQEKNEQELLA
                 SQNQQEKNEQELLA
                QSQNQQEKNEQELLA
               EQSQNQQEKNEQELLA
              IEQSQNQQEKNEQELLA
             LIEQSQNQQEKNEQELLA
            SLIEQSQNQQEKNEQELLA
           YSLIEQSQNQQEKNEQELLA
          IYSLIEQSQNQQEKNEQELLA
         IIYSLIEQSQNQQEKNEQELLA
        HIIYSLIEQSQNQQEKNEQELLA
       THIIYSLIEQSQNQQEKNEQELLA
      YTHIIYSLIEQSQNQQEKNEQELLA
     NYTHIIYSLIEQSQNQQEKNEQELLA
    DNYTHIIYSLIEQSQNQQEKNEQELLA
   IDNYTHIIYSLIEQSQNQQEKNEQELLA
  EIDNYTHIIYSLIEQSQNQQEKNEQELLA
 REIDNYTHIIYSLIEQSQNQQEKNEQELLA
EREIDNYTHIIYSLIEQSQNQQEKNEQELLA
WEREIDNYTHIIYSLIEQSQNQQEKNEQELLA
KWEREIDNYTHIIYSLIEQSQNQQEKNEQELLA
MKWEREIDNYTHIIYSLIEQSQNQQEKNEQELLA
TMKWEREIDNYTHIIYSLIEQSQNQQEKNEQELLA
MTMKWEREIDNYTHIIYSLIEQSQNQQEKNEQELLA
```

(Figure discloses residues 33-36, 32-36, 31-36, 30-36, 29-36, 28-36, 27-36, 26-36, 25-36, 24-36, 23-36, 22-36, 21-36, 20-36, 19-36, 18-36, 17-36, 16-36, 15-36, 14-36, 13-36, 12-36, 11-36, 10-36, 9-36, 8-36, 7-36, 6-36, 5-36, 4-36, 3-36 and 2-36 of SEQ ID NO: 59 and SEQ ID NO: 59, respectively, in order of appearance)

FIGURE 6

```
              SQNQQEKNEQELLE
              SQNQQEKNEQELLEL
             ESQNQQEKNEQELLEL
             ESQNQQEKNEQELLELD
            EESQNQQEKNEQELLELD
            EESQNQQEKNEQELLELDK
           IEESQNQQEKNEQELLELDK
           IEESQNQQEKNEQELLELDKW
          LIEESQNQQEKNEQELLELDKW
          LIEESQNQQEKNEQELLELDKWA
         SLIEESQNQQEKNEQELLELDKWA
         SLIEESQNQQEKNEQELLELDKWAS
        RSLIEESQNQQEKNEQELLELDKWAS
        RSLIEESQNQQEKNEQELLELDKWASL
       IRSLIEESQNQQEKNEQELLELDKWASL
       IRSLIEESQNQQEKNEQELLELDKWASLW
      LIRSLIEESQNQQEKNEQELLELDKWASLW
      LIRSLIEESQNQQEKNEQELLELDKWASLWN
     SLIRSLIEESQNQQEKNEQELLELDKWASLWN
     SLIRSLIEESQNQQEKNEQELLELDKWASLWNW
    TSLIRSLIEESQNQQEKNEQELLELDKWASLWNW
    TSLIRSLIEESQNQQEKNEQELLELDKWASLWNWF
   YTSLIRSLIEESQNQQEKNEQELLELDKWASLWNWF
```

(Figure discloses residues 12-25, 12-26, 11-26, 11-27, 10-27, 10-28, 9-28, 9-29, 8-29, 8-30, 7-30, 7-31, 6-31, 6-32, 5-32, 5-33, 4-33, 4-34, 3-34, 3-35, 2-35 and 2-36 of SEQ ID NO: 1 and SEQ ID NO: 1, respectively, in order of appearance)

FIGURE 6 (continued)

```
           NYTSLIRSLIEESQN
           NYTSLIRSLIEESQNQ
          NNYTSLIRSLIEESQNQ
          NNYTSLIRSLIEESQNQQ
         INNYTSLIRSLIEESQNQQ
         INNYTSLIRSLIEESQNQQE
        EINNYTSLIRSLIEESQNQQE
        EINNYTSLIRSLIEESQNQQEK
       REINNYTSLIRSLIEESQNQQEK
       REINNYTSLIRSLIEESQNQQEKN
      DREINNYTSLIRSLIEESQNQQEKN
      DREINNYTSLIRSLIEESQNQQEKNE
     WDREINNYTSLIRSLIEESQNQQEKNE
     WDREINNYTSLIRSLIEESQNQQEKNEQ
    SWDREINNYTSLIRSLIEESQNQQEKNEQ
    SWDREINNYTSLIRSLIEESQNQQEKNEQE
   MSWDREINNYTSLIRSLIEESQNQQEKNEQE
   MSWDREINNYTSLIRSLIEESQNQQEKNEQEL
  WMSWDREINNYTSLIRSLIEESQNQQEKNEQEL
  WMSWDREINNYTSLIRSLIEESQNQQEKNEQELL
 TWMSWDREINNYTSLIRSLIEESQNQQEKNEQELL
 TWMSWDREINNYTSLIRSLIEESQNQQEKNEQELLE
KTWMSWDREINNYTSLIRSLIEESQNQQEKNEQELLE
```

(Figure discloses residues 12-26, 12-27, 11-27, 11-28, 10-28, 10-29, 9-29, 9-30, 8-30, 8-31, 7-31, 7-32, 6-32, 6-33, 5-33, 5-34, 4-34, 4-35, 3-35, 3-36, 2-36 and 2-37 of SEQ ID NO: 13 and SEQ ID NO: 13, respectively, in order of appearance)

FIGURE 6 (continued)

```
             SQNQQEKNEQELLA
             SQNQQEKNEQELLAL
            QSQNQQEKNEQELLAL
            QSQNQQEKNEQELLALD
           EQSQNQQEKNEQELLALD
           EQSQNQQEKNEQELLALDK
          IEQSQNQQEKNEQELLALDK
          IEQSQNQQEKNEQELLALDKW
         LIEQSQNQQEKNEQELLALDKW
         LIEQSQNQQEKNEQELLALDKWA
        SLIEQSQNQQEKNEQELLALDKWA
        SLIEQSQNQQEKNEQELLALDKWAS
       YSLIEQSQNQQEKNEQELLALDKWAS
       YSLIEQSQNQQEKNEQELLALDKWASL
      IYSLIEQSQNQQEKNEQELLALDKWASL
      IYSLIEQSQNQQEKNEQELLALDKWASLW
     IIYSLIEQSQNQQEKNEQELLALDKWASLW
     IIYSLIEQSQNQQEKNEQELLALDKWASLWN
    HIIYSLIEQSQNQQEKNEQELLALDKWASLWN
    HIIYSLIEQSQNQQEKNEQELLALDKWASLWNW
   THIIYSLIEQSQNQQEKNEQELLALDKWASLWNW
   THIIYSLIEQSQNQQEKNEQELLALDKWASLWNWF
  YTHIIYSLIEQSQNQQEKNEQELLALDKWASLWNWF
```

(Figure discloses residues 12-25, 12-26, 11-26, 11-27, 10-27, 10-28, 9-28, 9-29, 8-29, 8-30, 7-30, 7-31, 6-31, 6-32, 5-32, 5-33, 4-33, 4-34, 3-34, 3-35, 2-35 and 2-36 of SEQ ID NO: 58 and SEQ ID NO: 58, respectively, in order of appearance)

FIGURE 6 (continued)

```
          NYTHIIYSLIEQSQN
          NYTHIIYSLIEQSQNQ
         DNYTHIIYSLIEQSQNQ
         DNYTHIIYSLIEQSQNQQ
        IDNYTHIIYSLIEQSQNQQ
        IDNYTHIIYSLIEQSQNQQE
       EIDNYTHIIYSLIEQSQNQQE
       EIDNYTHIIYSLIEQSQNQQEKN
      REIDNYTHIIYSLIEQSQNQQEKN
      REIDNYTHIIYSLIEQSQNQQEKNE
     EREIDNYTHIIYSLIEQSQNQQEKNE
     EREIDNYTHIIYSLIEQSQNQQEKNEQ
    WEREIDNYTHIIYSLIEQSQNQQEKNEQ
    WEREIDNYTHIIYSLIEQSQNQQEKNEQE
   KWEREIDNYTHIIYSLIEQSQNQQEKNEQE
   KWEREIDNYTHIIYSLIEQSQNQQEKNEQEL
  MKWEREIDNYTHIIYSLIEQSQNQQEKNEQEL
  MKWEREIDNYTHIIYSLIEQSQNQQEKNEQELL
 TMKWEREIDNYTHIIYSLIEQSQNQQEKNEQELL
 TMKWEREIDNYTHIIYSLIEQSQNQQEKNEQELLA
MTMKWEREIDNYTHIIYSLIEQSQNQQEKNEQELLA
```

(Figure discloses residues 11-25, 11-26, 10-26, 10-27, 9-27, 9-28, 8-28, 8-30, 7-30, 7-31, 6-31, 6-32, 5-32, 5-33, 4-33, 4-34, 3-34, 3-35, 2-35 and 2-36 of SEQ ID NO: 59 and SEQ ID NO: 59, respectively, in order of appearance)

FIGURE 7 gp41(626-645)        BTWBEWDREINNYTSLIHSL      (SEQ ID NO: 60)

SAH-gp41(626-645)(A) BTWBEWDREINNYTSLIHSL      (SEQ ID NO: 61)

FIGURE 8

```
            WQEWERKVDFLEENITALLEEAQIQQEK                      SIV

HX strain of gp160:
                  YTSLIHSLIEESQNQQEKNEQELLELDKWASLWNWF  HIV(T20)
      MTWMEWDREINNYTSLIHSLIEESQNQQEKNEQELLE
HIV(T649)

YU2 strain of gp160:
                  YTHIIYSLIEQSQNQQEKNEQELLALDKWASLWNWF  HIV(T20)
      MTMKWEREIDNYTHIIYSLIEQSQNQQEKNEQELLA              HIV(T649)

Chimera    WQEWEQKITALLEQAQIQQEKNEYELQKLDKWASLWEWF  (T1249)
T20        --------I--LLE---Q-QQEKNE-EL---LDKWASLW-WF
T649       W-EW---I----------------------------------
SIV        WQEWE-K-----------------------------------
```

(SEQ ID NOS 62, 1, 13, 57-58, 19 and 63-65, respectively, in order of appearance)

FIGURE 9A (heptad repeat domain)

```
    ---abcdefgabcdefgabcdefgabcdefgabcdefga
```

FIGURE 9B HIV gp41 (626-663) (SEQ ID NO: 66)

```
    MTWMEWDREINNYTSLIHSLIEESQNQQEKNEQELLEL
```

FIGURE 9C (heptad position a, d) (SEQ ID NO: 44)

```
    --W--W---I---Y---I---L---S--Q---N--E---L
```

(residues as per Dwyer et al. PNAS, 104: 12772, 2007)

FIGURE 9D (SEQ ID NO: 45)

```
    -TW---WDR-I---Y----I---LI----Q--QEK-E---L-EL
```

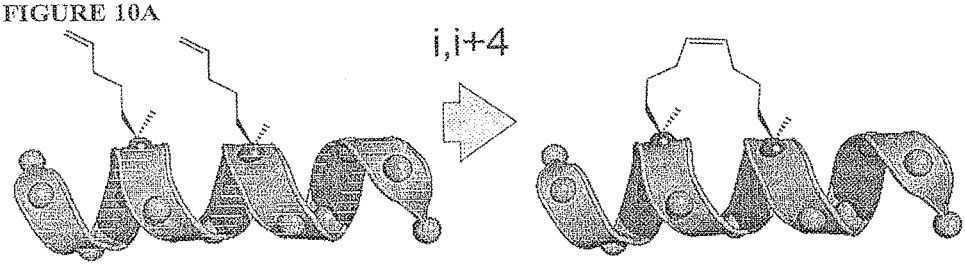
FIGURE 10A    i,i+4
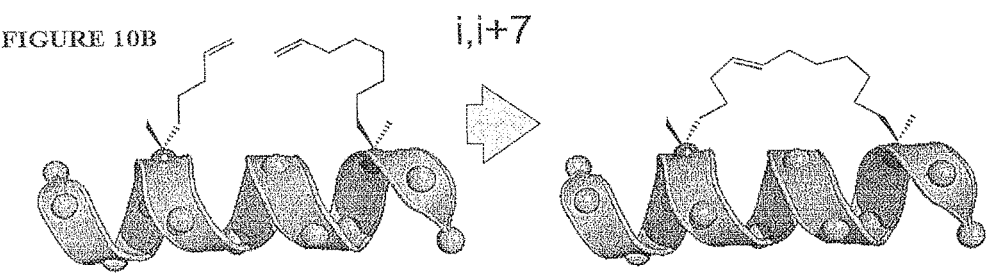
FIGURE 10B    i,i+7

FIGURE 10C
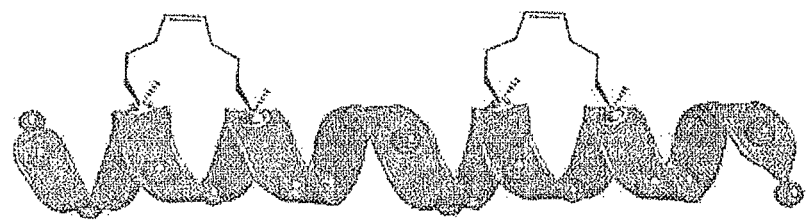
i,i+4 and i,i+4
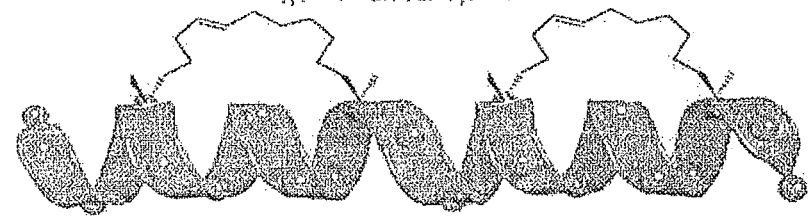
i,i+7 and i,i+7
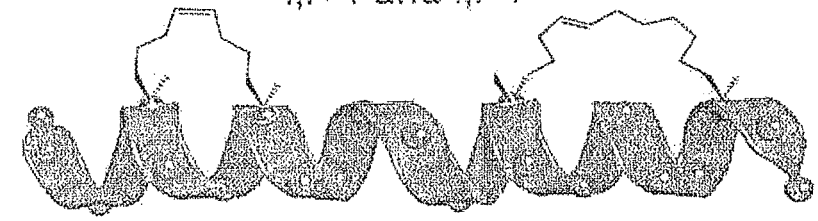
i,i+4 and i,i+7
FIGURE 10D    i,i+4 and i,i+4 and i,i+4
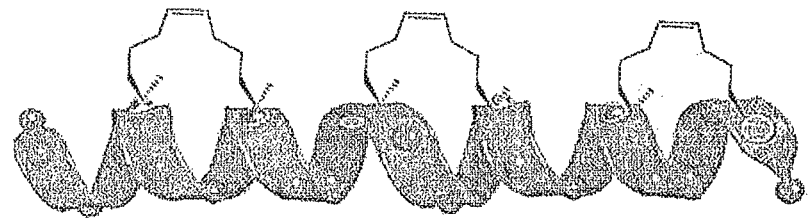

(SEQ ID NOS 67-71, 1 and 72-79, respectively, in order of appearance)

FIGURE 12

```
       A     C      I      E       J        G
     ┌──┐ ┌──┐  ┌──┐   ┌──┐   ┌──┐     ┌──┐
626 BTWBEWDREINNYTSLIHSLIEESQNQQEKNEQELLELDKWASLWNWE 673
        └──┘ └──┘  └──┘    └──┘└──┘    └──┘
         B    D     F       K     H
```

| | |
|---|---|
| BTWBEWDREINNYTSLIHSLIEESQNQQEKNEQELLE | gp41$_{(626\text{-}662)}$ |
| BTWXEWDXEINNYTSLIHSLIEESQNQXEKNXQELLE | SAH-gp41$_{(626\text{-}662)}$(A, F) |
| BTWBEWXREIXNYTSLIHSLIEESQNQXEKNXQELLE | SAH-gp41$_{(626\text{-}662)}$(B, F) |
| BTWBEWDREIXNYTXLIHSLIEESQNQXEKNXQELLE | SAH-gp41$_{(626\text{-}662)}$(C, F) |
| BTWBEWDREINNYTXLIHXLIEESQNQXEKNXQELLE | SAH-gp41$_{(626\text{-}662)}$(D, F) |
| BTWXEWDXEINNYTSLIHSLIXESQXQQEKNEQELLE | SAH-gp41$_{(626\text{-}662)}$(A, E) |
| BTWXEWDXEINNYTXLIHXLIEESQNQXEKNXQELLE | SAH-gp41$_{(626\text{-}662)}$(A, D, F) |
| YTSLIHSLIEESQNQQEKNEQELLELDKWASLWNWF | gp41$_{(638\text{-}673)}$ |
| YTXLIHXLIEESQNQQEKNEQELLELDKXASLXNWF | SAH-gp41$_{(638\text{-}673)}$(D, H) |
| YTXLIHXLIEESQNQQEKNEQELLELXKWAXLWNWF | SAH-gp41$_{(638\text{-}673)}$(D, G) |
| YTSLIHSLIEESQNQXEKNXQELLELDKXASLXNWF | SAH-gp41$_{(638\text{-}673)}$(F, H) |
| YTXLIHXLIEESQNQXEKNXQELLELDKWASLWNWF | SAH-gp41$_{(638\text{-}673)}$(D, F) |
| YTSLIHSLIXESQXQQEKNEQELLELXKWAXLWNWF | SAH-gp41$_{(638\text{-}673)}$(E, G) |
| YTSLIHSLIXESQXQQEKNEXELLXLDKWASLWNWF | SAH-gp41$_{(638\text{-}673)}$(E, K) |
| YTXLIHXLIEESQNQXEKNXQELLELXKWAXLWNWF | SAH-gp41$_{(638\text{-}673)}$(D, F, G) |
| BTWBXWDRXINNYTSLIHSLIEESQNQQEKNEQELLE | SAH-gp41$_{(626\text{-}662)}$(A') |
| BTWBEWDREINNYTSLIHSLIEESQNXQEKXEQELLE | SAH-gp41$_{(626\text{-}662)}$(F') |
| BTWBXWDRXINNYTSLIHSLIEESQNQXEKNXQELLE | SAH-gp41$_{(626\text{-}662)}$(A',F) |
| BTWBXWDRXINNYTSLIHSLIEESQNXQEKXEQELLE | SAH-gp41$_{(626\text{-}662)}$(A',F') |

(SEQ ID NOS 80-87, 1 and 88-98, respectively, in order of appearance)

(SEQ ID NOS 99-100 and 82-85, respectively, in order of appearance)

| Compound | %-helicity at pH 2 | %-helicity at pH 7 |
|---|---|---|
| SAH-gp41(626-662) | 37 | 13 |
| SAH-gp41(626-662)(F) | 82 | 63 |
| SAH-gp41(626-662)(C, F) | 55 | 41 |
| SAH-gp41(638-673) | 49 | 19 |
| SAH-gp41(638-673)(D) | 79 | 23 |
| SAH-gp41(638-673)(F) | 57 | 30 |
| SAH-gp41(638-673)(G) | 61 | 48 |
| SAH-gp41(638-673)(H) | 66 | 26 |

FIGURE 16C

| compound | half-life, minutes |
|---|---|
| gp41$_{(626-662)}$ | 14 |
| SAH-gp41$_{(626-662)}$(F) | 102 |
| SAH-gp41$_{(626-662)}$(A) | 79 |
| SAH-gp41$_{(626-662)}$(A,F) | 301 |
| SAH-gp41$_{(626-662)}$(B,F) | 1275 |
| SAH-gp41$_{(626-662)}$(C,F) | 494 |
| SAH-gp41$_{(626-662)}$(D,F) | 181 |

| compound | half-life, minutes |
|---|---|
| gp41$_{(638-673)}$ | 15 |
| SAH-gp41$_{(638-673)}$(D) | 32 |
| SAH-gp41$_{(638-673)}$(F) | 21 |
| SAH-gp41$_{(638-673)}$(G) | 128 |
| SAH-gp41$_{(638-673)}$(H) | 201 |
| SAH-gp41$_{(638-673)}$(D, H) | 510 |
| SAH-gp41$_{(638-673)}$(D, G) | 1710 |
| SAH-gp41$_{(638-673)}$(F, H) | 132 |
| SAH-gp41$_{(638-673)}$(D, F) | 652 |
| SAH-gp41$_{(638-673)}$(E, G) | 483 |

FIGURE 16F

| compound | half-life, minutes |
|---|---|
| gp41(626-662) | 11 |
| SAH-gp41(626-662)(F) | 129 |
| SAH-gp41(626-662)(A) | 118 |
| SAH-gp41(626-662)(A,F) | 2040 |
| SAH-gp41(626-662)(B,F) | 930 |

| compound | half-life, minutes |
|---|---|
| gp41(638-673) | 4 |
| SAH-gp41(638-673)(D) | 3 |
| SAH-gp41(638-673)(G) | 227 |
| SAH-gp41(638-673)(D, G) | 3320 |
| SAH-gp41(638-673)(D, H) | 920 |

| | gp41(638-673) | SAH-gp41(638-673)(D) | SAH-gp41(638-673)(G) | SAH-gp41(638-673)(D, G) | SAH-gp41(638-673)(D, H) |
|---|---|---|---|---|---|
| ADA | 762 +/- 492 | 129 +/- 51 | 600 +/- 194 | 161 +/- 34 | >3000 nM |
| HX | 446 +/- 191 | 30 +/- 12 | 802 +/- 66 | 146 +/- 58 | 978 +/- 540 |
| 3.2 | 330 +/- 103 | 77 +/- 6 | 662 +/- 38 | 87 +/- 29 | 833 +/- 441 |
| AMLV | >3000 | >3000 | >3000 | >3000 | >3000 |
| YU2 | >3000 | | | | |

IC50, nM

| | gp41(626-662) | SAH-gp41(626-662)(A) | SAH-gp41(626-662)(F) | SAH-gp41(626-662)(A, F) | SAH-gp41(626-662)(B, F) |
|---|---|---|---|---|---|
| ADA | 19 +/- 1 | 20 +/- 4 | 23 +/- 5 | 21 +/- 2 | 218 +/- 95 |
| HX | 17 +/- 2 | 16 +/- 1 | 19 +/- 3 | 18 +/- 1 | 1045 +/- 87 |
| 3.2 | 20 +/- 3 | 18 +/- 1 | 29 +/- 3 | 20 +/- 4 | 282 +/- 15 |
| YU2 | >3000 | 339 +/- 162 | 1958 +/- 259 | 87 +/- 30 | >3000 |
| AMLV | >3000 | >3000 | >3000 | >3000 | >3000 |

|  | T865 | T865(V38A,N42T) |
|---|---|---|
| gp41(638-673) | 0.58 | 0.36 |
| gp41(626-662) | 0.84 | 0.37 |
| SAH-gp41(626-662)(A,F) | 0.80 | 0.73 |
| SAH-gp41(626-662)(F) | 0.95 | 0.84 |
| SAH-gp41(626-662)(A) | 0.65 | 0.39 |

IC50, nM

|  | gp41 (626-662) | SAH-gp41 (626-662)(A) | SAH-gp41 (626-662)(F) | SAH-gp41 (626-662)(A, F) | gp41 (638-673) |
|---|---|---|---|---|---|
| YU2 | >3000 | 339 +/- 162 | 1958 +/- 259 | 87 +/- 30 | >3000 |

FIGURE 21

| Sample no. | Dose (mg/kg) | Route | Collection time (h) | Concentration in plasma (μg/mL)[a] | |
|---|---|---|---|---|---|
| | | | | gp41(626-662) (μg/mL) | SAH-gp41(626-662)(A,F) (μg/mL) |
| 7227 | 10 | oral | 0.5 | <LOD | |
| 7228 | 10 | oral | 0.5 | <LOD | |
| 7229 | 10 | oral | 0.5 | <LOD | |
| 7230 | 10 | intravenous | 0.5 | 7.1 | |
| 7231 | 10 | intravenous | 0.5 | 6.2 | |
| 7232 | 10 | intravenous | 0.5 | 7.8 | |
| 7206 | 10 | oral | 0.5 | | 1.7 |
| 7207 | 10 | oral | 0.5 | | 1.4 |
| 7208 | 10 | oral | 0.5 | | 1.3 |
| 7209 | 10 | intravenous | 0.5 | | 47.3 |
| 7210 | 10 | intravenous | 0.5 | | 45.4 |
| 7226 | 10 | intravenous | 0.5 | | 40.3 |

[a] Lower limit of quantitation, 1.25 μg/mL; <LOD, undetectable.

US 10,259,848 B2

COMPOSITIONS AND METHODS COMPRISING HYDROCARBON-STAPLED POLYPEPTIDES

CROSS REFERENCE TO RELATED APPLICATIONS

This application is a continuation of U.S. application Ser. No. 15/019,558, filed on Feb. 9, 2016, which is a continuation of U.S. application Ser. No. 12/864,375, filed on Jul. 23, 2010 (now U.S. Pat. No. 9,290,545), which is a continuation of International Application No.: PCT/US2009/000438 (WO2009/108261), filed on Jan. 23, 2009, which claims priority to U.S. Provisional Patent Application Ser. No. 61/062,007 filed on Jan. 23, 2008, each of which is incorporated herein by reference in its entirety.

SEQUENCE LISTING

The instant application contains a Sequence Listing which has been submitted in ASCII format via EFS-Web, and is hereby incorporated by reference in its entirety. Said ASCII copy, created on Jun. 24, 2011, is named 69208US7.txt and is 79,397 bytes in size.

BACKGROUND

The molecular process of viral fusion, in which viral coat proteins recognize and bind to surface receptors of the host cell, is a critical target in the prevention and treatment of viral infections. Upon recognition of the viral glycoprotein by host cellular receptors, viral fusion proteins undergo conformational changes that are essential to viral fusion and infection. A series of hydrophobic amino acids, located at the N- and C-termini organize to form a complex that pierces the host cell membrane. Adjacent viral glycoproteins containing two amphipathic heptad repeat domains fold back on each other to form a trimer of hairpins, consisting of a bundle of six α-helices. This six-helix bundle motif is highly conserved among many viral families, including Filovirus (ebola), (Malashkevich, V. N., et al., *PNAS*, 1999. 96(6): p. 2662-2667; Weissenhorn, W., et al., *Molecular Cell*, 1998. 2(5): p. 605-616), Orthomyxovirus (influenza) (Wilson, I. A., J. J. Skehel, and D. C. Wiley, *Nature*, 1981. 289(5796): p. 366-37; Bullough, P. A., et al., *Nature*, 1994. 371(6492): p. 37-43), Coronavirus (SARS) (Xu, Y. H., et al. *Journal of Biological Chemistry*, 2004. 279(47): p. 49414-49419), Paramyxovirus (HRSV) (Zhao, X., et al., *PNAS*, 2000. 97(26): p. 14172-14177) and Retrovirus (HIV) (Chan, D. C., et al., *Cell*, 1997. 89(2): p. 263-27; Weissenhorn, W., et al., *Nature*, 1997. 387(6631): p. 426-430).

HIV envelope proteins gp120 and gp41 non-covalently associate with each other to form a trimer of dimers. On the host cell, gp120 specifically interacts with CD4, CXCR4, and CCR5, which are the glycoproteins involved in host-cell recognition. gp41, the viral membrane spanning glycoprotein, is responsible for fusing the viral and cellular membranes, resulting in viral particle uptake by the host cell. Once gp120 binds to CD4, gp41 undergoes a conformational change, transforming from its native state into a fusogenic six-helix bundle. The regions of gp41 involved in this change are 43 (C43) residues of the C-terminal heptad repeat (CHR or HR-2), near the transmembrane domain, and 51 (N51) residues of the N-terminal heptad repeat (NHR or HR-1), found just proximal to the fusion peptide domain. Peptides N51 and C43 orient to form helical antiparallel heterodimers, which associate to form a higher order trimeric complex that is thermo- and proteolytically stable.

Peptides which interfere with this viral fusogenic process can be used for the prevention and treatment of viral infections. For example, peptides corresponding to residues 553-590 of the gp41 N-terminal heptad repeat domain (HR-1) and residues 630-659 and 648-673 of the C-terminal heptad repeat domain (HR-2) of HIV have been shown to inhibit the replication of a variety of HIV strains. Studies have determined that these peptides inhibit cell-cell fusion by interacting with the HIV envelope glycoproteins.

T20 or enfuvirtide, is the first fusion inhibitor peptide developed based on the CHR region of gp41 for the treatment of HIV. Enfuvirtide is active at nanomolar concentrations against many strains and subtypes of HIV, including the common lab strains and primary isolates of HIV-1 and HIV-2 (Wild, C. T., et al., *PNAS*, 1994. 91(21): p. 9770-9774).

However, enfuvirtide has remained a tertiary treatment option due to a variety of factors which include cost, no oral bioavailability (subcutaneous injections limit accessibility and compliance) and poor in vivo stability (Kilby, J. M., et al., *Nucleic Aids Research and Human Retroviruses*, 2002. 18(10): p. 685-693), and loss of bioactive secondary structure. Thus, although peptide-based inhibition of viral fusion processes is mechanistically feasible and clinically effective, the biophysical and biochemical properties of amphipathic fusion peptides present numerous challenges which hinder their use.

SUMMARY OF THE INVENTION

The present invention is directed to compositions, kits and methods utilizing polypeptides with stabilized α-helical structures (herein also referred to as SAH). The compositions are useful for treating and/or preventing viral infections. The invention is based, at least in part, on the result provided herein demonstrating that viral hydrocarbon stapled alpha helical peptides display excellent proteolytic, acid, and thermal stability, restore the native alpha-helical structure of the peptide, are highly effective in interfering with the viral fusogenic process, and possess superior pharmacokinetic properties compared to the corresponding unmodified peptides.

In a first aspect, the invention is directed to a modified polypeptide having a stabilized viral alpha helix heptad repeat domain. Preferably the alpha helix heptad repeat domain is stabilized with at least one hydrocarbon staple, but could include two, three or more hydrocarbon staples. Suitable hydrocarbon staples (e.g., tethers) are described herein. Suitable viral alpha helix heptad repeat domains are derived from any virus with an alpha helix domain or analog thereof that is directly or indirectly involved in cell attachment and/or fusion. Suitable stabilized alpha helical heptad repeat domains can be derived from numerous viruses, including respiratory syncytial virus, parainfluenza virus, influenza virus, coronavirus, ebolavirus and HIV. The modified polypeptides of the invention can include a stabilized HIV gp41 heptad repeat domain (e.g., heptad repeat domain 1 or 2, or portions thereof).

Any of the modified polypeptides of the invention can be included in compositions and kits.

In another aspect, the invention is directed to a method for inhibiting the transmission of HIV to a cell. In the method, the HIV virus is contacted with an effective dose of a modified polypeptide so that the HIV virus is inhibited from infecting the cell. Preferably, the modified polypeptide has an HIV gp41 heptad repeat domain (e.g., heptad repeat domain 1 or 2, or portions thereof) that is stabilized with a hydrocarbon staple.

The invention may also include a method for treating or delaying the onset of AIDS in an HIV infected individual. A pharmaceutical composition having a modified polypeptide with a stabilized HIV gp41 heptad repeat domain (e.g., heptad repeat domain 1 or 2, or portions thereof) is administered to an individual infected with HIV, thus treating or delaying the onset of AIDS. Preferably the HIV gp41 heptad repeat domain is stabilized with a hydrocarbon staple.

In still another aspect, the invention is directed to a method for increasing the number of CD4+ cells in an individual infected with HIV. The method involves administering to the individual infected with HIV an effective dose of a pharmaceutical composition having a modified polypeptide with a stabilized HIV gp41 heptad repeat domain (e.g., heptad repeat domain 1 or 2, or portions thereof). The administration of the composition results in an increase in the number of CD4+ cells in the individual. Preferably the HIV gp41 heptad repeat domain is stabilized with a hydrocarbon staple.

In yet another aspect, the invention is directed to a method for inhibiting syncytia formation between an HIV infected cell and an uninfected cell. The method involves contacting the infected cell with an effective dose of a modified polypeptide having a stabilized HIV gp41 heptad repeat domain (e.g., heptad repeat domain 1 or 2, or portions thereof), thereby inhibiting syncytia formation between the cells. Preferably the HIV gp41 heptad repeat domain is stabilized with a hydrocarbon staple.

In still another aspect, the invention is directed to a method for inactivating HIV. The method involves contacting the virus with an effective dose of a modified polypeptide having a stabilized HIV gp41 heptad repeat domain (e.g., heptad repeat domain 1 or 2, or portions thereof) so that the HIV is rendered inactive (e.g., non-infectious). Preferably the HIV gp41 heptad repeat domain is stabilized with a hydrocarbon staple.

In still another aspect, the invention is directed to a method for preventing an HIV infection in an individual. The method involves administering to an individual an effective dose of a pharmaceutical composition having modified polypeptide with a stabilized HIV gp41 heptad repeat domain (e.g., heptad repeat domain 1 or 2, or portions thereof). Administration of the stabilized HIV gp41 heptad repeat domain interferes with the ability of the HIV to infect the individual. Preferably the HIV gp41 heptad repeat domain is stabilized with a hydrocarbon staple.

The modified polypeptides can be used to inhibit the transmission of RSV to a cell. The virus is contacted with an effective dose of a modified polypeptide having a stabilized RSV viral alpha helix heptad repeat domain analog thereby inhibiting transmission of the virus to a cell. Preferably the heptad repeat domain analog is stabilized with the hydrocarbon staple.

The modified polypeptides can also be used to inhibit the transmission of a parainfluenza virus to a cell. The virus is contacted with an effective dose of a modified polypeptide having a stabilized parainfluenza viral alpha helix heptad repeat domain analog, thereby inhibiting transmission of the virus to a cell. Preferably the heptad repeat domain analog is stabilized with the hydrocarbon staple.

In another aspect, the modified polypeptides can also be used to inhibit the transmission of an influenza virus to a cell. The virus is contacted with an effective dose of a modified polypeptide having a stabilized influenza viral alpha helix heptad repeat domain analog, thereby inhibiting transmission of the virus to a cell. Preferably the heptad repeat domain analog is stabilized with the hydrocarbon staple.

In still another aspect, the invention is directed to a method for inhibiting the transmission of a coronavirus to a cell. The method includes contacting the coronavirus with an effective dose of a modified polypeptide having a stabilized coronavirus alpha helix heptad repeat domain analog, thereby inhibiting transmission of the virus to a cell. Preferably the heptad repeat domain analog is stabilized with the hydrocarbon staple.

In yet still another aspect, the invention is directed to a method for inhibiting the transmission of an ebolavirus to a cell. The method includes contacting the ebolavirus with an effective dose of a modified polypeptide having a stabilized ebolavirus alpha helix heptad repeat domain analog, thereby inhibiting transmission of the virus to the cell. Preferably the heptad repeat domain analog is stabilized with a hydrocarbon staple.

In an aspect of the invention, the invention provides modified peptides of the inventions as a pharmaceutical composition. In some embodiments, the pharmaceutical composition is for enteral administration, preferably oral administration.

In yet another aspect, the alpha helix heptad repeat domains and analogs thereof are used to generate an antibody response to the polypeptides by administering the polypeptides to a subject. Furthermore, the antibodies generated directly or indirectly (e.g., humanized antibodies) by the administration of the polypeptides may then be used to prevent or treat a viral infection (e.g., HIV, RSV, parainfluenza, influenza, coronavirus, ebolavirus).

BRIEF DESCRIPTION OF THE DRAWINGS

FIG. 1 illustrates the domains of the gp41 glycoprotein.

FIG. 2A and FIG. 2B illustrate the amino acid sequence for FIG. 2A) HX-strain of gp160 (SEQ ID NO: 49) and FIG. 2B) YU2-strain of gp160 (SEQ ID NO: 50), with HR-1 domain bolded and underlined and HR-2 domain bolded and italicized.

FIG. 3 illustrates the amino acid sequences for HIV-1 gp41 HR-1 and HR-2 domains and homologous regions in other viruses (SEQ ID NOS: 14, 7, 9, 11, 51-54, 8, 10, 12, and 55-57, respectively, in order of appearance).

FIG. 5A provides examples of amino acid sequence templates from within the HIV-1 HR-2 domain polypeptides with sequential N-terminal truncations. Shown are N-terminal truncations of the polypeptides of SEQ ID NOS: 1, 13, 58, and 59, respectively.

FIG. 5B provides examples of amino acid sequence templates from within the HIV-1 HR-2 domain polypeptides with sequential C-terminal truncations. Shown are C-terminal truncations of the polypeptides of SEQ ID NOS: 1, 13, 58, and 59, respectively.

FIG. 6 provides examples of sequence templates from within the HIV-1 HR2 domain depicting staggered N- and C-terminal truncations. Shown are staggered N- and C-terminal truncations of the polypeptides of SEQ ID NOS: 1, 13, 58, and 59, respectively.

FIG. 7 illustrates a synthetic design of a truncated SAH-gp41 compound, SAH-gp41$_{(626-645)}$(A) (SEQ ID NO: 61), which is based on gp41$_{(626-645)}$ (SEQ ID NO: 60). X=S5 amino acid, B=norleucine.

FIG. 8 provides examples of sequence templates from within the HR2 domains of SIV (SEQ ID NO: 62) and the HX (SEQ ID NOS: 1 and 13) and YU2 (SEQ ID NOS: 58 and 59) strains of HIV-1 depicting the generation of chimeras (SEQ ID NO: 62).

FIG. 9A-FIG. 9D illustrate the heptad repeat domain motif as applied to HIV gp41 (626-663) (SEQ ID NO: 66) and associated preferred amino acid residues. FIG. 9A presents the heptad repeat domain. FIG. 9B presents HIV gp41 (626-663). FIG. 9C presents the heptad position a, d. FIG. 9D presents a sequence associated with the heptad repeat domain. Examples of sequence template from within the HIV-1 HR2 domain depicting the specific amino acid residues necessary to preserve the HR1 interaction are provided (SEQ ID NOS: 44 and 45). Thus, the positions indicated with a dash may be amenable to substitution/mutation without disruption of activity.

FIGS. 10A-FIG. 10D illustrate the possible combinations of helix-stabilizing crosslinks formed at positions (FIG. 10A) i, and i+4 across one turn in the helix using two S5 amino acids; (FIG. 10B) i, and i+7, across two turns of the helix using one S8 and one R5 amino acid or one R8 and one S5 amino acid; (FIG. 10C) a double crosslink employing two i, i+4, two i, i+7, or one i, i+4 and one i, i+7 crosslink; and (FIG. 10D) a triple crosslink employing any combination of i, i+4, i, i+7, or other crosslinks (e.g. i, i+3).

FIG. 14A) SAH-gp41$_{(626-662)}$ singly- and doubly-stapled peptides at pH 7, FIG. 14B) SAH-gp41$_{(638-673)}$ singly-stapled peptides at pH 7, FIG. 14C) SAH-gp41$_{(638-673)}$ doubly-stapled peptides at pH 7, FIG. 14D) SAH-gp41$_{(626-662)}$ singly- and doubly-stapled peptides at pH 2, FIG. 14E) SAH-gp41$_{(638-673)}$ singly- and doubly-stapled peptides at pH 2, FIG. 14F) Table comparing calculated percent helicities of SAH-gp41 compounds at pH 7 and pH 2.

FIG. 15B) singly-stapled SAH-gp41$_{(638-673)}$ compounds; and FIG. 15C) doubly-stapled SAH-gp41$_{(638-673)}$.

FIGS. 16A-FIG. 16F illustrate that SAH-gp41 compounds exhibit greater protease resistance to chymotrypsin at pH 7 and pepsin at pH 2 compared to the unmodified gp41 peptides; FIG. 16A) SAH-gp41$_{(626-662)}$, chymotrypsin pH 7, FIG. 16B) SAH-gp41$_{(638-673)}$ chymotrypsin pH 7, FIG. 16C) Table of half-lives of SAH-gp41 compounds in the presence of chymotrypsin, pH 7, FIG. 16D) SAH-gp41$_{(626-662)}$, pepsin pH 2, FIG. 16E) SAH-gp41$_{(638-673)}$ pepsin, pH 2, FIG. 16F) Table of half-lives of SAH-gp41 compounds in the presence of pepsin, pH 2.

FIG. 19 demonstrates the anti-viral activity of select SAH-gp41 compounds against HIV strains HXBc2, ADA, and HXBc2P 3.2, and YU2. AMLV serves as a negative control.

FIG. 20B) Tabulated values indicate fraction of HR2 peptide input bound to the indicated FITC-HR1 peptide; and B) Select SAH-gp41 compounds are notably superior to the corresponding unmodified peptides in blocking the infectivity of a resistant HIV-1 strain, YU2.

FIG. 21 shows that a doubly-stapled gp41 peptide has markedly enhanced pharmacologic properties in vivo (stability and bioavailability) compared to the corresponding unmodified peptide.

DETAILED DESCRIPTION

Figure 4A:
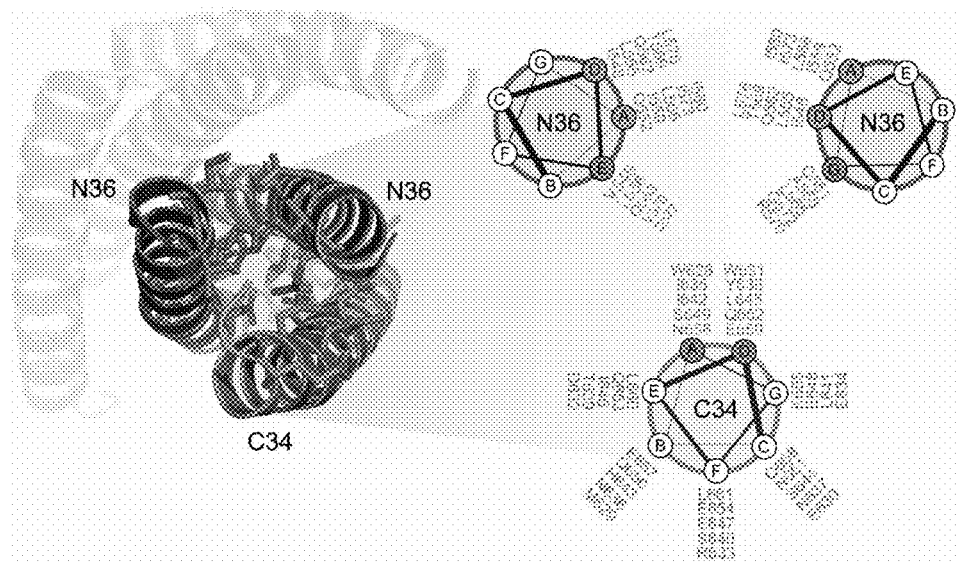
FIG. 4A illustrates the HIV six-helix bundle and key interhelix interactions of the helices N36 and C34. One of the N36 and two C34 helices are faded for clarity. The helical wheel further illustrates key contacts among the helices based upon the a, b, c, d, e, f, g, nomenclature.

The present invention is directed to compositions, kits and methods utilizing polypeptides with stabilized alpha helical structures. The compositions are useful for treating and/or preventing viral infections. The invention is based, at least in part, on the results provided herein demonstrating that viral hydrocarbon stapled alpha helical peptides have excellent structural, proteolytic, acid, and thermal stability, are highly effective in interfering with virus/cell fusion, and have superior pharmacologic properties in vivo compared to their unmodified counterparts.

The alpha helix heptad repeat domain is stabilized with at least one hydrocarbon staple, but could include two, three or more hydrocarbon staples. The inclusion of multiple hydrocarbon staples is particularly suited for alpha helical peptides that are 20 or more amino acids in length. In fact the inclusion of two more hydrocarbon staples, as shown herein, provides for exceptional structural, acid and thermal stability of the modified polypeptides, yielding bioactive peptides with strikingly enhanced pharmacologic properties in vivo.

Definitions

As used herein, the term "hydrocarbon stapling", refers to a process for stably cross-linking a polypeptide having at least two modified amino acids that helps to conformationally bestow the native secondary structure of that polypeptide. Hydrocarbon stapling allows a polypeptide, predisposed to have an alpha-helical secondary structure, to maintain its native alpha-helical conformation. This secondary structure increases resistance of the polypeptide to proteolytic cleavage and heat, and also may increase hydrophobicity. Accordingly, the hydrocarbon stapled (cross-linked) polypeptides described herein have improved biological activity relative to a corresponding non-hydrocarbon stapled (uncrosslinked) polypeptide. For example the cross-linked polypeptide can include an alpha-helical domain of an HIV polypeptide (e.g., HR-1/HR-2 domain), which can interfere with HIV attachment, fusion with, and infection of a cell. In some instances, the cross-linked polypeptide can be used to inhibit virus entry into a cell. The cross-linked polypeptides described herein can be used therapeutically, e.g., to treat HIV infection and/or AIDS.

The hydrocarbon stapled polypeptides include one or more tethers (linkages) between two non-natural amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) is also contemplated. The use of multiple cross-links is very effective at stabilizing and optimizing the peptide, especially with increasing peptide length, as is the case for some gp41 fusion peptides. Thus, the invention encompasses the incorporation of more than one crosslink within the polypeptide sequence to either further stabilize the sequence or facilitate the structural stabilization, proteolytic resistance, acid stability, thermal stability, and biological activity enhancement of longer polypeptide stretches.

The term "stable" or "stabilized", as used herein with reference to a polypeptide, refers to polypeptides which have been hydrocarbon-stapled to maintain their natural alpha-helical structure and/or improve protease resistance and/or improve acid stability and/or improve thermal stability.

As used herein, "HIV" is meant to include HIV-1 and HIV-2 and SIV. "HIV-1" means the human immunodeficiency virus type-1. HIV-1 includes but is not limited to extracellular virus particles and the forms of HIV-1 associated with HIV-1 infected cells. "HIV-2" means the human immunodeficiency virus type-2. HIV-2 includes but is not limited to extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes but is not limited to extracellular virus particles and the forms of SIV associated with SIV infected cells.

Figure 4B:
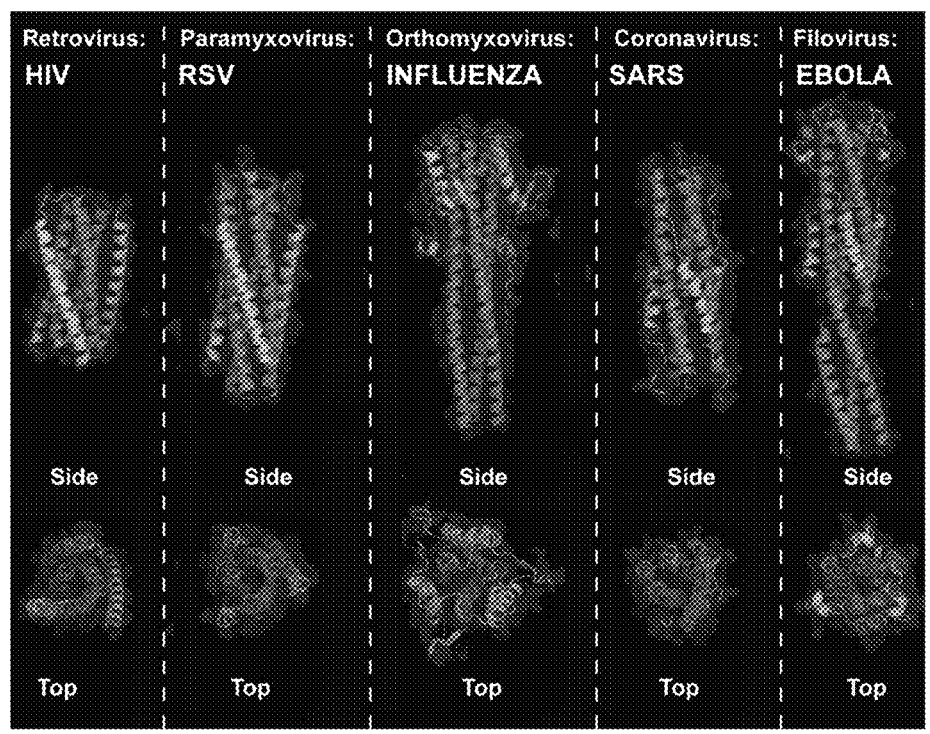
FIG. 4B illustrates the fusogenic bundle formed by HR-analog domains from RSV, influenza, SARS and Ebola. The six-helix fusogenic bundle is highly conserved across many species.
Figure 11:
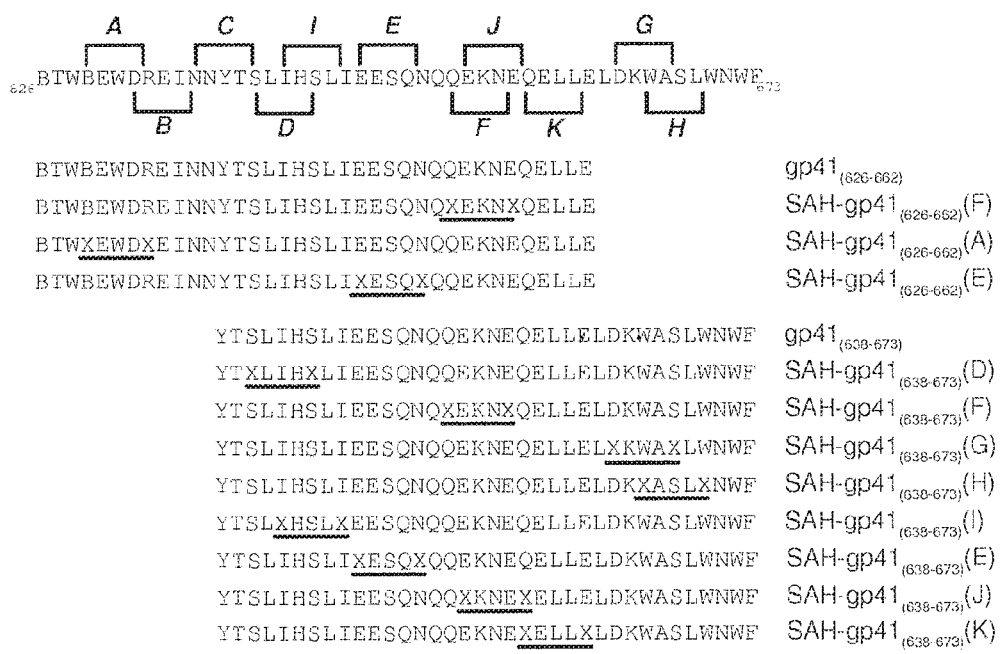
FIG. 11 illustrates SAH-gp41 singly stapled peptides (SEQ ID NOS: 67-71, 1, and 72-79, in order of appearance). (e.g., N-term: Ac, FITC-βAla, Biotin-βAla; C-term: CONH$_2$, COOH). X=S5 amino acid, B=norleucine FIG. 12 includes sequences of doubly and triply stapled SAH gp41 peptides (SEQ ID NOS 80-87, 1 and 88-98, in order of appearance). (e.g., N-term: Ac, FITC-βAla, Biotin-βAla; C-term: CONH$_2$, COOH). X=S5 amino acid, B=norleucine.
Figure 13:
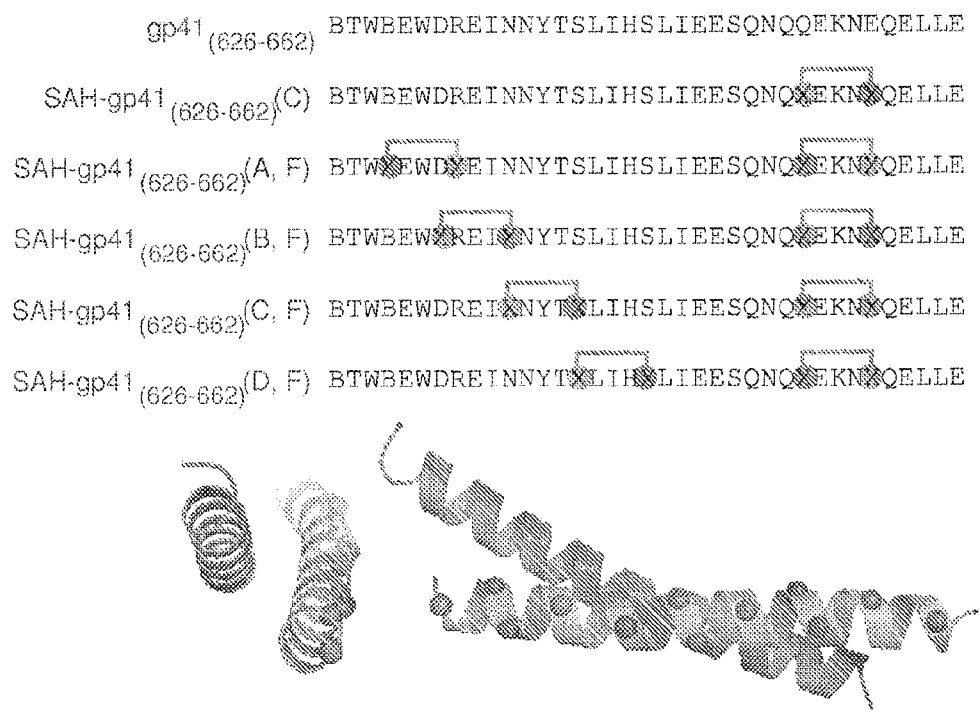
FIG. 13 illustrates unstapled, singly stapled and doubly stapled gp41 HR-2 peptides (SEQ ID NOS 99-100 and 82-85, in order of appearance) and illustrates a strategy for locating the staples in the helix. Staples are positioned so as to preserve and/or optimize inter-helix interaction surfaces. X=S5 amino acid, B=norleucine
Figure 14A:
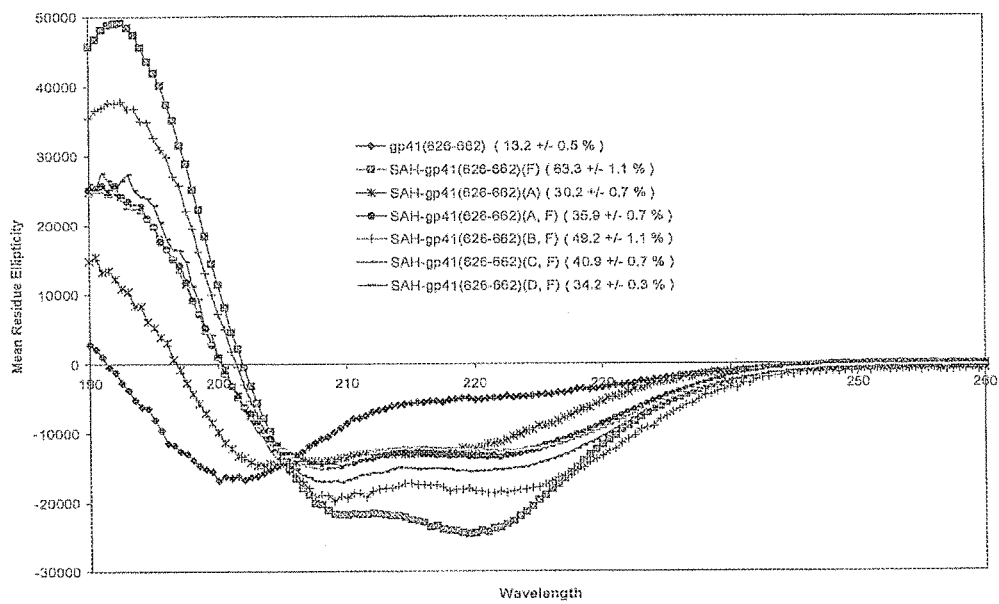
FIGS. 14A-FIG. 14F illustrate that singly and doubly stapled SAH-gp41 compounds exhibit greater helical stability as compared to the unmodified gp41 peptides at pH 7 and pH2. Percent helicity for each compound is indicated in parenthesis.
Figure 14B:
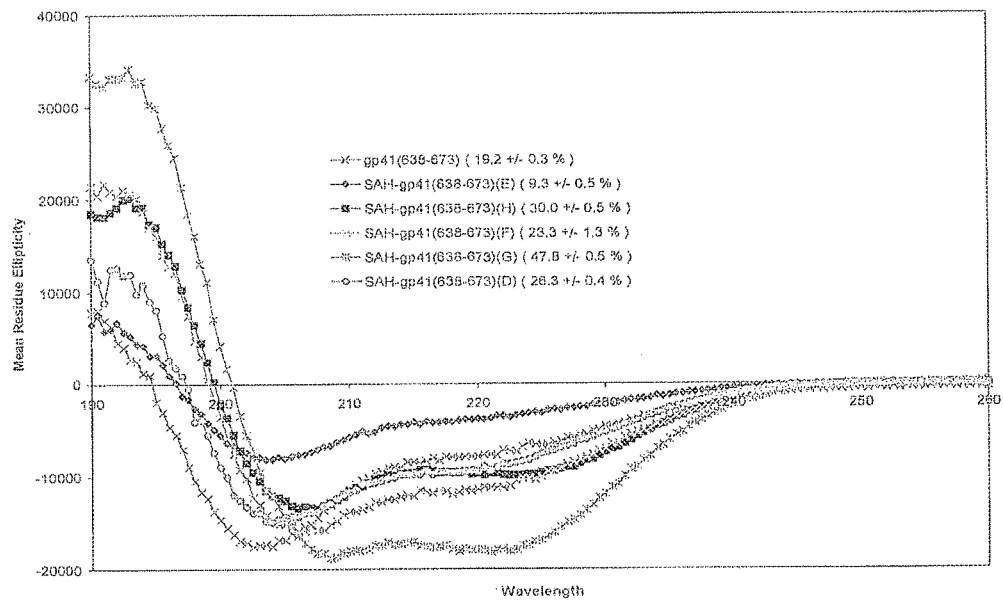
Figure 14C:
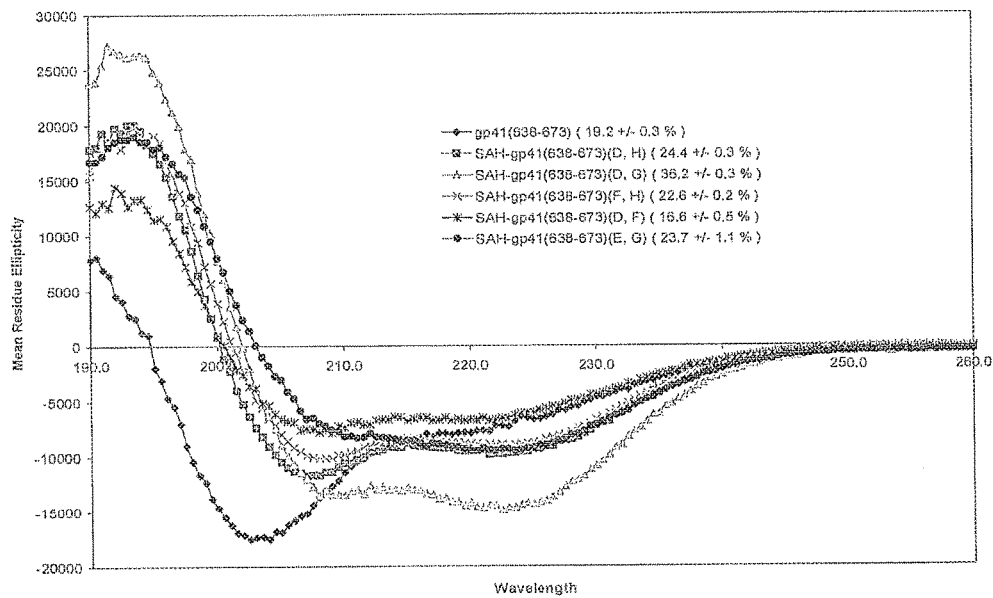
Figure 14D:
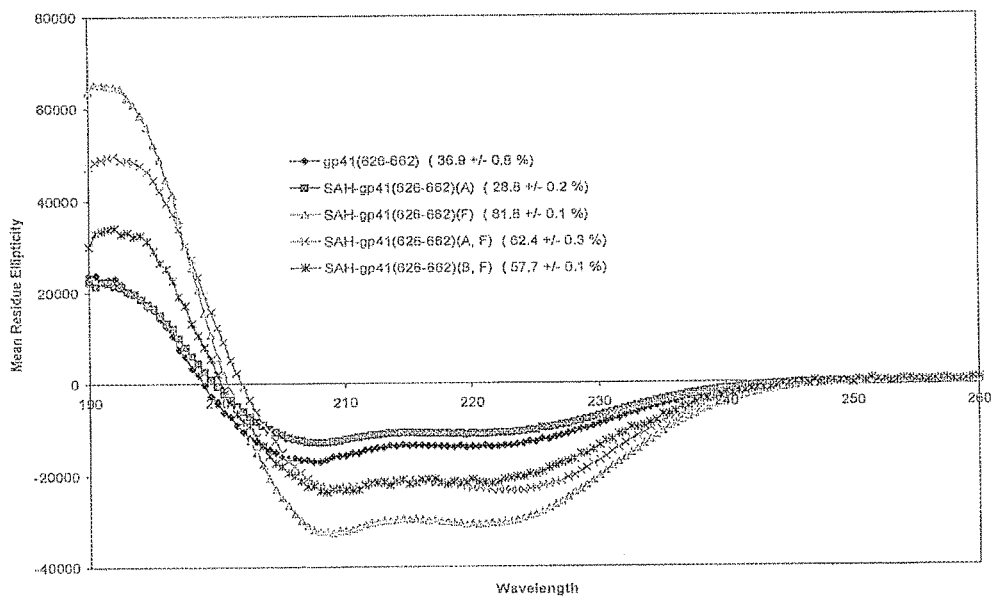
Figures 14E, 14F:
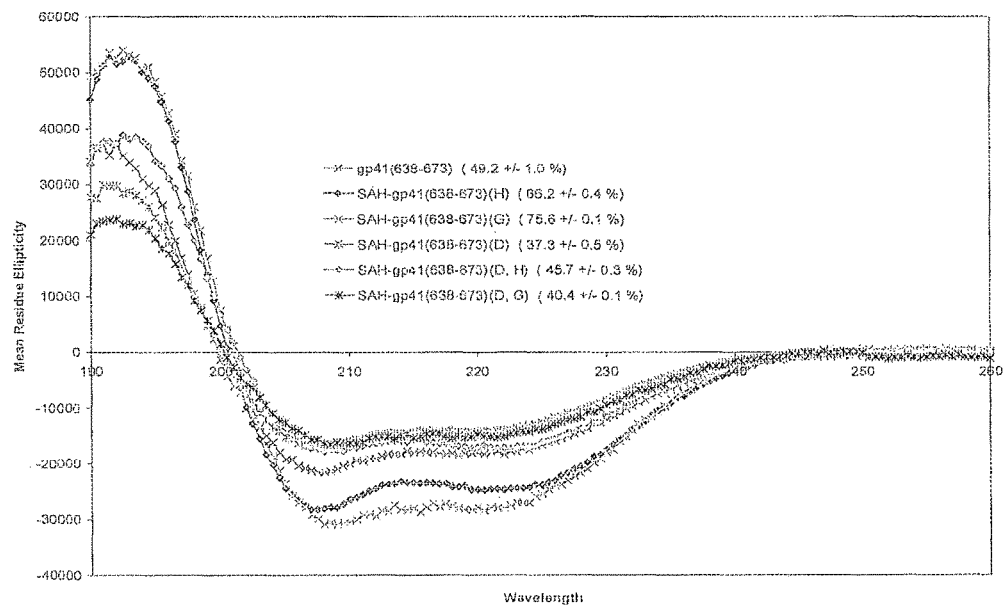
Figure 15A:
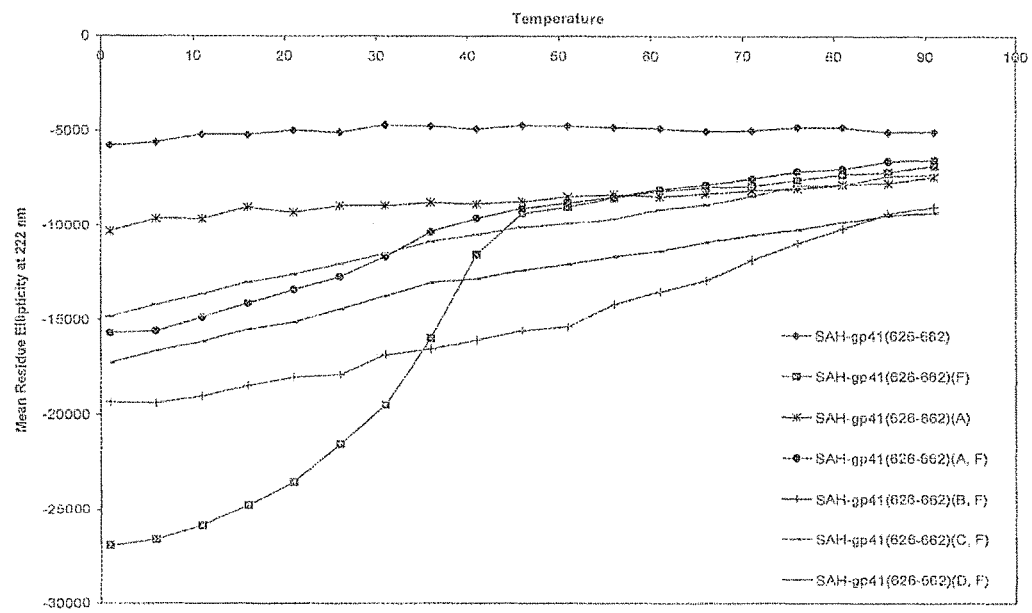
FIGS. 15A-FIG. 15C illustrate that singly and doubly stapled SAH-gp-41 compounds exhibit greater thermal stability compared to the unmodified gp41 peptides at pH 7 FIG. 15A) select singly- and doubly-stapled SAH-gp41$_{(626-662)}$ compounds.
Figure 15B:
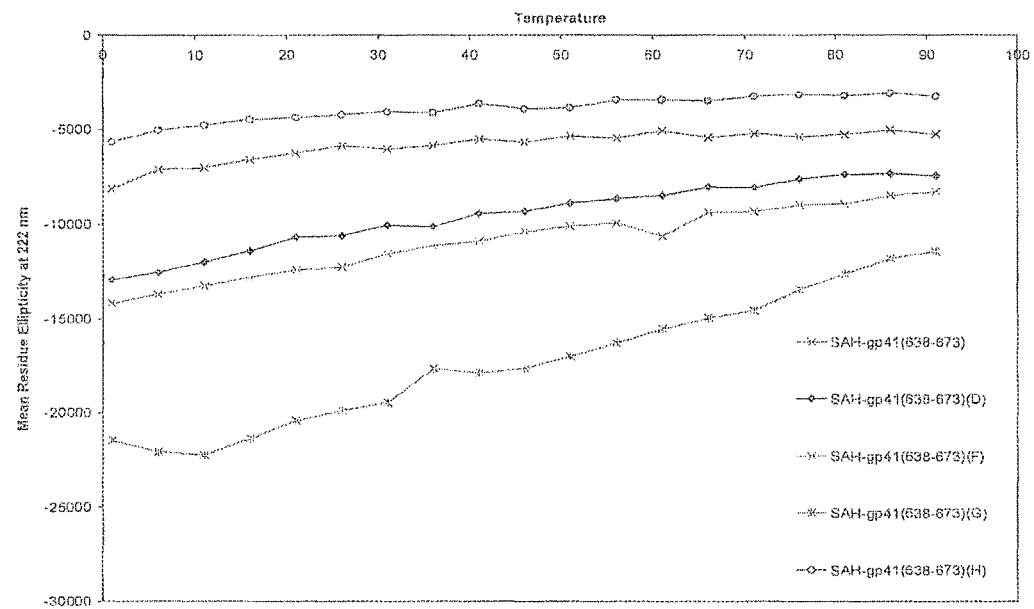
Figure 15C:
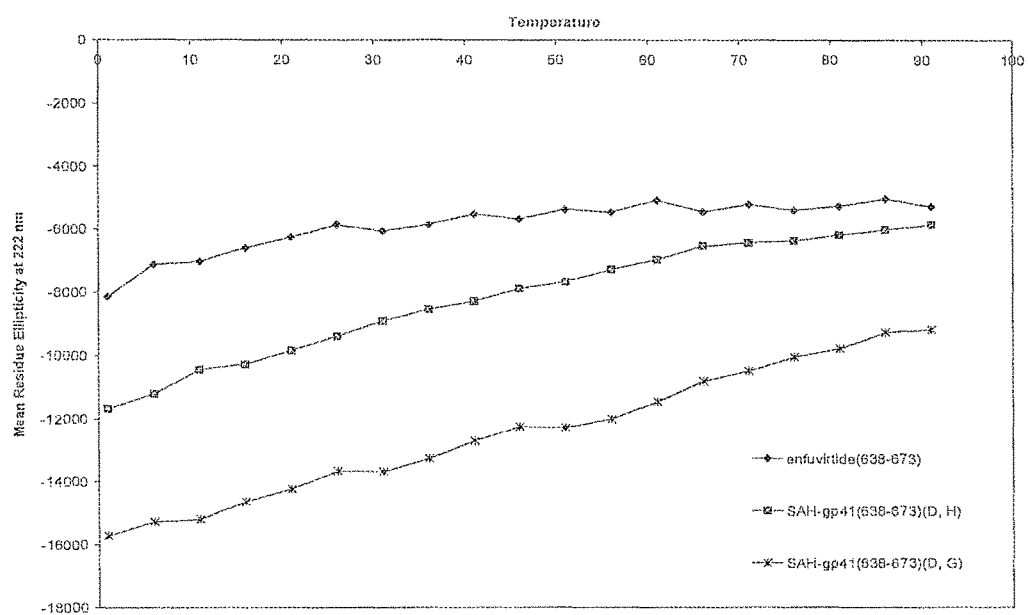
Figure 16A:
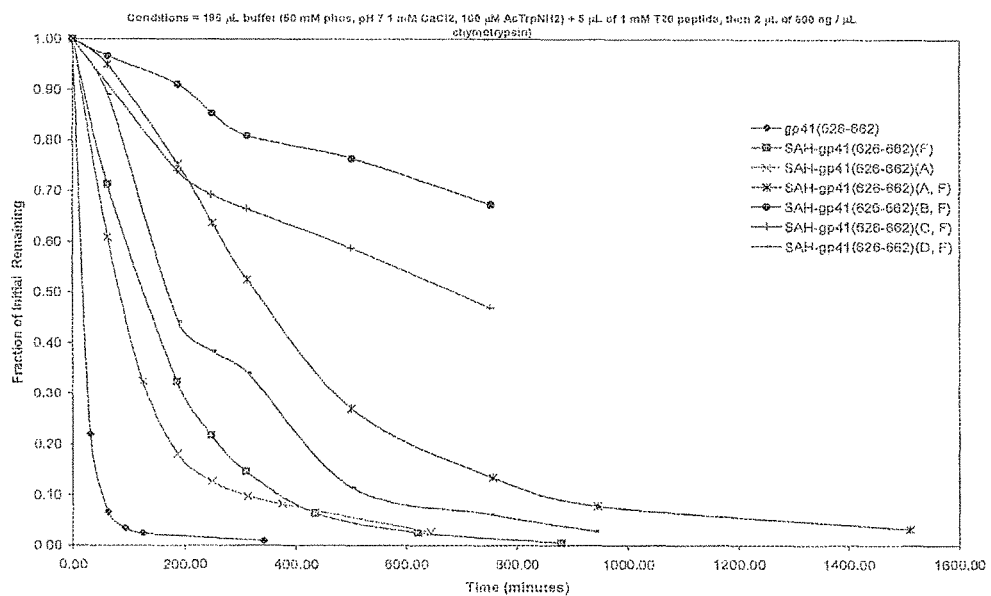
Figure 16B:
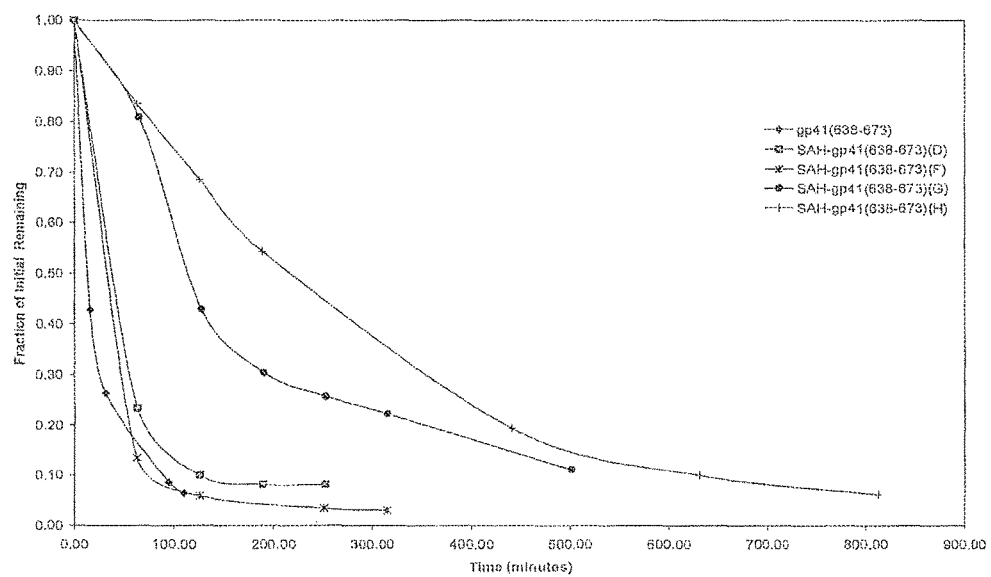
Figure 16D:
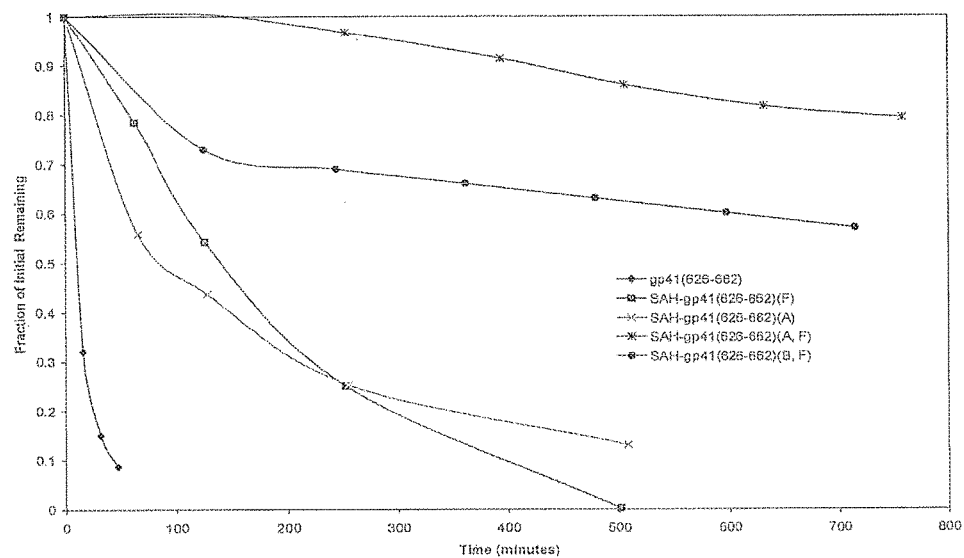
Figure 16E:
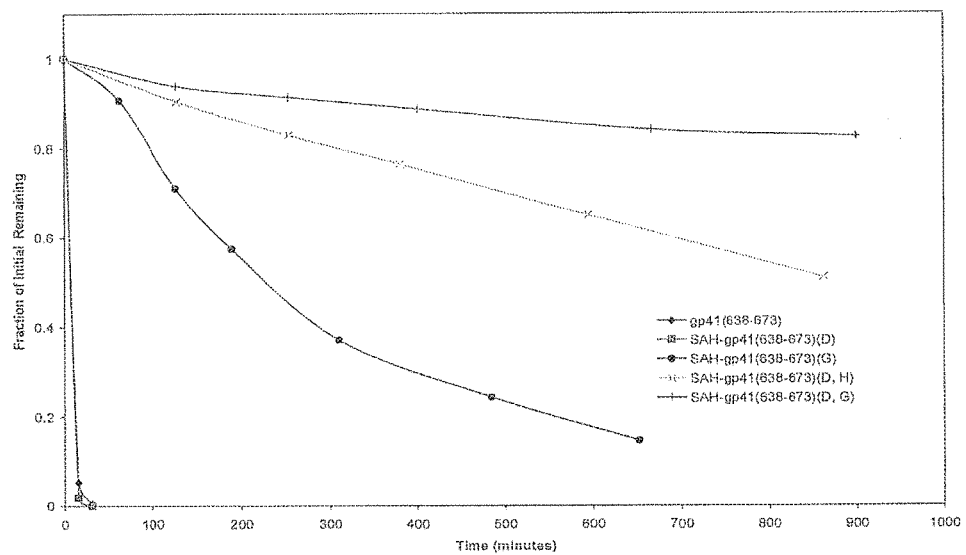

As used herein a "heptad repeat domain" and "HR domain" refers to a polypeptide that forms an alpha-helix when properly folded. The terms, "heptad repeat domain" and "HR domain" include "HR-like" and "HR-analog" polypeptides. Numerous viral proteins involved in cell attachment and fusion contain HR, HR-like and HR-analog domains including, HIV, parainfluenza, coronavirus, and others. Generally, HR domains are derived from gp41 of HIV, while HR-analog domains are derived from the envelope glycoproteins of non-HIV viruses. Many HR and HR-analog domain polypeptides are known in the art and described herein. In one embodiment, the HR domain has an amino acid sequence which is 40%, 50%, 60%, 70%, 80%, or more identical to FIG. 5, FIG. 6 or SEQ ID NO:1-14. It should be noted that HR and HR-like domains may have low homology but will share a common alpha helical structure, with more conservation on the interaction surfaces than non-interacting surfaces (see FIGS. 4 and 9).

In one embodiment, the HR modified polypeptide includes a heptad repeat domain having the formula: a b c d e f g, wherein a and d are hydrophobic amino acid residues and b, c, e, f and g are any amino acid. Preferably, the formula is repeated in tandem two or more times.

For example, in a further embodiment the heptad repeat domain of the modified polypeptide has the formula: W(a), b, c, W(d), e, f, g, I(a), b, c, Y(d), e, f, g, I(a), b, c, L(d), e, f, g, S(a), b, c, Q(d), e, f, g, N(a), b, c, E(d), e, f, g, L(a), or conservative amino acid substitutions thereof and wherein the b, c, e, f and g can be any amino acid (e.g., residues 3-38 of SEQ ID NO: 44).

In a further, embodiment the heptad repeat domain of the modified polypeptide has the formula: T(g), W(a), b, c, W(d), D(e), R(f), g, I(a), b, c, Y(d), e, f, g, I(a), b, c, L(d), I(e), f, g, a, Q(b), c, d, Q(e), E(f), K(g), a, E(b), c, d, L(e), f, E(g), L(a), or conservative amino acid substitutions thereof and wherein non-designated amino acids can be any amino acid (e.g., residues 2-38 of SEQ ID NO: 45).

The HR regions are known to comprise a plurality of 7 amino acid residue stretches or "heptads" (the 7 amino acids in each heptad designated "a" through "g"), wherein the amino acids in the "a" position and "d" position are generally hydrophobic. Generally the HR region will include one or more leucine zipper-like motifs (also referred to as "leucine zipper-like repeats") comprising an 8 amino acid sequence initiating with, and ending with, an isoleucine or leucine. Heptads and leucine zipper like-motifs contribute to formation of a coiled coil structure of gp41, and of a coiled coil structure of peptides derived from the HR regions. Generally, coiled coils are known to be comprised of two or more helices that wrap around each other in forming oligomers, with the hallmark of coiled coils being a heptad repeat of amino acids with a predominance of hydrophobic residues at the first ("a") and fourth ("d") positions, charged residues frequently at the fifth ("e") and seventh ("g") positions, and with the amino acids in the "a" position and "d" position being primary determinants that influence the oligomeric state and strand orientation (see, e.g., Akey et al., 2001, *Biochemistry*, 40:6352-60).

The effect on stability and oligomerization state of a model coiled coil, by substituting various amino acids at various positions including the "a" and "d" positions, have been reported previously, wherein formation of a trimeric structure was particularly dependent on the substitution at the "d" position (see, e.g., Tripet et al., *J. Mol. Biol.* 300:377-402 (2000); Wagschal et al., *J. Mol. Biol.* 285:785-803 (2000); and Dwyer et al., *PNAS USA.* 104; 12772-12777 (2007).

It will be apparent to one skilled in the art that any peptide derived from the native sequence of the HR1 domain or HR2 domain of HIV gp41 which has antiviral activity (as can be determined using methods standard in the art without undue experimentation), and which contains all or a fraction of the region can be used as a native sequence into which one or more amino acid substitutions, preferably conservative, in the domain may be introduced to produce a synthetic peptide provided with the present invention. For purposes of illustration, such HR2 peptides derived from the native sequence, and from which a synthetic peptide may be produced, may include, but are not limited to, those illustrated in FIGS. 5 and 6.

It is apparent to those of ordinary skill in the art that some HR and HR-analog domain residues are less prone to substitution while others are more accepting of changes. For example, it is preferable not to mutate or to only conservatively mutate the amino acids at positions a and d of the heptad repeat (See FIG. 9). In one embodiment, the heptad repeat domain has the formula a, b, c, d, e, f, g, wherein a and d are hydrophobic amino acids. In a further embodiment, the heptad repeat domain has two or more repeats of the formula a, b, c, d, e, f, g. For example, in one embodiment the HR domain will have the amino acid sequences illustrated in FIG. 9 or conservative substitutions thereof. Thus, the HR and HR-like domains have significant variability in amino acid sequence but will maintain an alpha helical structure and antiviral activity.

In one embodiment, the modified polypeptide includes a heptad repeat domain having the formula: a b c de f g, wherein a and d are hydrophobic amino acid residues and b, c, e, f and g are any amino acid. Preferably, the formula is repeated in tandem two or more times.

For example, in a further embodiment the heptad repeat domain of the modified polypeptide has the formula: W(a), b, c, W(d), e, f, g, I(a), b, c, Y(d), e, f, g, I(a), b, c, L(d), e, f, g, S(a), b, c, Q(d), e, f, g, N(a), b, c, E(d), e, f, g, L(a), or conservative amino acid substitutions thereof and wherein the b, c, e, f and g can be any amino acid (e.g., residues 3-38 of SEQ ID NO: 44).

In a further, embodiment the heptad repeat domain of the modified polypeptide has the formula: T(g), W(a), b, c, W(d), D(e), R(f), g, I(a), b, c, Y(d), e, f, g, I(a), b, c, L(d), I(e), f, g, a, Q(b), c, d, Q(e), E(f), K(g), a, E(b), c, d, L(e), f, E(g), L(a), or conservative amino acid substitutions thereof and wherein non-designated amino acids can be any amino acid (e.g., residues 2-38 of SEQ ID NO: 45).

The HR, HR-like and HR-analog domains are readily identifiable by those possessing ordinary skill in the art by sequence based homology, structural homology and/or functional homology. Such methods are well known in the art and include bioinformatics programs based on pairwise residue correlations (e.g., on the world wide web at: ch.embnet.org/software/COILS_form.html), which have the ability to recognize coiled coils from protein sequences and model their structures (See Lupas, A., et al. Science 1991. 252 (5009); p. 1162-1164). Additional methods for identifying HR, HR-like and HR-analog domains are described in U.S. Pat. Nos. 6,824,783; 7,273,614; 5,464,933; and 7,122,190, all of which are herein incorporated by reference in their entirety.

In one embodiment, the modified polypeptide of the invention is 70% or more similar at the interacting face to the amino acid sequence of SEQ ID NO:1-14, FIG. 5 or FIG. 6. The "interacting face" of the alpha helix includes those amino acid residues which interact with other amino acid residues. For example, in the HIV gp41 HR-2 domain the interacting face includes the "a" and "d" position amino acids (See FIGS. 4A and 9), while the interacting face of the HIV gp41 HR-1 domain includes amino acids at positions e, g that interact with HR-2 and a, d that engage in HR1-HR1 interactions (See FIG. 4A). Methods for identifying heptad repeats and the interacting face residues are well known in the art and described herein.

An "HR-1 domain of HIV" or "heptad repeat one domain of HIV" is an N-terminal portion of the gp41 protein of HIV (the transmembrane subunit of HIV envelope) that forms an alpha-helix when properly folded. The HR-1 domain of HIV gp41 can include between 5 and 55 amino acid residues and is based on the sequence of the native HR-1 domain of HIV gp41, or a combination or chimera thereof. The HR-1 domain of HIV can include the N36 domain which encompasses amino acid residues 546-581 HIV-1 Env (See FIG. 2 and Bewley et al., *J. Biol. Chem.* 277:14238-14245 (2002)). HR-1 domain polypeptides are known in the art and described herein. In one embodiment, the HR-1 domain has an amino acid sequence which is 30% or more identical to SEQ ID NO:2 or 14.

An "HR-2 domain of HIV" or a heptad repeat two domain of HIV is a C-terminal portion of the gp41 protein of HIV (the transmembrane subunit of HIV envelope) that forms an alpha-helix when properly folded. The HR-2 domain of HIV can include the C34 domain which encompasses amino acid residues 628-661 of HIV-1 Env (See FIG. 2). HR-2 domain polypeptides are known in the art and described herein. In one embodiment, the HR-2 domain has an amino acid sequence which is 40% or more identical to SEQ ID NO:1 or 13.

As used herein, the term "chimera" or "chimeric", with reference to the polypeptides of the invention refers to a polypeptide having at least two different HR domains or having a single HR domain region that is combined in a manner not found in nature (FIG. 8). For example, the chimera polypeptide may have a first portion of an HIV-1 gp41 HR-2 domain and a second portion from a SIV gp41 HR-2 domain. These chimeric polypeptides are encoded by nucleotide sequences which can be been fused or ligated together resulting in a coding sequence which does not occur naturally. The chimera includes any functional derivative, fragments, variants, analogues, or chemical derivatives which may be substantially similar to the wild-type HR polypeptides (HIV-1 gp41 HR-2) and which possess similar activity (i.e., most preferably, 90%, more preferably, 70%, preferably 40%, or at least 10% of the wild-type HR activity, e.g., inhibiting fusion, viral infectivity).

The terms "treat," and "treating," as used herein, shall mean decrease, suppress, attenuate, diminish, arrest, or stabilize the development or progression of a disease or decrease the occurrence of pathological cells (e.g., infected cells) in an animal who is infected with the viral disorder. The treatment may be complete, e.g., the total absence of HIV in a subject. The treatment may also be partial, such that the occurrence of infected cells in a subject is less than that which would have occurred without the present invention. Treatment results in the stabilization, reduction or elimination of the infected cells, an increase in the survival of the patient or decrease of at least one sign or symptoms of the disease.

The terms "prevent," "preventing," and "prevention," as used herein, shall refer to a decrease in the occurrence of a disease, or decrease in the risk of acquiring a disease, or a decrease in the presentation of at least one sign or associated symptom of the disease in a subject. The prevention may be complete, e.g., the total absence of disease or pathological cells in a subject. The prevention may also be partial, such that the occurrence of the disease or pathological cells in a subject is less than that which would have occurred without the present invention.

The term "inhibits" as used herein with reference to a viral infection refers to a decrease in viral transmission, decrease in virus binding to a cellular target or decrease in disease. For example, the polypeptides of the present invention are used to inhibit viral transmission, syncytia formation, and disease associated with the virus (e.g. AIDS). A compound of the invention can be screened by many assays, known in the art and described herein, to determine whether the compound inhibits the virus (e.g., infectivity, transmission, etc.). For example, a compound of the invention can be assayed for its ability to inhibit viral infectivity by contacting a cell culture that is incubated with the virus with a test compound. The compound is found to inhibit viral infectivity when viral infectivity is 90%, 80%, 75%, 70%, 60%, 50%, 40%, 30%, 20%, 10%, 5% or less in the presence of the test compound as compared to a suitable control (population of cells not subjected to inhibitor).

The term "inhibit transmission", as used herein, refers to the agent's ability to inhibit viral infection of cells, via, for example, cell-cell fusion or free virus infection. Such infection may involve membrane fusion, as occurs in the case of enveloped viruses, or some other fusion event involving a viral structure and a cellular structure.

The term "inhibiting syncytia formation", as used herein, refers to an agent's ability to inhibit or reduce the level of membrane fusion events between two or more moieties relative to the level of membrane fusion which occurs between said moieties in the absence of the agent. The moieties may be, for example, cell membranes or viral structures, such as viral envelopes.

The terms "effective amount," or "effective dose" refers to that amount of an agent to produce the intended pharmacological, therapeutic or preventive result. The pharmacologically effective amount results in the amelioration of one or more symptoms of a viral disorder, or prevents the advancement of a viral disease, or causes the regression of the disease or decreases viral transmission. For example, a therapeutically effective amount preferably refers to the amount of a therapeutic agent that decreases the rate of transmission, decreases HIV viral load, or decreases the number of infected cells, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more. A therapeutically effective amount, with reference to HIV, also refers to the amount of a therapeutic agent that increases CD4+ cell counts, increases time to progression to AIDS, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and non-naturally occurring amino acids prepared by organic synthesis or other metabolic routes.

A "non-essential" amino acid residue is a residue that can be altered from the wild-type sequence of a polypeptide (e.g., an HR-1 or HR-2 domain) without abolishing or substantially altering its activity/secondary structure (alpha-helical structure). An "essential" amino acid residue is a residue that, when altered from the wild-type sequence of the polypeptide, results in abolishing or substantially abolishing the polypeptide activity and/or secondary structure. Substantially abolishing is understood as reducing the activity of the peptide to less than about 30%, less than about 20%, less than about 10%, less than about 5% of the wild-type peptide in an appropriate assay (e.g., a syncytia formation assay, a viral fusion assay). The essential and non-essential amino acid residues of the HR and HR-like domains can readily be determined by methods well known in the art and are described herein. In one embodiment, an essential amino acid residue is in the "a" or "d" position of a heptad repeat domain, while non-essential amino acids may occur in a "b", "c", "e", "f" or "g" position (FIG. 9). The term "essential" amino acid residue as used herein, includes conservative substitutions of the essential amino acid. Generally, the "essential" amino acid residues are found at the interacting face of the alpha helix. For example, in the HIV gp41 HR-2 domain the interacting face includes the "a" and "d" position amino acids. (See FIGS. 4A and 9). In another embodiment, a modified polypeptide comprises a gp41 HR-1 domain having a Leu-556, Leu-565, Val-570, Gly-572, and Arg-579 (Lu, M., et al., J. Vir, 2001. 75(22); p. 11146-11156).

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted nonessential amino acid residue in a HR domain polypeptide, for example, is preferably replaced with another amino acid residue from the same side chain family or homologues across families (e.g. asparagine for aspartic acid, glutamine for glutamic acid).

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at the world wide web site ("www") of the National Center for Biotechnology Information (".ncbi") of the National Institutes of Health (".nih") of the U.S. government (".gov"), in the "Blast" directory ("/BLAST/"). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first polypeptide can be considered similar to an HIV-1 HR-1 domain when the amino acid sequence of the first polypeptide is at least 20%, 50%, 60%, 70%, 75%, 80%, 90%, or even 95% or more identical, or conservatively substituted, to a region of the HIV-1 HR-1 domain when compared to any sequence of an equal number of amino acids as the number contained in the first polypeptide as aligned by a computer similarity program known in the art and described herein. Preferably, the polypeptide region of the first protein and the second protein includes one or more conserved amino acid residues.

As used herein, an "antibody" includes any reactive fragment or fragments of antibodies such as Fab molecules, Fab proteins, single chain polypeptides, or the multi-functional antibodies having binding affinity for the antigen. The term includes chimeric antibodies, altered antibodies, univalent antibodies, bi-specific antibodies, monoclonal antibodies, polyclonal antibodies, human antibodies, and humanized antibodies. Methods for preparing antibodies are well known in the art.

The symbol

when used as part of a molecular structure refers to a single bond or a trans or cis double bond.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., an amide bond). Polypeptides as described herein include full length proteins (e.g., fully processed proteins) as well as shorter amino acids sequences (e.g., fragments of naturally occurring proteins or synthetic polypeptide fragments).

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Polypeptides

Described herein are modified peptides which exhibit antiviral activity. It is believed that the modified peptides exhibit antiviral activity via their ability to inhibit virus-cell fusion by interfering with viral coat proteins. The modified peptides of the invention may include a stabilized alpha helix heptad repeat domain derived from a virus. Preferably, the alpha helix heptad repeat domain is stabilized with hydrocarbon staples. Suitable viral alpha helix heptad repeat domains can be derived from any virus with an alpha helical domain (e.g., RSV, influenza, parainfluenza, conronavirus, ebolavirus, HIV) that is directly or indirectly involved in cell attachment or entry.

While not limited to any theory of operation, the following model is proposed to explain the potent anti-viral activity of the modified polypeptides described herein. When synthesized as stabilized peptides, the modified polypeptides of the invention are potent inhibitors of viral infection and fusion, likely by virtue of their ability to form complexes with viral glycoproteins and interfere with the fusogenic process; e.g., during the structural transition of the viral protein from the native structure to the fusogenic state. While not being bound by theory, it is believed the modified peptides gain access to their respective binding sites on the viral glycoprotein, and exert a disruptive influence which inhibits fusion of the virus with the cell. The modified polypeptides are particularly useful as a result of their increased stability and efficacy.

In a first aspect, the invention is directed to a modified polypeptide having a stabilized viral alpha helix heptad repeat domain (e.g., HR-1, HR-2, HR-like or HR-analogs) or active fragment thereof. The modified polypeptide may also comprise a chimera of an HR domain. Suitable viral alpha helix heptad repeat domains can be derived from any virus with an alpha helix domain that is directly or indirectly involved in cell attachment or entry.

In another aspect, the invention is directed to a modified polypeptide having a stabilized HIV gp41 heptad repeat domain (e.g., heptad repeat domain 1 or 2 of HIV-1 or HIV-2). The amino acid sequences of heptad repeat-1 and heptad repeat-2 domains are well known in the art and include those represented by SEQ ID NO:2 and SEQ ID NO:1, respectively. In one embodiment, the heptad repeat domain 1 is 30% or more identical to an amino acid sequence of SEQ ID NO:2, SEQ ID NO:3 or SEQ ID NO:14 and forms an alpha helix. Alternatively, the heptad repeat one domain of the modified polypeptide may differ by more than 30% as long as the residues of the interacting face are identical to those of SEQ ID NO:1 or 2 or are conservative substitutions thereof. Methods for identifying the interacting face residues of the heptad repeat are well known in the art and described herein.

In another embodiment, the heptad repeat domain 2 is 30% or more identical to an amino acid sequence of FIG. 4, FIG. 6 or SEQ ID NO:1 and forms an alpha-helix. Alternatively, the heptad repeat two domain of the modified polypeptide may differ by more than 30% as long as the residues of the interacting face are identical to those of SEQ ID NO:1 or 2 or have conservative substitutions thereof. Methods for identifying the interacting face residues of the heptad repeat are well known in the art and described herein.

In one embodiment, the modified polypeptide includes a heptad repeat domain having the formula: a b c de f g, wherein a and d are hydrophobic amino acid residues and b, c, e, f and g are any amino acid. Preferably, the formula is repeated in tandem two or more times.

For example, in a further embodiment the heptad repeat domain of the modified polypeptide has the formula: W(a), b, c, W(d), e, f, g, I(a), b, c, Y(d), e, f, g, I(a), b, c, L(d), e, f, g, S(a), b, c, Q(d), e, f, g, N(a), b, c, E(d), e, f, g, L(a), or conservative amino acid substitutions thereof and wherein the b, c, e, f and g can be any amino acid (e.g., residues 3-38 of SEQ ID NO: 44).

In a further, embodiment the heptad repeat domain of the modified polypeptide has the formula: T(g), W(a), b, c, W(d), D(e), R(f), g, I(a), b, c, Y(d), e, f, g, I(a), b, c, L(d), I(e), f, g, a, Q(b), c, d, Q(e), E(f), K(g), a, E(b), c, d, L(e), f, E(g), L(a), or conservative amino acid substitutions thereof and wherein non-designated amino acids can be any amino acid (e.g., residues 2-38 of SEQ ID NO: 45).

In another embodiment, the modified polypeptide of the invention is has the same amino acid residues, or conservative substitutions thereof, of the interacting face of the amino acid sequence of SEQ ID NO:1-14, FIG. 5 or FIG. 6. The "interacting face" of the alpha helix are those amino acid residues which interact with other amino acid residues in a coiled coil structure. For example, in the HIV gp41 HR-2 domain the interacting face includes the "a" and "d" position amino acids. (See FIGS. 4A and 9), while the interacting face of the HIV gp41 HR-1 domain includes amino acids at positions e, g that interact with HR-2 and a, d that engage in HR1-HR1 interactions (See FIG. 4A). Methods for identifying heptad repeats and the interacting face residues are well known in the art and described herein.

Preferably the alpha helix heptad repeat domain is stabilized with a hydrocarbon staple (e.g., FIG. 10). Hydrocarbon staples suitable for use with any of the modified polypeptides are described herein and in U.S. Publication No. 2005/0250680, which is incorporated by reference in its entirety. Hydrocarbon stapling allows a polypeptide, predisposed to have an alpha-helical secondary structure, to maintain its native alpha-helical conformation and increase its stability and efficacy. In one embodiment, the modified polypeptide has at least 10%, 20%, 30%, 35%, 40%, 45%, 50%, 60%, 70%, 80%, or 90% or more alpha helicity in an aqueous solution as determined by circular dichroism. Assays for determining circular dichroism are known in the art and described herein.

The hydrocarbon stapled polypeptides include a tether (linkage) between two amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, any of the amino acid residues of the modified polypeptides of the invention may be tethered (e.g., cross-linked) in conformity with the above. Suitable tethers are described herein and in U.S. Patent Publication No. 2005/0250680.

In a further embodiment, the hydrocarbon staple(s) is positioned so as to link a first amino acid (i) and a second amino acid (i+3) which is 3 amino acids downstream of the first amino acid. In another embodiment, the hydrocarbon staple links a first amino acid (i) and a second amino acid (i+4) which is 4 amino acids downstream of the first amino acid. In yet another embodiment, the hydrocarbon staple links a first amino acid (i) and a second amino acid (i+7) which is 7 amino acids downstream of the first amino acid.

In yet a further embodiment, the modified polypeptides include a heptad repeat domain with the sequence:

```
                                          (SEQ ID NO: 15)
BTWXEWDXEINNYTSLIHSL, (SEQ ID NO: 16)
BTWBEWDREINNYTSLIHSLIEESQNQQXKNEXELLE, (SEQ ID NO: 17)
BTWBXWDRXINNYTSL, (SEQ ID NO: 18)
BTWBEWDREINNYTSLIHSLIEXSQNXQEKNEQELLE, (SEQ ID NO: 19)
BTWBXWDRXINNYTSLIHSLIEESQNQQEKNEQELLE, (SEQ ID NO: 20)
BTWBXWDRXINNYTSLIHSLIEXSQNXQEKNEQELLE, (SEQ ID NO: 21)
BTWBEWDREINNYTSLIHSLIEESQNQQXKNEXELLE, (SEQ ID NO: 22)
BTWBXWDRXINNYTSLIHSLIEESQNQQXKNEXELLE, (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 26)
BTWBXWDRXINNYTSXIHSXIEESQNQQXKNEXELLE, (SEQ ID NO: 27)
YTSXIHSXIEESQNQQEKNEQELLELDKWASLWNWF, (SEQ ID NO: 28)
YTSLIXSLIXESQNQQEKNEQELLELDKWASLWNWF, (SEQ ID NO: 29)
YTSLIHSLIEXSQNXQEKNEQELLELDKWASLWNWF, (SEQ ID NO: 30)
YTSLIHSLIEESQNQQXKNEXELLELDKWASLWNWF, (SEQ ID NO: 31)
YTSLIHSLIEESQNQQEXNEQXLLELDKWASLWNWF, (SEQ ID NO: 32)
YTSLIHSLIEESQNQQEKNEQXLLEXDKWASLWNWF, (SEQ ID NO: 33)
YTSLIHSLIEESQNQQEKNEQELLELDXWASXWNWF, (SEQ ID NO: 34)
YTSLIHSLIEESQNQQEKNEQELLELDKWXSLWXWF, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF, (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 41)
YTSXIHSXIEESQNQQXKNEXELLELDXWASXWNWF, (SEQ ID NO: 42)
BTWBXWDRXINNYTSLIHSLIEESQNQXEKNXQELLE,
or (SEQ ID NO: 43)
BTWBXWDRXINNYTSLIHSLIEESQNXQEKXEQELLE;
``` wherein X is any amino acid and further identifies the amino acid residues which are linked by a hydrocarbon staple, and B is methionine or norleucine. The modified polypeptides will generally have the structure of Formula (I), (II) or (III), as described herein.

The invention is also, inter alia, directed to modified polypeptides from other viruses with alpha helical domains that are either directly or indirectly involved in the attachment and/or fusion of a virus to a cell. For example, in one aspect the invention is directed to a modified polypeptide having a stabilized viral alpha helix (e.g., heptad repeat domain) that is derived from respiratory syncytial virus. The alpha helix may include any alpha helical domain derived from RSV that is involved in viral infectivity. Suitable RSV alpha helix domains include those which are 30% or more identical to
YTSVITIELSNIKENKCNGTDAKVKLIKQELDKYK-NAVTELQLLMQST (SEQ ID NO:4);
FYDPLVFPSDEFDASISQVNEKINQSLAFIRKSDELL (SEQ ID NO:5);
SGIAVSKVLHLEGEVNKIKNALLSTNKAVVSL-SNGVSVLTSKVLDLKSYINNQ LLPI- (SEQ ID NO: 11) or
PIINYYDPLVFPSDEFDASISQVNEKINQSLAFIRRS-DELLHNVNTGKSTTNIM (SEQ ID NO: 12); and form an alpha-helix.

Alternatively, the heptad repeat analog domain of the modified polypeptide may differ by more than 30% as long as the residues of the interacting face are identical to those of SEQ ID NOs: 4, 5, 11 and 12 or are conservative substitutions thereof. Methods for identifying the interacting face residues of the heptad repeat analogs are well known in the art and described herein.

In yet another aspect, the invention is directed to a modified polypeptide having a stabilized viral alpha helix heptad repeat domain that is derived from a parainfluenza virus. Suitable parainfluenza virus heptad repeat domains include those which are 30% or more identical to ALGVATSAQITAAVALVEAKQARSDIEKLKEAIR (SEQ ID NO:6) and form an alpha-helix. Alternatively, the heptad repeat domain of the modified parainfluenza polypeptide may differ by more than 30% as long as the residues of the interacting face are identical to those of SEQ ID NO: 6 or are conservative substitutions thereof. Methods for identifying the interacting face residues of the heptad repeat are well known in the art and described herein.

In another aspect, the invention is directed to a modified polypeptide having a stabilized viral alpha helix heptad repeat domain derived from a paramyxovirus, orthomyxovirus coronavirus, and a filovirus.

Coronavirus alpha helix heptad repeat domains are known in the art and include those which have an amino acid sequence which are 30% or more identical to NVLYENQKQIANQFNKAISQIQESLTTTSTALG-KLQDVVNQNAQALNTLVKQ LSSNFGAISSV-LNDILSRLDKVEAE (SEQ ID NO:7) or TSPDVDFGDISGINASVVNIQKEIDRLNEVAKNL-NESLIDLQELGKY (SEQ ID NO:8) and form an alpha-helix. Alternatively, the heptad repeat domain of the modified coronavirus polypeptide may differ by more than 30% as long as the residues of the interacting face are identical to those of SEQ ID NOs: 7 and 8 or are conservative substitutions thereof. Methods for identifying the interacting face residues of the heptad repeat are well known in the art and described herein.

Similarly, filovirus alpha helix heptad repeat domains are known in the art and include those that are 30% or more identical to DGLICGLRQLANETTQALQLFLRATTELRTFSILN-RKAIDFLL (SEQ ID NO:9) or DWTKNITDKIDQIIHD-FVDKTLPD (SEQ ID NO:10) and form an alpha-helix. Alternatively, the heptad repeat domain of the modified filovirus polypeptide may differ by more than 30% as long as the residues of the interacting face are identical to those of SEQ ID NO: 10 or are conservative substitutions thereof. Methods for identifying the interacting face residues of the heptad repeat are well known in the art and described herein.

Influenza heptad repeat domains are also known in the art. For example, a heptad repeat domain in Influenza A Virus (strain A/Aichi/2/68) occurs at residues 379-436, 387-453, and 380-456. Similarly, residues 383-471 were shown by Carr and Kim to be an extended coiled coil when under acidic pH (Carr and Kim, 1993, Cell 73: 823-832).

The modified polypeptides of the invention will generally include the structure of Formula (I), (II) or (III) provided below.

Any of the modified polypeptides described herein can be present in a composition (e.g., pharmaceutical composition) or kit. In some embodiments of the invention, the composition or kit comprises two or more modified polypeptides. For example, the composition may include two or more modified polypeptides having a stabilized HIV gp41 heptad repeat domain.

For clarity of discussion, the invention will be further described primarily for HR-1 and HR-2 modified polypeptides of HIV. However, the principles may be analogously applied to other viruses, both enveloped and nonenveloped, and to other non-viral organisms. As used herein the term "heptad repeat" includes HR-2 and HR-1 peptides.

HR-2 and HR-2-Peptides

The modified polypeptides of the invention include the HR-2 peptides (SEQ ID NO:1 and 13) which corresponds to amino acid residues 638 to 673 and 626 and 662 respectively of gp160 from the HIV-1 (SEQ ID NO:13), and has the 36 and 37 amino acid sequences, respectively, of (reading from amino to carboxy terminus):

```
                                     (SEQ ID NO: 1)
YTSLIHSLIEESQNQQEKNEQELLELDKWASLWNWF
and
                                     (SEQ ID NO: 13)
MTWMEWDREINNYTSLIHSLIEESQNQQEKNEQELLE.
```

Other useful HR-2 polypeptides for use with the current invention are described in U.S. Pat. No. 7,273,614, which is incorporated herein by reference in its entirety.

In addition to the use of full-length HR-2 (SEQ ID NO:1 and 13) 36 and 37-mers and the corresponding sequences and variants thereof found in the diversity of HIV-1 strains and mutants, the peptides of the invention may include truncations of the HR-2 (SEQ ID NO: 1 and 13) peptide, gp41 polypeptide sequences that flank the HR-2 domain (ie immediately upstream or downstream sequences), or chimeras which exhibit antifusogenic activity and antiviral activity. Truncations of HR-2 (SEQ ID NO:1 and 13) peptides may comprise peptides of between 3 and 36 amino acid residues, as shown in FIGS. 5 and 6. Peptide sequences in this figure are listed from amino (left) to carboxy (right) terminus.

The modified peptides of the invention also include HR-2-like peptides. "HR-2-like" or "heptad repeat-like", as used herein, refers to full-length and truncated and chimeric HR-2 polypeptides which contain one or more amino acid substitutions, insertions and/or deletions as well as peptide sequences identified or recognized by homology searching. Representative HR-2 like polypeptides include those illustrated in FIG. 5 or FIG. 6. The modified HR-2-like peptides of the invention may exhibit antifusogenic or antiviral activity. In one embodiment, the heptad repeat domain 2 is 30% or more identical to an amino acid sequence of FIG. 5, FIG. 6, SEQ ID NO:1 or SEQ ID NO:13 and form an alpha-helix. Alternatively, the heptad repeat domain 2 of the modified polypeptide may differ by more than 30% as long as the residues of the interacting face are identical to those of FIG. 5, FIG. 6, SEQ ID NO:1 or SEQ ID NO:13 or are conservative substitutions thereof. Methods for identifying the interacting face residues of the heptad repeat are well known in the art and described herein.

HIV-1 and HIV-2 enveloped proteins are structurally distinct, but there exists a striking amino acid conservation within the HR-2 regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the HR-2 peptides of the invention. Utilizing the HR-2 and HR-2 analog sequences described herein, the skilled artisan can readily compile HR-2 consensus sequences and ascertain from these, conserved amino acid residues which would represent preferred amino acid substitutions.

The amino acid substitutions may be of a conserved or non-conserved nature. Conserved amino acid substitutions consist of replacing one or more amino acids of the HR-2 (SEQ ID NO:1 or 13) peptide sequence with amino acids of similar charge, size, and/or hydrophobicity characteristics, such as, for example, a glutamic acid (E) to aspartic acid (D), aspartic acid (D) to asparagine (N), and glutamic acid (E) to glutamine (Q) amino acid substitution. Non-conserved substitutions consist of replacing one or more amino acids of the HR-2 peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues. The insertions may be made at the carboxy or amino terminal end of the full length or truncated HR-2 peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into the full-length (SEQ ID NO:1 or 13) or truncated HR-2 polypeptides as long as such insertions result in modified peptides that exhibit antifusogenic or antiviral activity.

Preferred amino or carboxy terminal insertions are peptides ranging from about 2 to about 50 amino acid residues in length, corresponding to gp41 protein regions either amino to or carboxy to the actual HR-2 gp41 amino acid sequence, respectively. Thus, a preferred amino terminal or carboxy terminal amino acid insertion would contain gp41 amino acid sequences found immediately amino to or carboxy to the HR-2 region of the gp41 protein.

Deletions of full-length (SEQ ID NO:1 or 13) or truncated HR-2 polypeptides are also within the scope of the invention. Such deletions consist of the removal of one or more amino acids from the HR-2 or HR-2-like peptide sequence, with the lower limit length of the resulting peptide sequence being 4 to 6 amino acids. Such deletions may involve a single contiguous or greater than one discrete portion of the peptide sequences. One or more such deletions may be introduced into full-length (SEQ ID NO: 1 or 13) or truncated HR-2 polypeptides, as long as such deletions result in peptides which may still exhibit antifusogenic or antiviral activity.

HR-1 and HR-1-Peptides

Further, the modified peptides of the invention include peptides having amino acid sequences corresponding to HR-1 analogs. HR-1 includes 38- and 51-amino acid peptides which exhibits potent antiviral activity, and corresponds to residues 553 to 590 and 542-592, respectively, of HIV-1 transmembrane (TM) gp41 protein, as shown below:

```
                                        (SEQ ID NO: 2)
NNLLRAIEAQQHLLQLTVWGIKQLQARILAVERYLQDQ
or
                                        (SEQ ID NO: 14)
RQLLSGIVQQQ NNLLRAIEAQQHLLQLTVWGIKQLQARILAVERYLQ
DQQL.
```

In addition to the full-length HR-1 38-mer, the modified peptides of the invention include truncations of the HR-1 peptide which exhibit antifusogenic activity or antiviral activity. Truncations of HR-1 peptides can be made in a similar manner as those exemplified for the HR-2 peptides in FIG. 5 and FIG. 6.

The modified peptides of the invention also include HR-1-like peptides. "HR-1-like" or "heptad-repeat like", as used herein, refers to full-length and truncated HR-1 polypeptides which contain one or more amino acid substitutions, insertions and/or deletions and exhibiting antifusogenic or antiviral activity. In one embodiment, the heptad repeat domain 1 is 30% or more identical to an amino acid sequence of SEQ ID NO:2, SEQ ID NO:3 or SEQ ID NO:14 and form an alpha-helix. Alternatively, the heptad repeat domain 1 of the modified polypeptide may differ by more than 30% as long as the residues of the interacting face are identical to those of SEQ ID NOs 2, 3 or 14 or are conservative substitutions thereof. Methods for identifying the interacting face residues of the heptad repeat are well known in the art and described herein.

HIV-1 and HIV-2 enveloped proteins are structurally distinct, but there exists a striking amino acid conservation within the HR-1-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the HR-1 peptides of the invention. Utilizing the HR-1 and HR-1 analog sequences described herein, the skilled artisan can readily compile HR-1 consensus sequences and ascertain from these, conserved amino acid residues which would represent preferred amino acid substitutions.

The amino acid substitutions may be of a conserved or non-conserved nature. Conserved amino acid substitutions consist of replacing one or more amino acids of the HR-1 peptide sequence with amino acids of similar charge, size, and/or hydrophobicity characteristics, such as, for example, a glutamic acid (E) to aspartic acid (D), aspartic acid (D) to asparagine (N), and glutamic acid (E) to glutamine (Q) amino acid substitution. Non-conserved substitutions consist of replacing one or more amino acids of the HR-1 peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues. The insertions may be made at the carboxy or amino terminal end of the full-length or truncated HR-1 peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into full-length or truncated HR-1 polypeptides, as long as such insertions result in modified peptides which may still exhibit antifusogenic or antiviral activity.

Preferred amino or carboxy terminal insertions are peptides ranging from about 2 to about 50 amino acid residues in length, corresponding to gp41 protein regions either amino to or carboxy to the actual HR-1 gp41 amino acid sequence, respectively. Thus, a preferred amino terminal or carboxy terminal amino acid insertion would contain gp41 amino acid sequences found immediately amino to or carboxy to the HR-1 region of the gp41 protein.

Deletions of full-length or truncated HR-1 polypeptides are also within the scope of the invention. Such deletions consist of the removal of one or more amino acids from the HR-1 or HR-1-like peptide sequence, with the lower limit length of the resulting peptide sequence being 4 to 6 amino acids. Such deletions may involve a single contiguous or greater than one discrete portion of the peptide sequences. One or more such deletions may be introduced into full-length or truncated HR-1 polypeptides, as long as such deletions result in peptides which may still exhibit antifusogenic or antiviral activity HR-1 and HR-2 Analogs Peptides corresponding to analogs of the full-length and truncated HR-1 and HR-2 polypeptides, described, above, may be found in other viruses. The term "HR-1 and HR-2-analogs", as used herein, refers to a peptide which is recognized or identified as having a heptad repeat-analog domain in a non-HIV virus. Methods for identifying heptad repeat-analog polypeptides are known in the art, for example, bioinformatics programs based on pairwise residue correlations (e.g., on the world wide web at: ch.embnet.org/software/COILS_form.html), which have the ability to recognize coiled coils from protein sequences and model their structures (See Lupas, A., et al. Science 1991. 252(5009); p. 1162-1164, which is herein incorporated by reference). Further, such modified peptides exhibit antifusogenic or antiviral activity.

Such HR-2 and HR-1 analogs may, for example, correspond to peptide sequences present in transmembrane proteins of other enveloped viruses. Such peptides may exhibit antifusogenic activity or antiviral activity.

HR-2 analogs are peptides whose amino acid sequences are comprised of the amino acid sequences of peptide regions of, for example, other viruses that correspond to the gp41 peptide region from which HR-2 (SEQ ID NO: 1) was derived. Such viruses may include, but are not limited to, other HIV-1 isolates, HIV-2 isolates, SIV isolates, influenza, parainfluenza virus, coronavirus, RSV, etc.

HR-1 analogs are peptides whose amino acid sequences are comprised of the amino acid sequences of peptide regions of, for example, other viruses that correspond to the gp41 peptide region from which HR-1 (SEQ ID NO: 2) was derived. Such viruses may include, but are not limited to, other HIV-1 isolates HIV-2 isolates, SIV isolates, parainfluenza virus, coronavirus, RSV, etc.

HR-1 and HR-2 analogs or other heptad repeat polypeptides include peptides whose amino acid sequences are comprised of the amino acid sequences of peptide regions of, for example, other viruses that correspond to the gp41 peptide region from which HR-1 (SEQ ID NO: 2 or SEQ ID NO:3) and HR-2 (SEQ ID NO:1) were derived. These polypeptides include:

RSV heptad repeat domains which are 30% or more identical to (SEQ ID NO:4), (SEQ ID NO:5), (SEQ ID NO: 11), or (SEQ ID NO: 12) and form an alpha-helix.

Parainfluenza virus heptad repeat domains which are 30% or more identical to (SEQ ID NO:6) and form an alpha-helix.

Coronavirus alpha helix heptad repeat domains which are 30% or more identical to (SEQ ID NO:7) or (SEQ ID NO:8) and form an alpha-helix.

Filovirus alpha helix heptad repeat domains which are 30% or more identical to (SEQ ID NO:9) or (SEQ ID NO:10) and form an alpha-helix.

The modified polypeptides of the invention also contemplate the use of influenza virus heptad repeat domains.

Alternatively, the heptad repeat domains of the modified polypeptides may differ by more than 30% as long as the residues of the interacting face are identical to those of the interacting face of the reference sequence or are conservative substitutions thereof. Methods for identifying the interacting face residues of the heptad repeat are well known in the art and described herein.

Heptad repeats or heptad repeat-analogs are recognized or identified, for example, by utilizing computer-assisted search strategies known in the art. For example, bioinformatics programs based on pairwise residue correlations (e.g., on the world wide web at: ch.embnet.org/software/COILS_form.html), which have the ability to recognize coiled coils from protein sequences and model their structures (See Lupas, A., et al. Science 1991. 252(5009); p. 1162-1164, and U.S. Pat. No. 7,273,614 both of which are herein incorporated by reference in its entirety. The search strategy can identify additional peptide regions which are predicted to have structural and/or amino acid sequence features similar to those of HR-1 and/or HR-2.

Stabilization of Heptad Repeat Polypeptides

The modified polypeptides of the present invention have stabilized (e.g., cross-linked) alpha helical domains. Preferable the polypeptides are hydrocarbon-stapled. Hydrocarbon stapling is described in U.S. Patent Publication No. 2005/0250680, which is herein incorporated by reference in its entirety.

The peptide α-helix participates in critically important protein interactions by presenting specific amino acid residues in an ordered and precise arrangement over a relatively large contact surface area (Chittenden, T., et al., *Embo Journal,* 1995. 14(22): p. 5589-5596; Kussie, P. H., et al. Science, 1996. 274(5289): p. 948-953; Ellenberger, T. E., et al., *Cell,* 1992. 71(7): p. 1223-1237). Alpha-helical domains are frequently stabilized by scaffold sequences in the remainder of the protein, which facilitate the preorganization of α-helical structure. When taken out of context, α-helical peptide motifs can unfold, leading to loss of biological activity. Critical challenges is developing α-helical peptides include maintaining their natural α-helical structure and preparing peptides that can resist proteolytic, acid and thermal degradation, and thereby remain intact in vivo.

Hydrocarbon stapling, refers to a process for stably cross-linking a polypeptide via at least two amino acids that helps to conformationally bestow the native secondary structure of that polypeptide. Hydrocarbon stapling allows a polypeptide, predisposed to have an alpha-helical secondary structure, to maintain its native alpha-helical conformation. This secondary structure increases resistance of the polypeptide to proteolytic cleavage and heat, and also may increase hydrophobicity. Accordingly, the hydrocarbon stapled (cross-linked) polypeptides described herein have improved biological activity relative to a corresponding non-hydrocarbon stapled (uncrosslinked) polypeptide. For example the cross-linked polypeptide can include an alpha-helical domain of an HIV polypeptide (e.g., HR-1/HR-2 domain), which can interfere with HIV attachment, fusion with, and infection of a cell. In some instances, the cross-linked polypeptide can be used to inhibit virus entry into a cell. The cross-linked polypeptides described herein can be used therapeutically, e.g., to treat HIV.

The hydrocarbon stapled polypeptides include a tether (linkage) between two amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) has also been achieved, compounding the benefits of individual stapled adducts (e g improved helicity and activity; improved helicity and thermal stability; improved helicity and acid stability). Thus, the invention encompasses the incorporation of more than one crosslink within the polypeptide sequence to either further stabilize the sequence or facilitate the structural stabilization, proteolytic resistance, thermal stability, acid stability, and biological activity enhancement of longer polypeptide stretches.

In one embodiment, the modified polypeptides of the invention have the formula (I),

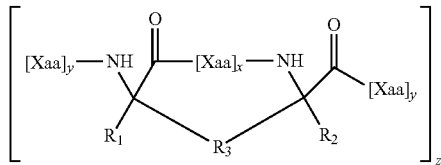

wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4\text{-K-}R_4]_n$; each of which is substituted with 0-6 $R_5$;

$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

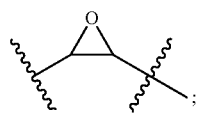 [SMILES: *C1OC1*]

;

$R_6$ is H, alkyl, or a therapeutic agent;
n is an integer from 1-4;
x is an integer from 2-10;
each y is independently an integer from 0-100;

z is an integer from 1-10 (e.g., 1, 2, 3, 4, 5, 6, 7, 8, 9, 10); and each Xaa is independently an amino acid. The modified polypeptides may include an amino acid sequence which forms an alpha-helix and is 30% or more identical to an amino acid sequence of SEQ ID NO:1-14, FIG. 5, FIG. 6,

```
                                        (SEQ ID NO: 15)
BTWXEWDXEINNYTSLIHSL, (SEQ ID NO: 16)
BTWBEWDREINNYTSLIHSLIEESQNQQXKNEXELLE, (SEQ ID NO: 17)
BTWBXWDRXINNYTSL, (SEQ ID NO: 18)
BTWBEWDREINNYTSLIHSLIEXSQNXQEKNEQELLE, (SEQ ID NO: 19)
BTWBXWDRXINNYTSLIHSLIEESQNQQEKNEQELLE, (SEQ ID NO: 20)
BTWBXWDRXINNYTSLIHSLIEXSQNXQEKNEQELLE, (SEQ ID NO: 21)
BTWBEWDREINNYTSLIHSLIEESQNQQXKNEXELLE, (SEQ ID NO: 22)
BTWBXWDRXINNYTSLIHSLIEESQNQQXKNEXELLE,
```

-continued

```
                                        (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 26)
BTWBXWDRXINNYTSXIHSXIEESQNQQXKNEXELLE, (SEQ ID NO: 27)
YTSXIHSXIEESQNQQEKNEQELLELDKWASLWNWF, (SEQ ID NO: 28)
YTSLIXSLIXESQNQQEKNEQELLELDKWASLWNWF, (SEQ ID NO: 29)
YTSLIHSLIEXSQNXQEKNEQELLELDKWASLWNWF, (SEQ ID NO: 30)
YTSLIHSLIEESQNQQXKNEXELLELDKWASLWNWF, (SEQ ID NO: 31)
YTSLIHSLIEESQNQQEXNEQXLLELDKWASLWNWF, (SEQ ID NO: 32)
YTSLIHSLIEESQNQQEKNEQXLLEXDKWASLWNWF, (SEQ ID NO: 33)
YTSLIHSLIEESQNQQEKNEQELLELDXWASXWNWF, (SEQ ID NO: 34)
YTSLIHSLIEESQNQQEKNEQELLELDKWXSLWXWF, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF, (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 41)
YTSXIHSXIEESQNQQXKNEXELLELDXWASXWNWF, (SEQ ID NO: 42)
BTWBXWDRXINNYTSLIHSLIEESQNQXEKNXQELLE,
or (SEQ ID NO: 43)
BTWBXWDRXINNYTSLIHSLIEESQNXQEKXEQELLE;
``` wherein X is any amino acid and further identifies the amino acid residues which are linked by a hydrocarbon staple, and B is methionine or norleucine.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is —$CH_2$—$CH_2$—$CH_2$—$CH$=$CH$—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

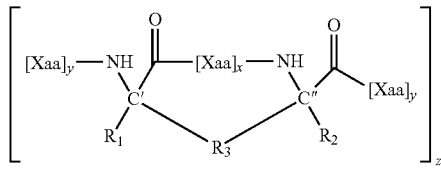

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4$-$K$-$R_4]_n$; and R4 is a straight chain alkyl, alkenyl, or alkynyl.

In some embodiments the modified polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of a heptad repeat or heptad repeat like domain, e.g., a HIV-1 HR-1 or HR-2 domain. Each [Xaa]y is a peptide that can independently comprise at least 5, 6, 7, 8, 9, 10, 11, 12, 13, 14, 15, 16, 17, 18, 19, 20, 25 or more contiguous amino acids of a heptad repeat or heptad repeat like domain, e.g., a HIV-1 HR-1 or HR-2 domain, e.g., a polypeptide depicted in any of FIGS. 5 and 6. [Xaa]$_x$ is a peptide that can comprise 3 or 6 contiguous amino acids of acids of a heptad repeat or heptad repeat like domain, e.g., a HIV-1 HR-1 domain or HR-2, e.g., a polypeptide having the amino acid sequence of SEQ ID NO:1-14 or FIG. 5 or 6.

The modified polypeptide can comprise 3, 4, 5, 6, 7, 8, 9, 10, 11, 12, 13, 14, 15, 16, 17, 18, 19, 20, 25, 30, 35, 40, 45, 50 contiguous amino acids of acids of a heptad repeat or heptad repeat like domain, e.g., a HIV-1 HR-1 domain or HR-2, e.g., a polypeptide having the amino acid sequence of SEQ ID NO:1-14 or FIG. 5 or 6, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as

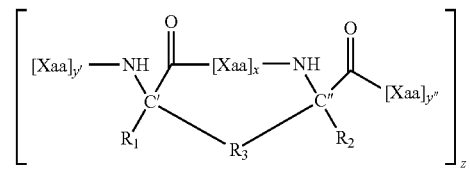

[Xaa]$_{y'}$ and [Xaa]$_{y''}$ can each comprise contiguous polypeptide sequences from the same or different heptad repeat or heptad repeat like domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a heptad repeat or heptad repeat like domain, e.g., a HIV-1 HR-1 domain or HR-2, e.g., a polypeptide having the amino acid sequence of SEQ ID NO:1-14 or FIG. 5 or 6, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the modified polypeptides of the invention have the formula (II),

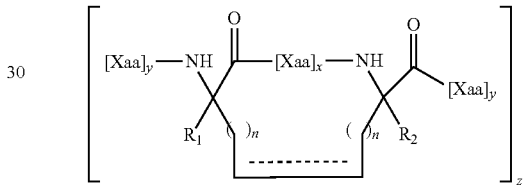

wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
each y is independently an integer from 0-100;
z is an integer from 1-10 (e.g., 1, 2, 3, 4, 5, 6, 7, 8, 9, 10);
each Xaa is independently an amino acid.

The modified polypeptide forms an alpha-helix and can have an amino acid sequence which is 30% or more identical to an amino acid sequence of SEQ ID NO:1-14, FIG. 5, FIG. 6, the modified polypeptides include a heptad repeat domain with the sequence:

```
                                        (SEQ ID NO: 15)
BTWXEWDXEINNYTSLIHSL, (SEQ ID NO: 16)
BTWBEWDREINNYTSLIHSLIEESQNQQXKNEXELLE, (SEQ ID NO: 17)
BTWBXWDRXINNYTSL, (SEQ ID NO: 18)
BTWBEWDREINNYTSLIHSLIEXSQNXQEKNEQELLE, (SEQ ID NO: 19)
BTWBXWDRXINNYTSLIHSLIEESQNQQEKNEQELLE, (SEQ ID NO: 20)
BTWBXWDRXINNYTSLIHSLIEXSQNXQEKNEQELLE,
```

-continued

```
(SEQ ID NO: 21)
BTWBEWDREINNYTSLIHSLIEESQNQQXKNEXELLE, (SEQ ID NO: 22)
BTWBXWDRXINNYTSLIHSLIEESQNQQXKNEXELLE, (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 26)
BTWBXWDRXINNYTSXIHSXIEESQNQQXKNEXELLE, (SEQ ID NO: 27)
YTSXIHSXIEESQNQQEKNEQELLELDKWASLWNWF, (SEQ ID NO: 28)
YTSLIXSLIXESQNQQEKNEQELLELDKWASLWNWF, (SEQ ID NO: 29)
YTSLIHSLIEXSQNXQEKNEQELLELDKWASLWNWF, (SEQ ID NO: 30)
YTSLIHSLIEESQNQQXKNEXELLELDKWASLWNWF, (SEQ ID NO: 31)
YTSLIHSLIEESQNQQEXNEQXLLELDKWASLWNWF, (SEQ ID NO: 32)
YTSLIHSLIEESQNQQEKNEQXLLEXDKWASLWNWF, (SEQ ID NO: 33)
YTSLIHSLIEESQNQQEKNEQELLELDXWASXWNWF, (SEQ ID NO: 34)
YTSLIHSLIEESQNQQEKNEQELLELDKWXSLWXWF, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF, (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 41)
YTSXIHSXIEESQNQQXKNEXELLELDXWASXWNWF, (SEQ ID NO: 42)
BTWBXWDRXINNYTSLIHSLIEESQNQXEKNXQELLE,
or (SEQ ID NO: 43)
BTWBXWDRXINNYTSLIHSLIEESQNXQEKXEQELLE;
``` wherein X is any amino acid and further identifies the amino acid residues which are linked by a hydrocarbon staple, and B is methionine or norleucine.

In still another embodiment, the modified polypeptides of the invention have the formula (III), 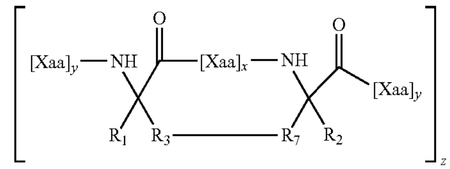 wherein;

each $R_1$ and $R_2$ are independently H, alkyl, alkenyl, alkynyl, arylalkyl, cycloalkylalkyl, heteroarylalkyl, or heterocyclylalkyl;

$R_3$ is alkyl, alkenyl, alkynyl; $[R_4\text{-K-}R_4]_n$ or a naturally occurring amino acid side chain; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or 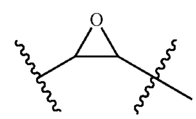 [SMILES: *C1OC1*] $R_6$ is H, alkyl, or a therapeutic agent;

$R_7$ is alkyl, alkenyl, alkynyl; $[R_4\text{-K-}R_4]_n$ or an naturally occurring amino acid side chain; each of which is substituted with 0-6 $R_5$;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid;

The polypeptide forms and alpha-helix and includes an amino acid sequence which is about 30% or more identical to an amino acid sequence of SEQ ID NO:1-14, FIG. 5, FIG. 6 or the modified polypeptides include a heptad repeat domain with the sequence:

```
(SEQ ID NO: 15)
BTWXEWDXEINNYTSLIHSL, (SEQ ID NO: 16)
BTWBEWDREINNYTSLIHSLIEESQNQQXKNEXELLE, (SEQ ID NO: 17)
BTWBXWDRXINNYTSL, (SEQ ID NO: 18)
BTWBEWDREINNYTSLIHSLIEXSQNXQEKNEQELLE, (SEQ ID NO: 19)
BTWBXWDRXINNYTSLIHSLIEESQNQQEKNEQELLE, (SEQ ID NO: 20)
BTWBXWDRXINNYTSLIHSLIEXSQNXQEKNEQELLE, (SEQ ID NO: 21)
BTWBEWDREINNYTSLIHSLIEESQNQQXKNEXELLE, (SEQ ID NO: 22)
BTWBXWDRXINNYTSLIHSLIEESQNQQXKNEXELLE,
```

-continued (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 26)
BTWBXWDRXINNYTSXIHSXIEESQNQQXKNEXELLE, (SEQ ID NO: 27)
YTSXIHSXIEESQNQQEKNEQELLELDKWASLWNWF, (SEQ ID NO: 28)
YTSLIXSLIXESQNQQEKNEQELLELDKWASLWNWF, (SEQ ID NO: 29)
YTSLIHSLIEXSQNXQEKNEQELLELDKWASLWNWF, (SEQ ID NO: 30)
YTSLIHSLIEESQNQQXKNEXELLELDKWASLWNWF, (SEQ ID NO: 31)
YTSLIHSLIEESQNQQEXNEQXLLELDKWASLWNWF, (SEQ ID NO: 32)
YTSLIHSLIEESQNQQEKNEQXLLEXDKWASLWNWF, (SEQ ID NO: 33)
YTSLIHSLIEESQNQQEKNEQELLELDXWASXWNWF, (SEQ ID NO: 34)
YTSLIHSLIEESQNQQEKNEQELLELDKWXSLWXWF, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF, (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 41)
YTSXIHSXIEESQNQQXKNEXELLELDXWASXWNWF, (SEQ ID NO: 42)
BTWBXWDRXINNYTSLIHSLIEESQNQXEKNXQELLE,
or (SEQ ID NO: 43)
BTWBXWDRXINNYTSLIHSLIEESQNXQEKXEQELLE;

wherein X is any amino acid and further identifies the amino acid residues which are linked by a hydrocarbon staple, and B is methionine or norleucine.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Synthesis of Peptides

The peptides of this invention can be made by chemical synthesis methods, which are well known to the ordinarily skilled artisan and described herein. See, for example, Fields et al., Chapter 3 in *Synthetic Peptides: A User's Guide*, ed. Grant, W. H. Freeman & Co., New York, N.Y., 1992, p. 77. Hence, peptides can be synthesized using the automated Merrifield techniques of solid phase synthesis with the alpha-$NH_2$ protected by either t-Boc or F-moc chemistry using side chain protected amino acids on, for example, an Applied Biosystems Peptide Synthesizer Model 430A or 431 or the AAPPTEC multichannel synthesizer APEX 396.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell.

Furthermore, the host cell is engineered so as to be able to incorporate the non-natural amino acids for the hydrocarbon staple. The peptide is then expressed under suitable conditions appropriate for the selected expression system and host. See Liu et al. *Proc. Nat. Acad. Sci (USA)*, 94:10092-10097 (1997). The peptide is purified and characterized by standard methods.

The peptides can be made in a high-throughput, combinatorial fashion, e.g., using a high-throughput polychannel combinatorial synthesizer available from Advanced Chemtech.

Assaying Anti-viral Activity

Described herein, are methods for evaluating the ability of a compound, such as the peptides of the invention, to inhibit membrane fusion and/or exhibit anti-viral activity both in vitro and in vivo. Specifically, such assays are described below and in Examples 4 and 5. Additional assays for evaluating anti-vial activity are well known to those with ordinary skill in the art.

The antiviral activity exhibited by the peptides of the invention may be measured, for example, by easily performed in vitro assays, such as those described herein and known by those of ordinary skill in the art, which can test the peptides' ability to inhibit syncytia formation, or their ability to inhibit infection by cell-free virus (Madani, N., et al., *Journal of Virology*, 2007. 81(2): p. 532-538; Si, Z. H., M. Cayabyab, and J. Sodroski, *Journal of Virology*, 2001. 75(9): p. 4208-4218; Si, Z. H., et al., *PNAS USA*, 2004. 101(14): p. 5036-5041).

Using these assays, such parameters as the relative antiviral activity of the peptides exhibit against a given strain of virus and/or the strain specific inhibitory activity of the peptide can be determined.

Assays to test a peptide's antiviral capabilities are contemplated with the present invention. Taking HIV as an example, a reverse transcriptase (RT) assay may be utilized to test the peptides' ability to inhibit infection of CD-4+ cells by cell-free HIV. Such an assay may comprise culturing an appropriate concentration (i.e., Tissue Culture Infectious Dose 50) of virus and CD-4+ cells in the presence of the peptide to be tested. Culture conditions well known to those in the art are used. A range of peptide concentrations may be used, in addition to a control culture wherein no peptide has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, J. Virol. 38:239-248) and/or Willey et al. (Willey, R. et al., 1988, J. Virol. 62:139-147). These references are incorporated herein by reference in their entirety.

Standard methods which are well-known to those of skill in the art may be utilized for assaying non-retroviral activity. See, for example, Pringle et al. (Pringle, C. R. et al., 1985, J. Medical Virology 17:377-386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in their entirety.

It is known that HIV positive patients who respond to initial treatment with enfuvirtide, may ultimately develop a viral rebound that typically occurs within a maximum of 80 weeks. Resistance to enfuvirtide derives from mutations within the HR-1 region of gp41, although some genetic changes are found in the HR-2 domain (Xu, L., et al., *Antimicrobial Agents and Chemotherapy*, 2005. 49(3): p. 1113-1119; Perez-Alvarez, L., et al. *Journal of Medical Virology*, 2006. 78(2): p. 141-147). These mutations, such as I37V, V38A/E/M, Q39R, Q40H, N42T/Q/H, N43D/Q, are only found in enfuvirtide-experienced patients (Poveda, E., et al., *Journal of Medical Virology*, 2004. 74(1): p. 21-28; Melby, T., et al., *Aids Research and Human Retroviruses*, 2006. 22(5): p. 375-385; Sista, P. R., et al., *Aids*, 2004. 18(13): p. 1787-1794; Wei, X. P., et al., *Antimicrobial Agents and Chemotherapy*, 2002. 46(6): p. 1896-1905).

Modified polypeptides of the invention can be developed which are able to inhibit these enfuvirtide resistant HIV strains. One suitable method for assessing the ability of the modified polypeptides to treat these enfuvirtide resistant HIV strains is a five-helix bundle assay as described in Root, M. J., M. S. Kay, and P. S. Kim, *Science*, 2001. 291(5505): p. 884-888.

Briefly, the five-helix bundle assay would include polypeptides that incorporate resistance mutations. FITC-labeled SAH-gp41 compounds can then be screened against these mutant five-helix bundle proteins to determine if any native SAH-gp41 compounds retain activity despite HR domain mutations. The FITC labeled mutants SAH-gp41 (mSAH-gp41) compounds can be screened for binding affinity to mutant five-helix bundle proteins and for suppression of HIV infectivity using primary resistance strains.

In another aspect, the modified polypeptides of the invention can be used to monitor the evolution of resistance in HIV isolates. To explore the evolution of potential resistance to SAH-gp41 compounds, HIV strains can be incubated in the presence of increasing concentrations of lead SAH-gp41 compounds in a cell culture. Resistant strains can be genotyped to monitor the evolution of resistance. (See Dwyer et al. *Proc. Natl. Acad. Sci.*, 104:12772 (2007)). Because resistance to one modified polypeptide of the invention may not affect susceptibility to other variants, (Ray, N., et al., *Journal of Virology*, 2007. 81(7): p. 3240-3250) it is contemplated that treatment may include a combination of different SAH-gp41 polypeptides that are able to treat resistant strains of HIV.

In vivo assays may also be utilized to test, for example, the antiviral activity of the peptides of the invention. To test for anti-HIV activity, for example, the in vivo model described in Barnett et al. (Barnett, S. W. et al., 1994, Science 266:642-646) may be used.

Additionally, anti-RSV activity can be assayed in vitro using the RSV plaque assay and in vivo via well known mouse models (Kong et al., *Virology J.* 2(1):3 (2005). For example, RSV can be administered intranasally to mice of various inbred strains. Virus replicates in lungs of all strains, but the highest titers are obtained in P/N, C57L/N and DBA/2N mice. Infection of BALB/c mice produces an asymptomatic bronchiolitis characterized by lymphocytic infiltrates and pulmonary virus titers of 104 to $10^5$ pfu/g of lung tissue (Taylor, G. et al., 1984, *Infect. Immun.* 43:649-655). Cotton rat models of RSV are also well known. Virus replicates to high titer in the nose and lungs of the cotton rat but produces few if any signs of inflammation. Additional assays for evaluating the effectiveness of the modified viral polypeptides are well known to those of ordinary skill in the art.

Pharmaceutical Compositions and Routes of Administration

As used herein, the compounds of this invention (e.g., the modified polypeptides described herein), are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_{4+}$ salts. This invention also envisions the quaternization of any basic nitrogen-containing groups of the compounds disclosed herein. Water or oil-soluble or dispersible products may be obtained by such quaternization.

The compounds of the invention can, for example, be administered by injection, intravenously, intraarterially, subdermally, intraperitoneally, intramuscularly, or subcutaneously; or orally, buccally, nasally, transmucosally, intravaginally, cervically, topically, in an ophthalmic preparation, or by inhalation, with a dosage ranging from about 0.001 to about 100 mg/kg of body weight, or according to the requirements of the particular drug and more preferably from 0.5-10 mg/kg of body weight. The methods herein contemplate administration of an effective amount of compound or compound composition to achieve the desired or stated effect. Typically, the pharmaceutical compositions of this invention will be administered from about 1 to about 6 times per day or alternatively, as a continuous infusion, or for example as an intravaginal foam or formulated for a cervical ring if used singly or in combination with a contraceptive. Such administration can be used as a chronic or acute therapy. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition or prevention of infection, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms (e.g. increase in HIV viral load).

Pharmaceutical compositions of this invention comprise a compounds of the invention or a pharmaceutically acceptable salt thereof; an additional agent including for example, morphine or codeine; and any pharmaceutically acceptable carrier, adjuvant or vehicle. Alternate compositions of this invention comprise a compound of the invention or a pharmaceutically acceptable salt thereof; and a pharmaceutically acceptable carrier, adjuvant or vehicle. The compositions delineated herein include the compounds of the invention delineated herein, as well as additional therapeutic agents if present, in amounts effective for achieving a modulation of disease or disease symptoms, including HIV mediated disorders or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α.-tocopherol polyethyleneglycol 1000 succinate, surfactants used in pharmaceutical dosage forms such as Tween® or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, may also be advantageously used to enhance delivery of compounds of the formulae described herein.

The pharmaceutical compositions of this invention may be administered enterally for example by oral administration, parenterally, by inhalation spray, topically, rectally, nasally, buccally, vaginally or via an implanted reservoir, preferably by oral or vaginal administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases, or buffers to enhance the stability of the formulated compound or its delivery form. The term parenteral as used herein includes subcutaneous, intracutaneous, intravenous, intramuscular, intraarticular, intraarterial, intrasynovial, intrastemal, intrathecal, intralesional, and intracranial injection or infusion techniques.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the invention may be administered topically or intravaginally. The pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. In still another embodiment, the pharmaceutical composition is formulated as a vaginal ring. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention. In one embodiment, the compound of the invention is administered vaginally as a prophylactic treatment for a sexually transmitted disease, e.g., HIV.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

With respect to HIV, peptides of the invention may be used as therapeutics in the treatment of HIV infection and/or AIDS. In addition, the peptides may be used as prophylactic measures in previously uninfected individuals after acute exposure to an HIV virus (e.g. post-exposure prophylaxis). Examples of such prophylactic use of the peptides may include, but are not limited to, prevention of virus transmission from mother to infant and other settings where the likelihood of HIV transmission exists, such as, for example, sexual transmission or accidents in health care settings wherein workers are exposed to HIV-containing blood products.

Effective dosages of the peptides of the invention to be administered may be determined through procedures well known to those in the art which address such parameters as biological half-life, bioavailability, and toxicity.

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of the fusogenic event, such as a half-maximal inhibition of viral infection relative to the amount of the event in the absence of the test compound) as determined in cell culture. Such information can be used to more accurately determine useful doses in humans. Levels in plasma may be measured, for example, by high performance liquid chromatography (HPLC) or mass spectrometry (MS).

Prophylactic Vaccine

The peptides of the invention may, further, serve the role of a prophylactic vaccine, wherein the host raises antibodies against the peptides of the invention, which then serve to neutralize a virus (e.g., HIV, RSV, influenza, parainfluenza, coronavirus, ebolavirus) by, for example, inhibiting further infection. Administration of the peptides of the invention as a prophylactic vaccine, therefore, would comprise administering to a host a concentration of peptides effective in raising an immune response which is sufficient to neutralize the virus, by, for example, inhibiting virus ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and *Corynebacterium parvum*. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention may be administered to a host so that no uninfected cells become infected by the virus. The exact concentration of such antibodies will vary according to each specific antibody preparation, but may be determined using standard techniques well known to those of ordinary skill in the art. Administration of the antibodies may be accomplished using a variety of techniques, including, but not limited to those described in this section.

In one aspect, the invention is directed to a method of generating an antibody to a modified polypeptide. The method includes administering a modified polypeptide(s) of the invention to a subject so as to generate an antibody to the modified polypeptide.

In yet another aspect, the invention is directed to an antibody that specifically binds a modified polypeptide, wherein the modified polypeptide has an amino acid sequence of any of the sequences of FIG. 5, 6, or the modified polypeptides include a heptad repeat domain with the sequence:

```
                                    (SEQ ID NO: 15)
BTWXEWDXEINNYTSLIHSL, (SEQ ID NO: 16)
BTWBEWDREINNYTSLIHSLIEESQNQQXKNEXELLE, (SEQ ID NO: 17)
BTWBXWDRXINNYTSL, (SEQ ID NO: 18)
BTWBEWDREINNYTSLIHSLIEXSQNXQEKNEQELLE, (SEQ ID NO: 19)
BTWBXWDRXINNYTSLIHSLIEESQNQQEKNEQELLE, (SEQ ID NO: 20)
BTWBXWDRXINNYTSLIHSLIEXSQNXQEKNEQELLE, (SEQ ID NO: 21)
BTWBEWDREINNYTSLIHSLIEESQNQQXKNEXELLE, (SEQ ID NO: 22)
BTWBXWDRXINNYTSLIHSLIEESQNQQXKNEXELLE, (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 26)
BTWBXWDRXINNYTSXIHSXIEESQNQQXKNEXELLE, (SEQ ID NO: 27)
YTSXIHSXIEESQNQQEKNEQELLELDKWASLWNWF, (SEQ ID NO: 28)
YTSLIXSLIXESQNQQEKNEQELLELDKWASLWNWF, (SEQ ID NO: 29)
YTSLIHSLIEXSQNXQEKNEQELLELDKWASLWNWF, (SEQ ID NO: 30)
YTSLIHSLIEESQNQQXKNEXELLELDKWASLWNWF, (SEQ ID NO: 31)
YTSLIHSLIEESQNQQEXNEQXLLELDKWASLWNWF, (SEQ ID NO: 32)
YTSLIHSLIEESQNQQEKNEQXLLEXDKWASLWNWF, (SEQ ID NO: 33)
YTSLIHSLIEESQNQQEKNEQELLELDXWASXWNWF, (SEQ ID NO: 34)
YTSLIHSLIEESQNQQEKNEQELLELDKWXSLWXWF, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF,
```

-continued

```
                                        (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 41)
YTSXIHSXIEESQNQQXKNEXELLELDXWASXWNWF, (SEQ ID NO: 42)
BTWBXWDRXINNYTSLIHSLIEESQNQXEKNXQELLE,
or (SEQ ID NO: 43)
BTWBXWDRXINNYTSLIHSLIEESQNXQEKXEQELLE;
``` wherein X is any amino acid and further identifies the amino acid residues which are linked by a hydrocarbon staple, and B is methionine or norleucine.

Uses of the Modified Polypeptides

The antifusogenic capability of the modified peptides of the invention may additionally be utilized to inhibit or treat/ameliorate symptoms caused by processes involving membrane fusion events. Such events may include, for example, virus transmission via cell-cell fusion and virus-cell fusion. The peptides of the invention may be used to inhibit free viral, such as retroviral, e.g., HIV, transmission to uninfected cells wherein such viral infection involves membrane fusion events or involves fusion of a viral structure with a cell membrane.

In one aspect, the invention is directed to a method for inhibiting transmission of HIV to a cell. The method includes contacting the HIV virus with an effective dose of a modified polypeptide so that the HIV virus is inhibited from infecting the cell. Preferably, the modified polypeptide has a HIV gp41 heptad repeat domain (e.g., heptad repeat domain 1 or 2, or combinations thereof) that is stabilized with a hydrocarbon staple. Suitable modified polypeptides include those directed to the heptad repeat domain 1, wherein the polypeptide is 30% or more identical to the amino acid sequence of SEQ ID NO:2, SEQ ID NO:3 or SEQ ID NO:14 and forms an alpha-helix. Other suitable modified polypeptides include those directed to the heptad repeat domain 2, wherein the polypeptide is 30% or more identical to the amino acid sequence of FIG. 5, FIG. 6, SEQ ID NO:1 or 14 and forms an alpha-helix.

In yet another aspect, the invention is directed to a method for treating or delaying the onset of AIDS in an HIV infected individual. The method entails administering to an individual infected with HIV an effective dose of a pharmaceutical composition having a modified polypeptide with a stabilized HIV gp41 heptad repeat domain, thus treating or delaying the onset of AIDS. Preferably the HIV gp41 heptad repeat domain is stabilized with a hydrocarbon staple(s). Suitable polypeptides include those directed to the heptad repeat domain 1, wherein the polypeptide is 30% or more identical to an amino acid sequence of SEQ ID NO:2, SEQ ID NO:3 or SEQ ID NO:14 and forms an alpha-helix. Other suitable polypeptides include those directed to the heptad repeat domain 2, wherein the polypeptide is 30% or more identical to an amino acid sequence of FIG. 5, FIG. 6, SEQ ID NO:1 or 14 and forms an alpha-helix.

In still another aspect, the invention is directed to a method for increasing the number of CD4+ cells in an individual infected with HIV. The method involves administering to the individual infected with HIV an effective dose of a pharmaceutical composition having a modified polypeptide with a stabilized HIV gp41 heptad repeat domain. The administration of the composition results in an increase in the number of CD4+ cells in the individual. Preferably the HIV gp41 heptad repeat domain is stabilized with a hydrocarbon staple(s). Suitable polypeptides include those directed to the heptad repeat domain 1, wherein the polypeptide is 30% or more identical to an amino acid sequence of SEQ ID NO:2, SEQ ID NO:3 or SEQ ID NO:14 and forms an alpha-helix. Other suitable polypeptides include those directed to the heptad repeat domain 2, wherein the polypeptide is 30% or more identical to an amino acid sequence selected of FIG. 5, FIG. 6, or SEQ ID NO:1 and forms an alpha-helix.

In yet another aspect, the invention is directed to a method for inhibiting syncytia formation between an HIV infected cell and an uninfected cell. The method involves contacting the infected cell with an effective dose of a composition having a modified polypeptide with a stabilized HIV gp41 heptad repeat domain, thereby inhibiting syncytia formation between the cells. Preferably the HIV gp41 heptad repeat domain is stabilized with a hydrocarbon staple. Suitable polypeptides include those that are 30% or more identical to an amino acid sequence of FIG. 5, FIG. 6, SEQ ID NO:2, SEQ ID NO:3, SEQ ID NO:1, SEQ ID NO:13, or SEQ ID NO:14 and forms an alpha-helix.

In still another aspect, the invention is directed to a method for inactivating HIV. The method involves contacting the virus with an effective dose of a modified polypeptide having a stabilized HIV gp41 heptad repeat domain so that the HIV is rendered inactive (e.g., non-infectious). Preferably the HIV gp41 heptad repeat domain is stabilized with a hydrocarbon staple(s). Suitable polypeptides include those that are 30% or more identical to an amino acid sequence of FIG. 5, FIG. 6, SEQ ID NO:2, SEQ ID NO:3, SEQ ID NO:1, SEQ ID NO:13 or SEQ ID NO:14 and forms an alpha-helix.

In still another aspect, the invention is directed to a method for preventing an HIV infection in an individual. The method involves administering to an individual an effective dose of a pharmaceutical composition having modified polypeptide with a stabilized HIV gp41 heptad repeat domain, wherein the stabilized HIV gp41 heptad repeat domain interferes with the ability of the HIV to infect the individual. Suitable polypeptides include those directed to the heptad repeat domain 1, wherein the polypeptide is 30% or more identical to an amino acid sequence of SEQ ID NO:2, SEQ ID NO:3 or SEQ ID NO:14 and forms an alpha-helix. Other suitable polypeptides include those directed to heptad repeat domain 2, wherein the polypeptide is 30% or more identical to an amino acid sequence of FIG. 5, FIG. 6, SEQ ID NO:1 or 13 and forms an alpha-helix.

In another aspect, the invention is directed to a method for inhibiting the transmission of RSV to a cell. The method includes contacting the virus with an effective dose of a modified polypeptide having a stabilized RSV viral alpha helix heptad repeat-analog domain, thereby inhibiting transmission of the virus to a cell. Preferably the heptad repeat domain is stabilized with a hydrocarbon staple(s) Suitable modified polypeptides include those which are 30% or more identical to SEQ ID NO:4, SEQ ID NO:5, SEQ ID NO:11 and SEQ ID NO:12 and forms an alpha-helix.

In yet another aspect, the invention is directed to a method for inhibiting the transmission of influenza virus to a cell. The method includes contacting the virus with an effective dose of a modified polypeptide having a stabilized influenza viral alpha helix heptad repeat-analog domain, thereby inhibiting transmission of the virus to a cell. Preferably the heptad repeat domain is stabilized with a hydrocarbon staple(s). Suitable polypeptides are known in the art.

In yet another aspect, the invention is directed to a method for inhibiting the transmission of a parainfluenza virus to a cell. The method includes contacting the virus with an effective dose of a modified polypeptide having a stabilized parainfluenza viral alpha helix heptad repeat-analog domain, thereby inhibiting transmission of the virus to a cell. Preferably the heptad repeat domain is stabilized with a hydrocarbon staple(s). Suitable polypeptides include those which are 30% or more identical to (SEQ ID NO:6) and forms an alpha-helix.

In still another aspect, the invention is directed to a method for inhibiting the transmission of a coronavirus to a cell. The method includes contacting the coronavirus with an effective dose of a modified polypeptide having a stabilized coronavirus alpha helix heptad repeat-analog domain, thereby inhibiting transmission of the virus to a cell. Preferably the heptad repeat domain is stabilized with a hydrocarbon staple(s). Suitable polypeptides include those which are 30% or more identical to (SEQ ID NO:7) or (SEQ ID NO:8) and forms an alpha-helix.

In yet still another aspect, the invention is directed to a method for inhibiting the transmission of an ebola virus to a cell. The method includes contacting the ebolavirus with an effective dose of a modified polypeptide having a stabilized ebolavirus alpha helix heptad repeat-analog domain, thereby inhibiting transmission of the virus to a cell. Preferably the heptad repeat domain is stabilized with a hydrocarbon staple(s). Suitable polypeptides include those having an amino acid sequence which is 30% identical to (SEQ ID NO:9) or (SEQ ID NO:10) and forms an alpha-helix.

Preferably, any of the above modified polypeptides used in the methods of the invention have the structure of Formula (I), (II) or (III) as described herein.

Kits

The present invention also encompasses a finished packaged and labeled pharmaceutical product. This article of manufacture includes the appropriate unit dosage form in an appropriate vessel or container such as a glass vial or other container that is hermetically sealed. The pharmaceutical product may contain, for example, a compound of the invention in a unit dosage form in a first container, and in a second container, sterile water for injection. Alternatively, the unit dosage form may be a solid suitable for oral, transdermal, intranasal, intravaginal, cervical ring, or topical delivery.

In a specific embodiment, the unit dosage form is suitable for intravenous, intramuscular, intranasal, oral, intravaginal, cervical, topical or subcutaneous delivery. Thus, the invention encompasses solutions, solids, foams, gels, preferably sterile, suitable for each delivery route.

As with any pharmaceutical product, the packaging material and container are designed to protect the stability of the product during storage and shipment. Further, the products of the invention include instructions for use or other informational material that advise the physician, technician, or patient on how to appropriately prevent or treat the disease or disorder in question. In other words, the article of manufacture includes instruction means indicating or suggesting a dosing regimen including, but not limited to, actual doses, monitoring procedures (e.g. detection and quantitation of infection), and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with a viral disease by administering specific doses and using specific dosing regimens as described herein.

The following examples are provided merely as illustrative of various aspects of the invention and shall not be construed to limit the invention in any way.

EXAMPLES

Example 1

Synthesis of Hydrocarbon Stapled Alpha Helical Polypeptides

A combined strategy of structural analysis and chemical synthesis is applied to construct the modified polypeptides. Asymmetric syntheses of α,α-disubstituted amino acids is first performed as previously reported (Schafmeister, C. E., J. Po, and G. L. Verdine, *Journal of the American Chemical Society*, 2000. 122(24): p. 5891-5892; Walensky, L. D., et al., *Science*, 2004. 305(5689): p. 1466-1470). The modified polypeptide compounds are generated by replacing at least two naturally occurring amino acids with the α,α-disubstituted non-natural amino acids at discrete locations flanking either 2, 3 or 6 amino acids, namely the "i, i+3," "i, i+4" or "i, i+7" positions, respectively.

Locations for the non-natural amino acids and subsequent hydrocarbon staple(s) are carefully chosen so as not to interfere with N36 interactions (Chan, D. C., et al., *Cell*, 1997. 89(2): p. 263-273). Residues in positions a and d interact directly with N36, whereas, residues e and g may contact the N36 core as a result of the pitch of the six-helix bundle. Residues b, f, and c localize to the opposite face of the α-helix and are thus ideally located for placement of the hydrocarbon staple(s).

The modified polypeptides can be generated using solid phase Fmoc chemistry and ruthenium-catalyzed olefin metathesis, followed by peptide deprotection and cleavage, purification by reverse-phase high performance liquid chromatography, and chemical characterization using LC/MS mass spectrometry and amino acid analysis.

Alternatively an established fragment-based approach can be pursued ([Bray, B. L. *Nature Reviews* Drug Discovery, 2003. 2(7): p. 587-593; MYUNG-CHOL KANG, B. B., et al., *Methods and compositions for peptide synthesis*, U.S.P.a.T. Office, Editor. Jan. 18, 2000 USA). In this strategy, the peptide is divided into 3 fragments, such that an N-terminal, central, and C-terminal portion are synthesized independently. These polypeptide fragments should be generated using solid phase Fmoc chemistry and ruthenium-catalyzed olefin metathesis on super-acid cleavable resins, which will yield fully protected peptides having an Fmoc at the N-terminus, and either a C-terminal amide (for the C-terminal fragment) or a free carboxylate (for the central and N-terminal fragments). These fully protected fragments are purified by reverse-phase high performance liquid chromatography, followed by sequential deprotection, coupling, and purification, to yield the full length, fully protected polypeptides. Global deprotection, followed by reverse-phase high performance liquid chromatography will yield the final products, which can be characterized using LC/MS mass spectrometry and amino acid analysis.

Example 2

Determining the Secondary Structure and Proteolytic Stability of the Modified Polypeptides The α-helicity of stapled modified polypeptides can be compared to their unmodified counterparts by circular dichroism. CD spectra can be obtained on a Jasco J-710 or Aviv spectropolarimeter at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The α-helical content of each peptide is calculated by dividing the mean residue ellipticity $[\Theta]222_{obs}$ by the reported $[\Theta]222_{obs}$ for a model helical peptide (Forood, B., E. J. Feliciano, and K. P. Nambiar, *PNAS*, 1993. 90(3): p. 838-842; J. Martin Scholtz, Biopolymers, 1991. 31(13): p. 1463-1470; Lawless, M. K., et al., *Biochemistry*, 1996. 35(42): p. 13697-13708) or using, for example, the Aviv machine using CDNN software developed by Brohm in order to deduce five different secondary structure fractions (helix, parallel and antiparallel beta-sheet, beta-turn and random coil). Protein Engineering, 1992. 5(3); p. 191-195

To assess whether helix stabilization confers enhanced protease resistance and serum stability, the modified polypeptides can be subjected to trypsin/chymotrypsin degradation assays and in vitro and in vivo serum stability assays, and compared to their unmodified counterparts as previously described (Walensky, L. D., et al., Science, 2004. 305(5689): p. 1466-1470). Recovery of intact compound is determined, for example, by flash freezing the in vitro or serum specimens in liquid nitrogen, lyophilization, and extraction in 50:50 acetonitrile/water containing 0.1% trifluoroacetic acid, followed by LC/MS based detection and quantitation.

Example 3

Optimization of the Biophysical and Biochemical Properties of the Modified Polypeptides by Evaluating Diversified Modified Peptide Libraries Synthesized in High-throughput Fashion High-throughput technologies can be used to optimize the modified polypeptides activities for cellular and in vivo studies. For example, an Apex 396 multichannel synthesizer (AAPPTEC; Louisville, Ky.) can be used to produce polypeptide libraries for biological evaluation. The polypeptide compounds can be diversified by extension, truncation, or amino acid substitution across natural and select non-natural amino acids, and differential staple localization can be made to maximize their biophysical and biochemical properties. The libraries are generated using high-throughput solid phase Fmoc chemistry and ruthenium-catalyzed olefin metathesis and peptide deprotection and cleavage. Peptide purification is achieved by reverse phase C18 HPLC, and products characterized by LC/MS mass spectrometry and amino acid analysis.

Example 4

Evaluating the Modified Polypeptides Ability to Target and Inhibit HIV Fusion

The binding activity and functional effects of the HIV modified polypeptides can be assessed in fluorescence polarization, syncytial fusion, and HIV infectivity assays. Equilibrium binding constants can be determined by fluorescence polarization assays (FPA) using fluorescein isothiocyanate (FITC)-labeled modified polypeptides and titrated recombinant five-helix bundle protein. FPA experiments can be performed using a BMG Labtech FLUOstar optima microplate reader, and dissociation constants determined by regression analysis using GraphPad software (Prism). The recombinant 5-helix bundle protein, first developed by Root et al., contains five of the six helices that comprise the core of the gp41 trimer-of-hairpins, which are connected by short peptide linkers (Root, M. J., M. S. Kay, and P. S. Kim, *Science*, 2001. 291(5505): p. 884-888). Because the 5-helix bundle lacks the third C-peptide helix and under experimental conditions is soluble, stable, and helical, incorporation of the sixth C-peptide in the form of FITC-modified polypeptide would provide a direct measure of binding activity. In this manner, modified polypeptides, differing in peptide sequence, staple location, and staple number, can be screened for maximal in vitro binding activity. Binding activity can also be determined indirectly by competition assays in which the 5-helix bundle is combined with a FITC-labeled unmodified HIV fusion inhibitor peptide and then unlabeled stapled gp41 peptides are added at increasing concentrations followed by measurement of fluorescence polarization and then calculation of Ki by nonlinear regression analysis, as indicated above.

Alternatively, an alternative binding assay can be employed based upon the "gp41-5" construct of Frey et al. Gp41-5 binds with high affinity to added peptides that contain all or part of the missing CHR. For example, using gp41-5 and fluorescein-labeled C38 (residues 117-154), Frey et al. successfully generated an FPA binding curve that revealed a $K_d$ of 3.6 nM (Frey, G., et al., *PNAS*, 2006. 103(38): p. 13938-13943).

Functional assays can also be used to evaluate the modified polypeptides activity. In culture, multinucleated giant cells or "syncytia" form as a result of direct cell-cell fusion between HIV-1-infected and uninfected CD4-positive cells. In the syncytia formation assay, an indicator cell line expressing the CD4 receptor, and a fusogenic cell line that lacks the CD4 receptor but contains HIV-1 proteins on the surface, fuse to generate 70-100 multinucleated giant cells in culture within 48 h. Syncytia are then counted using an inverted microscope. The ability of stabilized alpha helix of gp41 (SAH-gp41) compounds to inhibit syncytia formation in a dose-responsive fashion is used as a functional measure of fusion inhibition, for which $IC_{50}$s can be determined and compared with peptides T20 and T649 (Brenner, T. J., et al. *The Lancet*, 1991. 337(8748): p. 1001-1005; Madani, N., et al., *Journal of Virology*, 2007. 81(2): p. 532-538).

Also the anti-viral properties of the modified polypeptides can be quantified based upon their capacity to directly block HIV infection of CD4-positive and CCR5-expressing canine thymus cells. Recombinant HIV-1 viruses (eg. HXBc2, YU2, and additional strains available through the NIH AIDS Research and Reference Reagent Program) expressing firefly luciferase and containing the indicated envelope glycoproteins can be used to infect Cf2Th-CD4-CCR5/CXCR4 cells in the presence of serially diluted HIV modified polypeptides. After 48 hours, the cells are lysed and luciferase activity is quantified (Si, Z. H., M. Cayabyab, and J. Sodroski, *Journal of Virology*, 2001. 75(9): p. 4208-4218 Si, Z. H., et al., *PNAS*, 2004. 101(14): p. 5036-5041). The identical experiment is performed with the amphotropic murine leukemia virus (AMLV), to monitor for any nonspecific effects of the modified polypeptides. Similar control assays may be performed with non-HIV modified polypeptides of the invention and are known in the art.

Example 5

Evaluate the Ability of SAH-gp41 Compounds to Overcome Resistance to Enfuvirtide Heavily antiretroviral-treated HIV-positive patients who respond to initial treatment with enfuvirtide, may ultimately develop a viral rebound that typically occurs within a maximum of 80 weeks. Resistance to enfuvirtide derives from mutations within the HR-1 region of gp41, although some genetic changes are found in the HR-2 domain (Xu, L., et al., *Antimicrobial Agents and Chemotherapy,* 2005. 49(3): p. 1113-1119; Perez-Alvarez, L., et al. *Journal of Medical Virology,* 2006. 78(2): p. 141-147). These mutations, such as I37V, V38A/E/M, Q39R, Q40H, N42T/Q/H, N43D/Q, are only found in enfuvirtide-experienced patients (Poveda, E., et al., *Journal of Medical Virology,* 2004. 74(1): p. 21-28; Melby, T., et al., *Aids Research and Human Retroviruses,* 2006. 22(5): p. 375-385; Sista, P. R., et al., *Aids,* 2004. 18(13): p. 1787-1794; Wei, X. P., et al., *Antimicrobial Agents and Chemotherapy,* 2002. 46(6): p. 1896-1905).

Figures 20A, 20B:
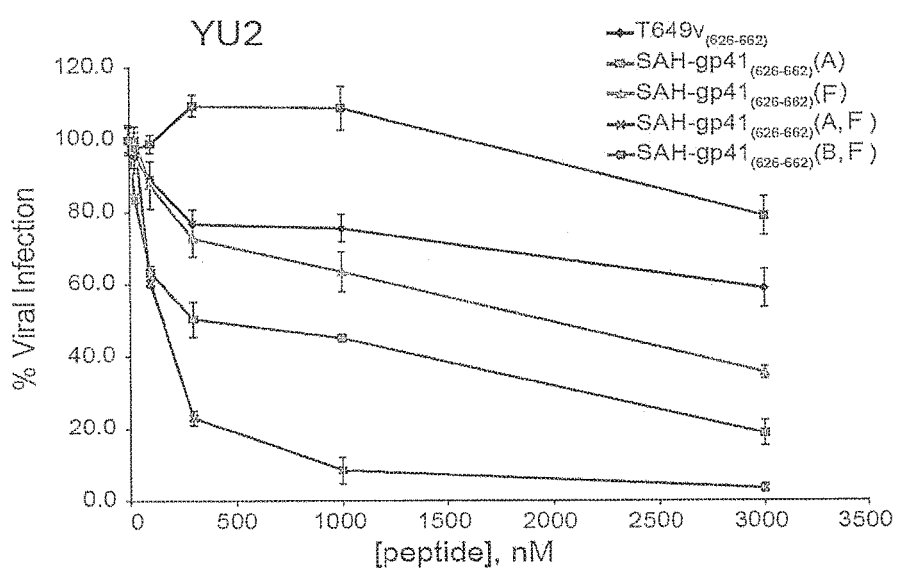
FIGS. 20A-FIG. 20B demonstrate that FIG. 20A) SAH-gp41 compounds overcome HIV-1 HR1 resistance mutations that block the binding of unmodified gp41-based fusion peptides.

Structural analysis and molecular modeling can be used to evaluate the impact of these mutations on the binding interface of the HR-1 domain with enfuvirtide. Five-helix bundle proteins incorporating resistance mutations can then be generated for binding analysis as described in Example 4. FITC-labeled SAH-gp41 compounds can then be screened against these mutant five-helix bundle proteins to determine if any native SAH-gp41 compounds retain activity despite HR domain mutations. Alternatively, HR1 peptides that contain resistance mutations are synthesized and can be directly incubated with SAH-gp41 compounds, and then run on native gels to detect and quantitate the formation of heteroduplexes, which represent HR1-SAH-gp41 complex, detectable by fluorescence scanning of the gel (FIG. 20A). SAH-gp41 compounds should contain T649 sequences known to contact two gp41 residues (Leu-568 and Trp-571) that are critical for fusion activity. By incorporating this sequence functionality, the SAH-gp41 compounds may overcome enfuvirtide-resistant virus and are less likely to elicit a resistant virus, in contrast to analogs, like T20, that lack such residues at the N-terminal region of the HR-2 domain (Cao, J., et al., *Journal of Virology,* 1993. 67(5): p. 2747-2755; Chan, D. C., C. T. *PNAS* 1998. 95(26): p. 15613-15617; Rimsky, L. T., D. C. Shugars, and T. J. Matthews, *J. Virol.,* 1998. 72(2): p. 986-993). Follow-up HIV infectivity studies would evaluate the functional activity of such SAH-gp41 compounds against the corresponding primary resistant isolates.

To monitor for restoration of SAH-gp41 activity, FITC labeled mutants SAH-gp41 (mSAH-gp41) compounds can be screened for binding affinity to mutant five-helix bundle proteins and for suppression of HIV infectivity using primary resistance strains.

To explore the evolution of potential resistance to SAH-gp41 compounds, HIV strains can be evolved in the presence of increasing concentrations of lead SAH-gp41 compounds. Resistant strains can be genotyped for comparative mutational analysis between these mutants and enfuvirtide-resistant mutants (Van Laethem, K., et al., *Journal of Virological Methods,* 2005. 123(1): p. 25-34). Because resistance to one type of entry inhibitor may not affect susceptibility to other variants, (Ray, N., et al., *Journal of Virology,* 2007. 81(7): p. 3240-3250) combined SAH-gp41 and mSAH-gp41 polypeptide compositions can be formulated.

Alternative, a phage display strategy can be employed. Lai et al. successfully used phage display to restore heterodimerization of a coiled-coil pair of α-helices after destabilizing mutations were introduced (Lai, J. R., et al., *Journal of the American Chemical Society,* 2004. 126(34); p. 10514-10515). Whereas complimentary electrostatic pairing preferences among helical residues that flank the core are readily apparent, less is known about the packing preferences of non-polar residues located at core positions (Lumb, K. J. and P. S. Kim, *Science,* 1995. 268(5209): p. 436-439) Using phage display, one can screen all possible amino acid combinations at up to 7 variable locations of the HR-2 domain for binding affinity to a mutant HR-1 domain, using the corresponding five-helix bundle. In addition, phage display screening of fully randomized HR-2 domains against combinations of known mutations in HR-1 domains could be undertaken in order to determine the SAH-gp41 sequence capable of forming the most stable complex with the 5-helix bundle (Xu, L., et al., *Antimicrobial Agents and Chemotherapy,* 2005. 49(3): p. 1113-1119; Perez-Alvarez, L., et al., *Journal of Medical Virology,* 2006. 78(2): p. 141-147). After three cycles of "panning", phage DNA sequencing would reveal those peptide sequences having the highest binding affinities for the mutant 5-helix bundle. The corresponding SAH-gp41 derivatives would then be synthesized and evaluated in binding and activity studies as described above.

Example 6

Analyze the In Vivo Stability, Pharmacokinetics, and Biodistribution of SAH-gp41 Compounds A rigorous assessment of the in vivo pharmacology of SAH-gp41 compounds can be used to determine and optimize the therapeutic potential of the modified polypeptides. For in vivo serum half-life studies, 5-50 mg/kg of FITC-labeled or unlabeled SAH-gp41 polypeptides can be injected or delivered orally into control mice and blood specimens withdrawn for example at 0, 0.25, 0.5, 1, 2, 4, 8, 12, and 24 hours post-injection to measure levels of intact compound by HPLC as previously described (Walensky, L. D., et al., *Science,* 2004. 305(5689): p. 1466-14701) or by reverse-phase LC/MS, followed by mathematical determination of pharmacokinetic parameters using formulas and software known in the art. LC/MS-based characterization of metabolites can also be performed. 111In-DOTA-derivatized compounds can be synthesized and injected into control mice for measurement of tissue uptake, excretion, and biodistribution of the modified polypeptide compounds over time by radioisotope scintillation counting. SPECT/NMR imaging of control mice injected with 111In-DOTA-derivatized modified compounds will provide high resolution images of biodistribution in real time as previously performed by the Walensky lab in collaboration with Ralph Weissleder, MD of Massachusetts General Hospital (Hird V, V. M., et al. *Br J Cancer,* 1991. 64(5): p. 911-4). Chemical modifications, including lipidation, polysialylation, or antibody-conjugation, could be performed should optimization of pharmacokinetics and tissue targeting of modified compounds.

Example 7

Native gp41 C-terminal Heptad Peptides are Predominantly Random Coils in Solution gp41 HR-2-derived peptides based upon the sequences of T20 (residues 638-673) and a T649 variant, T649v (residues 626-662, rather than T649 is 628-663) were prepared and the circular dichroism (CD) spectra determined at physiologic pH. The native peptides display only modest minima at 222 nm and 208 nm, suggesting predominantly random coil structure in solution. Indeed, the calculated α-helical content (Forood, B., E. J. Feliciano, and K. P. Nambiar, *PNAS,* 1993. 90(3): p. 838-84; J. Martin Scholtz, *Biopolymers,* 1991. 31(13): p. 1463-1470; Lawless, M. K., et al., *Biochemistry,* 1996. 35(42): p. 13697-13708) was only ~25% for T20 and 14% for T649v. Thus, synthetic gp41-derived HR-2 peptides are predominantly disordered in solution, reflecting a significant loss of bioactive structure.

Example 8

Figure 17:
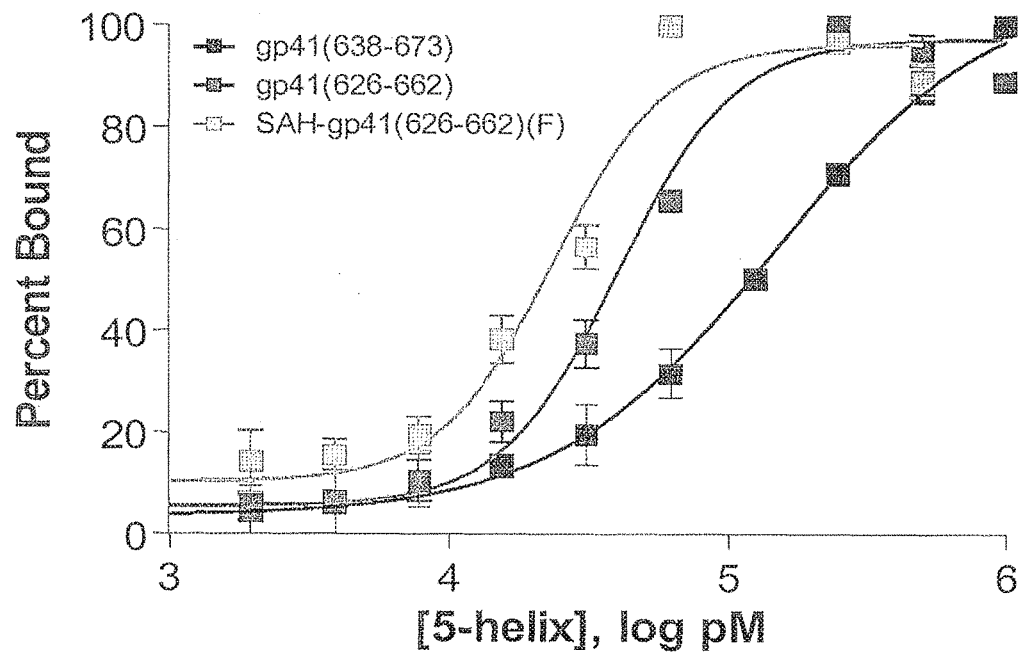
FIG. 17 shows a fluorescence polarization binding analysis of HIV fusion inhibitor peptides to the gp41 five-helix bundle illustrating enhanced binding of SAH-gp41 to the five-helix bundle compared to the unmodified peptides.

Truncated C-terminal Heptad Peptides Display Enhanced α-Helicity Upon Incorporation of an All-hydrocarbon Staple In order to improve the biochemical properties of HIV gp41-HR-2 peptides the T649v peptide was truncated to yield a 20-mer consisting of residues 626-645 (FIG. 7). The truncated SAH-gp41 compound, SAH-gp41(626-645)(A), was successfully synthesized in high yield. Analysis of comparative CD spectra revealed marked enhancement of α-helical content for SAH-gp41(626-645)(A) compared to its unstapled counterpart (48% vs. 20%). Evaluation of the compounds in an HIV syncytial formation assay revealed markedly enhanced inhibitory activity of SAH-gp41(626-645)(A) compared to its unstapled derivative. Thus, in spite of eliminating more than 40% of the residues of T649v, the hydrocarbon staple successfully transformed a 20-mer gp41 truncation with little α-helicity and only modest anti-syncytial activity, into an α-helical compound with significant structural stabilization and potent anti-syncytial activity (IC90, ~100 nM) (FIG. 18).

The activity of SAH-gp41(626-645)(A) peptide was compared to the clinically approved T20 peptide in an HIV infectivity assay using the HXBc2 strain. The SAH-gp41 (626-645)(A) displayed significant anti-HXBc2 activity, particularly given the markedly shortened construct.

Example 9

SAH-gp41 Compounds Demonstrate Marked α-Helical Stabilization, Proteolytic Stability, Thermal Stability, 5-Helix Bundle Binding Affinity To optimize the activity of tSAH-gp41 peptides, an alternative strategy based upon inserting one or more hydrocarbon staples into the full-length gp41-HR-2 constructs was pursued (FIG. 11, 12). Unmodified enfuvirtide and T649v were predominantly unstructured in pH 7 aqueous solution at 21° C., exhibiting less than 20% α-helicity (FIG. 14A,B). All stapled derivatives displayed comparatively increased α-helical content, with up to 4.7-fold structural stabilization (FIG. 14A-C). The insertion of either one or two hydrocarbon staples consistently transformed the circular dichroism spectra from a random coil pattern with a predominant single minimum at 204 nm to an α-helical contour with double minima at 208 and 222 nm. For select peptide templates, single C-terminal stapling conferred a greater degree of α-helical stabilization than single N-terminal stapling. Select doubly stapled SAH-gp41 compounds exhibited an intermediate enhancement in α-helical structure, balancing the effects of the N- and C-terminal singly stapled peptides. Enhancement of peptide α-helicity was likewise observed at pH2, and in most cases, SAH-gp41 compounds were even more helical at pH2 than at pH7 (FIG. 14D-F).

To assess the resistance of SAH-gp41 peptides to thermal unfolding, we performed circular dichroism studies across a 1-91° C. temperature range. We observed that select single and double stapling of HIV-1 fusion inhibitor peptides conferred α-helical stabilization that was remarkably heat-resistant, sustaining an up to 2.3-fold enhancement in α-helicity even at 91° C. (FIG. 15).

A major limitation of peptides as therapeutics is their susceptibility to rapid proteolytic degradation. Biologically active peptides such as enfuvirtide that are lengthy, unfolded, and replete with protease sites are particularly vulnerable. One of the potential benefits of a covalent crosslinking strategy to enforce peptide α-helicity is shielding of the vulnerable amide bonds from proteolysis. Because proteases require that peptides adopt an extended conformation to hydrolyze amide bonds, the structural constraint afforded by the hydrocarbon staple can render crosslinked peptides protease-resistant. To determine if hydrocarbon stapling, and especially double stapling, could protect the 36 to 37-mer HIV-1 fusion peptides from proteolysis, we subjected enfuvirtide, T649v, and SAH-gp41 peptides to direct protease exposure in vitro. To especially challenge the stapled peptides, we selected chymotrypsin, which can cleave gp41 HR2 peptides at numerous consensus cleavage sites, including 9-11 locations for SAH-gp41(638-673) and 7 locations for SAH-gp41(626-662).

In the presence of 0.5 ng/μL chymotrypsin, enfuvirtide and T649v (25 μM) exhibited rapid degradation, with half-lives of 12 and 14 minutes, respectively (FIG. 16A-C). In comparison, singly stapled SAH-gp41 compounds displayed longer half-lives that ranged from 21 to 200 minutes. The majority of doubly stapled compounds markedly surpassed their singly stapled counterparts, with select doubly stapled peptides achieving half-lives of up to 1275 minutes. In most cases, double stapling had a stronger influence on proteolytic stability than overall peptide α-helicity, as select doubly stapled peptides had lower α-helicity than select singly stapled peptides, but still exhibited superior protease resistance. Almost all stapled peptides had the identical number of chymotrypsin cleavage sites as the corresponding unmodified peptides, emphasizing that the observed protease resistance derived from peptide stapling itself, rather than elimination of cleavage sites.

Peptides have poor oral bioavailability in part due to rapid acid hydrolysis in the proximal digestive tract. The compelling protease resistance of doubly stapled SAH-gp41 compounds at neutral pH prompted us to explore their stability under acidic conditions. In each case, acidification of the peptide solutions significantly enhanced their α-helical content as measured by CD (FIG. 16D-F). Upon exposure to pepsin at 0.5 ng/μL, enfuvirtide and T649v (25 μM) exhibited rapid degradation, with half-lives of 4 and 11 minutes, respectively. Select doubly stapled SAH-gp41 compounds displayed half-lives ranging from approximately 80-800-fold greater than the unmodified peptides, and consistently surpassed their singly stapled counterparts. Remarkably, select doubly-stapled SAH-gp41 peptides remained 80% intact after exposure to pepsin at pH 2 for more than 12 hours. As observed for chymotrypsin resistance, double stapling itself, rather than overall peptide α-helicity or number of cleavage sites, correlated with the superior resistance to pepsin hydrolysis. These studies highlight the capacity of double stapling to generate HIV-1 fusion inhibitor peptides with unprecedented resistance to proteolytic hydrolysis at both neutral and acidic pH.

The compounds of the invention were also measured for their affinity to gp41 in a five-helix binding assay as described herein. As shown in FIG. 17 the modified compounds bound substantially better than the unmodified control polypeptides.

Example 10

Figure 18:
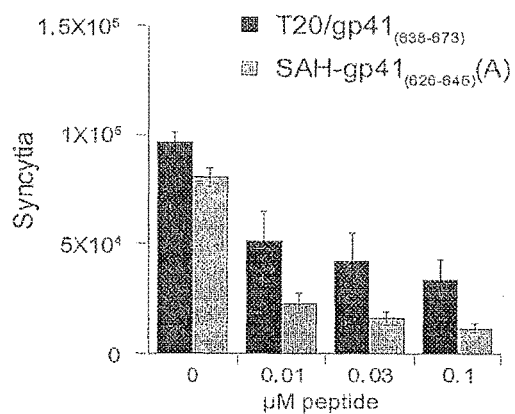
FIG. 18 shows improved inhibition of syncytia formation by a truncated SAH-gp41 compound (A) compared to enfuvirtide (T20: gp41$_{(638-673)}$), highlighting the potential to retain, and even enhance, anti viral activity with shorter, stapled peptides.

SAH-gp41 Compounds Demonstrate Anti-syncytial Formation Activity and Anti-HIV Viral Fusion Activity The compounds of the invention were assayed for inhibition of syncytial formation using methods well known to those skilled in the art. The results of the assay are shown in FIG. 18. Equal amounts of either T20/gp41$_{(638-673)}$ or SAH-gp41$_{(626-645)}$A were added to the media. As shown, the modified compounds inhibited syncytial formation more so than unmodified control polypeptides.

In order to determine the functional impact of hydrocarbon-stapling on gp41-based fusion inhibitor activity, SAH-gp41 compounds were tested and compared to their unmodified counterparts in a luciferase-based HIV infectivity assay (Si, Z. H., M. Cayabyab, and J. Sodroski, *Journal of Virology*, 2001. 75(9): p. 4208-4218; Si, Z. H., et al., *PNAS*, 2004. 101(14): p. 5036-5041). Recombinant HIV-1 bearing the envelope glycoproteins from three distinct HIV-1 strains, HXBc2, ADA, and HXBc2P 3.2, and a negative control virus bearing the amphotropic murine leukemia virus (A-MLV) envelope glycoproteins, were evaluated. Compared to enfuvirtide, select SAH-gp41(638-673) peptides exhibited a 3- to 15-fold enhancement of inhibitory activity across all three HIV-1 strains (FIG. 19). T649v, an HR2 peptide that encompasses a 37-amino acid fragment terminating 11 residues upstream of enfuvirtide's C-terminus, displayed 26-, 40-, and 16-fold greater inhibitory activity than enfuvirtide against viruses with the HXBc2, ADA, and HXBc2P 3.2 envelope glycoproteins, respectively. Given the marked potency of T649v against these viral strains, we found that the corresponding SAH-gp41 peptides showed essentially comparable activity in infectivity assays. In order to probe for differential anti-viral potencies among T649v-based stapled peptides, we screened the compounds against viruses with envelope glycoproteins derived from the more resistant primary R5 isolate, YU2. Compared to T649v, select SAH-gp41(626-662) peptides demonstrated enhanced anti-YU2 activity (FIG. 19, 20B). The ability of SAH-gp41 peptides to overcome HIV-1 HR1 resistance mutations, was further underscored by the superior binding activity of select SAH-gp41 peptides to mutant HR1 peptides, as compared to unmodified gp41-based fusion peptides, when assayed by fluorescence scan of electopheresed mixtures of HR1 and HR2/SAH-gp41 peptides (FIG. 20A).

These functional data reveal that insertion of one or more hydrocarbon staples can yield SAH-gp41 peptides with potent and broad anti-HIV-1 activity. The importance of striking a balance between α-helical stabilization, proteolytic stability, and anti-viral activity is underscored by the doubly stapled SAH-gp41(626-662)(A, F) peptide, which combines intermediate α-helical stabilization, the striking anti-proteolysis feature of double stapling, and potent anti-viral activity, to yield a pharmacologically optimized HIV-1 fusion inhibitor peptide.

Example 11

A Doubly Stapled SAH-gp41 Peptide Demonstrates Striking Enhancement of In Vivo Stability and Bioavailability Compared to the Corresponding Unmodified Peptide Male C57/BL6 mice were administered intravenously or by oral gavage 10 mg/kg of either SAH-gp41$_{(626-662)}$(A,F) or the corresponding unmodified peptide. Blood samples withdrawn at 30 minutes by retro-orbital bleed were subjected to quantitation using LC/MS-based blood tests. The level of SAH-gp41$_{(626-662)}$(A,F) measured in the blood was more than 6-fold greater than the measured level of the corresponding unmodified peptide. Strikingly, 30 minutes after oral administration, intact SAH-gp41$_{(626-662)}$(A,F) was detected in the blood at measurable levels, whereas the unmodified peptide was undetectable (FIG. 21). These data emphasize that hydrocarbon stapling confers unique pharmacologic properties to gp41-based fusion peptide sequences, enhancing their in vivo stability and even conferring measurable oral bioavailability. This single dose experiment demonstrates that the SAH-gp41 peptides could be dosed at a level to provide serum levels of the compound comparable to the level of an unmodified peptide (e.g., enfuvirtide) suggesting that a therapeutically effective dose could be administered orally.

All patents, patent applications, GenBank numbers, and published references cited herein are hereby incorporated by reference in their entirety as if they were incorporated individually. While this invention has been particularly shown and described with references to preferred embodiments thereof, it will be understood by those skilled in the art that various changes in form and details may be made therein without departing from the scope of the invention encompassed by the appended claims.

What is claimed is:

1. A cross-linked polypeptide comprising a stabilized alpha helix of a viral heptad repeat (HR) domain, wherein the stabilized HR domain is stabilized with two hydrocarbon staples, and wherein a hydrocarbon staple is positioned so as to link amino acid residues i and i+3, amino acid residues i and i+4, or amino acid residues i and i+7.

2. The cross-linked polypeptide of claim 1, wherein said stabilized alpha helix of a viral heptad repeat domain is derived from a virus selected from the group consisting of human immunodeficiency virus (HIV), simian immunodeficiency virus (SIV), respiratory syncytial virus (RSV), parainfluenza virus, paramyxovirus, influenza virus, coronavirus, and filovirus.

3. The cross-linked polypeptide of claim 1, wherein said modified polypeptide comprises 20 or more amino acids.

4. The cross-linked polypeptide of claim 1, wherein said cross-linked polypeptide has at least 10%, 20%, 30%, 50%, 60%, 70%, 80%, or 90% alpha helicity in aqueous solution as determined by circular dichroism.

5. The cross-linked polypeptide of claim 2, wherein said heptad repeat domain comprises an HIV-1 gp41 heptad repeat domain 1, an HIV-1 gp41 heptad repeat domain 2, an HIV-2 heptad repeat domain 1, an HIV-2 heptad repeat domain 2, an SIV gp41 heptad repeat domain 1, or an SIV gp41 heptad repeat domain 2.

6. The cross-linked polypeptide of claim 1, wherein said cross-linked polypeptide is a chimera.

7. The cross-linked polypeptide of claim 6, wherein said chimera has the amino acid sequence of WQEWEQKI-TALLEQAQIQQEKNEYELQKLDKWASLWEWF (SEQ ID NO: 46).

8. The cross-linked polypeptide of claim 2, wherein said stabilized alpha helix of a viral heptad repeat domain is derived from RSV, and wherein said heptad repeat domain forms an alpha helix and is 30% or more identical to the amino acid sequence selected from the group consisting of:

```
                                              (SEQ ID NO: 4)
YTSVITIELSNIKENKCNGTDAKVKLIKQELDKYKNAVTELQLLMQST, (SEQ ID NO: 5)
FYDPLVFPSDEFDASISQVNEKINQSLAFIRKSDELL, (SEQ ID NO: 11)
SGIAVSKVLHLEGEVNKIKNALLSTNKAVVSLSNGVSVLTSKVLDLKSY
INNQLLPI-,
and (SEQ ID NO: 12)
PIINYYDPLVFPSDEFDASISQVNEKINQSLAFIRRSDELLHNVNTGKST
TNIM.
```

9. The cross-linked polypeptide of claim 2, wherein said stabilized alpha helix of a viral heptad repeat domain is derived from HIV, and wherein said heptad repeat domain forms an alpha helix and is 30% or more identical to the amino acid sequence selected from the group consisting of:

```
                                              (SEQ ID NO: 1)
YTSLIHSLIEESQNQQEKNEQELLELDKWASLWNWF, (SEQ ID NO: 2)
NNLLRAIEAQQHLLQLTVWGIKQLQARILAVERYLQDQ, (SEQ ID NO: 3)
BTWBEWDREINNYTSLIHSL, (SEQ ID NO: 13)
MTWMEWDREINNYTSLIHSLIEESQNQQEKNEQELLE, (SEQ ID NO: 58)
YTHIIYSLIEQSQNQQEKNEQELLALDKWASLWNWF, (SEQ ID NO: 59)
MTMKWEREIDNYTHIIYSLIEQSQNQQEKNEQELLA,
```

-W-W-I-Y-I-L-S-Q-N-E-L, or conservative amino acid substitutions thereof and wherein "-"can be any amino acid (SEQ ID NO: 44), -TW-WDR-I-Y-I-LI-Q-QEK-E-L-EL, or conservative amino acid substitutions thereof and wherein "-"can be any amino acid (SEQ ID NO: 45),

```
                                              (SEQ ID NO: 20)
BTWBXWDRXINNYTSLIHSLIEXSQNXQEKNEQELLE, (SEQ ID NO: 22)
BTWBXWDRXINNYTSLIHSLIEESQNQQXKNEXELLE,
```

```
                                                  (SEQ ID NO: 23)
BTWBEWDXEINXYTSLIHSLIEESQNQQXKNEXELLE, (SEQ ID NO: 24)
BTWBEWDREINXYTSXIHSLIEESQNQQXKNEXELLE, (SEQ ID NO: 25)
BTWBEWDREINNYTSXIHSXIEESQNQQXKNEXELLE, (SEQ ID NO: 35)
YTSLIHSLIEXSQNXQEKNEQXLLEXDKWASLWNWF, (SEQ ID NO: 36)
YTSXIHSXIEESQNQQEKNEQELLELDKWXSLWXWF, (SEQ ID NO: 37)
YTSLIHSLIEESQNQQXKNEXELLELDKWXSLWXWF, (SEQ ID NO: 38)
YTSXIHSXIEESQNQQXKNEXELLELDKWASLWNWF, (SEQ ID NO: 39)
YTSXIHSXIEESQNQQEKNEQELLELDXWASXWNWF, (SEQ ID NO: 40)
YTSLIHSLIEXSQNXQEKNEQELLELDXWASXWNWF, (SEQ ID NO: 42)
BTWBXWDRXINNYTSLIHSLIEESQNQXEKNXQELLE,
and (SEQ ID NO: 43)
BTWBXWDRXINNYTSLIHSLIEESQNXQEKXQELLE,
``` wherein X is any amino acid and further identifies the amino acid residues which are linked by a hydrocarbon staple, and B is methionine or norleucine.

10. The cross-linked polypeptide of claim 2, wherein said stabilized alpha helix of a viral heptad repeat domain is derived from SIV, and wherein said heptad repeat domain forms an alpha helix and is 30% or more identical to WQEWERKVDFLEENITALLEEAQIQQEK (SEQ ID NO: 62).

11. The cross-linked polypeptide of claim 2, wherein said stabilized alpha helix of a viral heptad repeat domain is derived from parainfluenza virus, and wherein said heptad repeat domain forms an alpha helix and is 30% or more identical to ALGVATSAQITAAVALVEAKQARSDIEKLKEAIR (SEQ ID NO:6).

12. The cross-linked polypeptide of claim 2, wherein said stabilized alpha helix of a viral heptad repeat domain is derived from coronavirus, and wherein said heptad repeat domain forms an alpha helix and is 30% or more identical to NVLYENQKQIANQFNKAISQIQESLTTTSTALGKLQDVVNQNAQALNTLVKQ LSSNFGAISSVLNDILSRLDKVEAE (SEQ ID NO:7) or TSPDVDFGDISGINASVVNIQKEIDRLNEVAKNLNESLIDLQELGKY (SEQ ID NO:8).

13. The cross-linked polypeptide of claim 2, wherein said stabilized alpha helix of a viral heptad repeat domain is derived from Filovirus, and wherein said heptad repeat domain forms an alpha helix and is 30% or more identical to DGLICGLRQLANETTQALQLFLRATTELRTFSILNRKAIDFLL (SEQ ID NO:9) or DWTKNITDKIDQIIHDFVDKTLPD (SEQ ID NO:10).

14. A composition comprising the cross-linked polypeptide of claim 1.

15. The composition of claim 14, wherein said composition is a pharmaceutical composition.

* * * * *

SEQUENCE LISTING

```
<160> NUMBER OF SEQ ID NOS: 100

<210> SEQ ID NO 1
<211> LENGTH: 36
<212> TYPE: PRT
<213> ORGANISM: Human immunodeficiency virus-1

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

```
<210> SEQ ID NO 2
<211> LENGTH: 38
<212> TYPE: PRT
<213> ORGANISM: Human immunodeficiency virus-1

<400> SEQUENCE: 2

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Gln Asp Gln
        35

<210> SEQ ID NO 3
<211> LENGTH: 20
<212> TYPE: PRT
<213> ORGANISM: Human immunodeficiency virus-1
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle

<400> SEQUENCE: 3

Xaa Thr Trp Xaa Glu Trp Asp Arg Glu Ile Asn Asn Tyr Thr Ser Leu
1               5                   10                  15

Ile His Ser Leu
            20

<210> SEQ ID NO 4
<211> LENGTH: 48
<212> TYPE: PRT
<213> ORGANISM: Respiratory syncytial virus

<400> SEQUENCE: 4

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu Gln Leu Leu Met Gln Ser Thr
        35                  40                  45

<210> SEQ ID NO 5
<211> LENGTH: 37
<212> TYPE: PRT
<213> ORGANISM: Respiratory syncytial virus

<400> SEQUENCE: 5

Phe Tyr Asp Pro Leu Val Phe Pro Ser Asp Glu Phe Asp Ala Ser Ile
1               5                   10                  15

Ser Gln Val Asn Glu Lys Ile Asn Gln Ser Leu Ala Phe Ile Arg Lys
            20                  25                  30

Ser Asp Glu Leu Leu
        35

<210> SEQ ID NO 6
<211> LENGTH: 34
<212> TYPE: PRT
<213> ORGANISM: Parainfluenza virus
```

-continued

```
<400> SEQUENCE: 6

Ala Leu Gly Val Ala Thr Ser Ala Gln Ile Thr Ala Ala Val Ala Leu
1               5                   10                  15

Val Glu Ala Lys Gln Ala Arg Ser Asp Ile Glu Lys Leu Lys Glu Ala
            20                  25                  30

Ile Arg

<210> SEQ ID NO 7
<211> LENGTH: 77
<212> TYPE: PRT
<213> ORGANISM: Coronavirus

<400> SEQUENCE: 7

Asn Val Leu Tyr Glu Asn Gln Lys Gln Ile Ala Asn Gln Phe Asn Lys
1               5                   10                  15

Ala Ile Ser Gln Ile Gln Glu Ser Leu Thr Thr Thr Ser Thr Ala Leu
            20                  25                  30

Gly Lys Leu Gln Asp Val Val Asn Gln Asn Ala Gln Ala Leu Asn Thr
        35                  40                  45

Leu Val Lys Gln Leu Ser Ser Asn Phe Gly Ala Ile Ser Ser Val Leu
    50                  55                  60

Asn Asp Ile Leu Ser Arg Leu Asp Lys Val Glu Ala Glu
65                  70                  75

<210> SEQ ID NO 8
<211> LENGTH: 47
<212> TYPE: PRT
<213> ORGANISM: Coronavirus

<400> SEQUENCE: 8

Thr Ser Pro Asp Val Asp Phe Gly Asp Ile Ser Gly Ile Asn Ala Ser
1               5                   10                  15

Val Val Asn Ile Gln Lys Glu Ile Asp Arg Leu Asn Glu Val Ala Lys
            20                  25                  30

Asn Leu Asn Glu Ser Leu Ile Asp Leu Gln Glu Leu Gly Lys Tyr
        35                  40                  45

<210> SEQ ID NO 9
<211> LENGTH: 43
<212> TYPE: PRT
<213> ORGANISM: Filovirus

<400> SEQUENCE: 9

Asp Gly Leu Ile Cys Gly Leu Arg Gln Leu Ala Asn Glu Thr Thr Gln
1               5                   10                  15

Ala Leu Gln Leu Phe Leu Arg Ala Thr Thr Glu Leu Arg Thr Phe Ser
            20                  25                  30

Ile Leu Asn Arg Lys Ala Ile Asp Phe Leu Leu
        35                  40

<210> SEQ ID NO 10
<211> LENGTH: 24
<212> TYPE: PRT
<213> ORGANISM: Filovirus
```

```
<400> SEQUENCE: 10

Asp Trp Thr Lys Asn Ile Thr Asp Lys Ile Asp Gln Ile Ile His Asp
1               5                   10                  15

Phe Val Asp Lys Thr Leu Pro Asp
            20

<210> SEQ ID NO 11
<211> LENGTH: 57
<212> TYPE: PRT
<213> ORGANISM: Respiratory syncytial virus

<400> SEQUENCE: 11

Ser Gly Ile Ala Val Ser Lys Val Leu His Leu Glu Gly Glu Val Asn
1               5                   10                  15

Lys Ile Lys Asn Ala Leu Leu Ser Thr Asn Lys Ala Val Val Ser Leu
            20                  25                  30

Ser Asn Gly Val Ser Val Leu Thr Ser Lys Val Leu Asp Leu Lys Ser
        35                  40                  45

Tyr Ile Asn Asn Gln Leu Leu Pro Ile
    50                  55

<210> SEQ ID NO 12
<211> LENGTH: 54
<212> TYPE: PRT
<213> ORGANISM: Respiratory syncytial virus

<400> SEQUENCE: 12

Pro Ile Ile Asn Tyr Tyr Asp Pro Leu Val Phe Pro Ser Asp Glu Phe
1               5                   10                  15

Asp Ala Ser Ile Ser Gln Val Asn Glu Lys Ile Asn Gln Ser Leu Ala
            20                  25                  30

Phe Ile Arg Arg Ser Asp Glu Leu Leu His Asn Val Asn Thr Gly Lys
        35                  40                  45

Ser Thr Thr Asn Ile Met
    50

<210> SEQ ID NO 13
<211> LENGTH: 37
<212> TYPE: PRT
<213> ORGANISM: Human immunodeficiency virus-1

<400> SEQUENCE: 13

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 14
<211> LENGTH: 51
<212> TYPE: PRT
<213> ORGANISM: Human immunodeficiency virus-1

<400> SEQUENCE: 14

Arg Gln Leu Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30
```

```
Lys Gln Leu Gln Ala Arg Ile Leu Ala Val Glu Arg Tyr Leu Gln Asp
            35                  40                  45

Gln Gln Leu
    50

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple

<400> SEQUENCE: 15

Xaa Thr Trp Xaa Glu Trp Asp Xaa Glu Ile Asn Asn Tyr Thr Ser Leu
1               5                   10                  15

Ile His Ser Leu
            20

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 16

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Xaa Lys Asn Glu
            20                  25                  30

Xaa Glu Leu Leu Glu
        35
```

```
<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple

<400> SEQUENCE: 17

Xaa Thr Trp Xaa Xaa Trp Asp Arg Xaa Ile Asn Asn Tyr Thr Ser Leu
1               5                   10                  15

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (23)..(23)
<223> OTHER INFORMATION: Any amino acid which is linked by a hydrocarbon
      staple
<220> FEATURE:
<221> NAME/KEY: MOD_RES
<222> LOCATION: (27)..(27)
<223> OTHER INFORMATION: Any amino acid which is linked by a hydrocarbon
      staple

<400> SEQUENCE: 18

Xaa Thr Trp Xaa Glu Trp Asp Arg Glu Ile Asn Asn Tyr Thr Ser Leu
1               5                   10                  15

Ile His Ser Leu Ile Glu Xaa Ser Gln Asn Xaa Gln Glu Lys Asn Glu
                20                  25                  30

Gln Glu Leu Leu Glu
        35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple

<400> SEQUENCE: 19

Xaa Thr Trp Xaa Xaa Trp Asp Arg Xaa Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple
<220> FEATURE:
<221> NAME/KEY: MOD_RES
<222> LOCATION: (23)..(23)
<223> OTHER INFORMATION: Any amino acid which is linked by a hydrocarbon
      staple
<220> FEATURE:
<221> NAME/KEY: MOD_RES
<222> LOCATION: (27)..(27)
<223> OTHER INFORMATION: Any amino acid which is linked by a hydrocarbon
      staple

<400> SEQUENCE: 20

Xaa Thr Trp Xaa Xaa Trp Asp Arg Xaa Ile Asn Asn Tyr Thr Ser Leu
1               5                   10                  15

Ile His Ser Leu Ile Glu Xaa Ser Gln Asn Xaa Gln Glu Lys Asn Glu
            20                  25                  30

Gln Glu Leu Leu Glu
        35
```

```
<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 21

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Xaa Lys Asn Glu
            20                  25                  30

Xaa Glu Leu Leu Glu
        35

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 22

Xaa Thr Trp Xaa Xaa Trp Asp Arg Xaa Ile Asn Asn Tyr Thr Ser Leu
1               5                   10                  15
```

```
Ile His Ser Leu Ile Glu Glu Ser Gln Asn Gln Gln Xaa Lys Asn Glu
            20                  25                  30

Xaa Glu Leu Leu Glu
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (8)..(8)
<223> OTHER INFORMATION: Any amino acid which is linked by a hydrocarbon
      staple
<220> FEATURE:
<221> NAME/KEY: MOD_RES
<222> LOCATION: (12)..(12)
<223> OTHER INFORMATION: Any amino acid which is linked by a hydrocarbon
      staple
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 23

Xaa Thr Trp Xaa Glu Trp Asp Xaa Glu Ile Asn Xaa Tyr Thr Ser Leu
1               5                   10                  15

Ile His Ser Leu Ile Glu Glu Ser Gln Asn Gln Gln Xaa Lys Asn Glu
            20                  25                  30

Xaa Glu Leu Leu Glu
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (12)..(12)
<223> OTHER INFORMATION: Any amino acid which is linked by a hydrocarbon
      staple
<220> FEATURE:
<221> NAME/KEY: MOD_RES
<222> LOCATION: (16)..(16)
<223> OTHER INFORMATION: Any amino acid which is linked by a hydrocarbon
```

```
          staple
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 24

Xaa Thr Trp Xaa Glu Trp Asp Arg Glu Ile Asn Xaa Tyr Thr Ser Xaa
1               5                   10                  15

Ile His Ser Leu Ile Glu Glu Ser Gln Asn Gln Gln Xaa Lys Asn Glu
            20                  25                  30

Xaa Glu Leu Leu Glu
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (16)..(16)
<223> OTHER INFORMATION: Any amino acid which is linked by a hydrocarbon
      staple
<220> FEATURE:
<221> NAME/KEY: MOD_RES
<222> LOCATION: (20)..(20)
<223> OTHER INFORMATION: Any amino acid which is linked by a hydrocarbon
      staple
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 25

Xaa Thr Trp Xaa Glu Trp Asp Arg Glu Ile Asn Asn Tyr Thr Ser Xaa
1               5                   10                  15

Ile His Ser Xaa Ile Glu Glu Ser Gln Asn Gln Gln Xaa Lys Asn Glu
            20                  25                  30

Xaa Glu Leu Leu Glu
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple
<220> FEATURE:
<221> NAME/KEY: MOD_RES
<222> LOCATION: (16)..(16)
<223> OTHER INFORMATION: Any amino acid which is linked by a hydrocarbon
      staple
<220> FEATURE:
<221> NAME/KEY: MOD_RES
<222> LOCATION: (20)..(20)
<223> OTHER INFORMATION: Any amino acid which is linked by a hydrocarbon
      staple
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (33)..(33)
<223> OTHER INFORMATION: Any amino acid which is linked by a hydrocarbon
      staple

<400> SEQUENCE: 26

Xaa Thr Trp Xaa Xaa Trp Asp Arg Xaa Ile Asn Asn Tyr Thr Ser Xaa
1               5                   10                  15

Ile His Ser Xaa Ile Glu Glu Ser Gln Asn Gln Gln Xaa Lys Asn Glu
            20                  25                  30

Xaa Glu Leu Leu Glu
        35

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple

<400> SEQUENCE: 27

Tyr Thr Ser Xaa Ile His Ser Xaa Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid which is linked by a hydrocarbon
      staple
<220> FEATURE:
<221> NAME/KEY: MOD_RES
<222> LOCATION: (10)..(10)
<223> OTHER INFORMATION: Any amino acid which is linked by a hydrocarbon
      staple

<400> SEQUENCE: 28

Tyr Thr Ser Leu Ile Xaa Ser Leu Ile Xaa Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid which is linked by a hydrocarbon
      staple
<220> FEATURE:
<221> NAME/KEY: MOD_RES
<222> LOCATION: (15)..(15)
<223> OTHER INFORMATION: Any amino acid which is linked by a hydrocarbon
      staple

<400> SEQUENCE: 29

Tyr Thr Ser Leu Ile His Ser Leu Ile Glu Xaa Ser Gln Asn Xaa Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Any amino acid which is linked by a hydrocarbon
      staple
<220> FEATURE:
<221> NAME/KEY: MOD_RES
<222> LOCATION: (21)..(21)
<223> OTHER INFORMATION: Any amino acid which is linked by a hydrocarbon
      staple

```
<400> SEQUENCE: 30

Tyr Thr Ser Leu Ile His Ser Leu Ile Glu Glu Ser Gln Asn Gln Gln
1               5                   10                  15

Xaa Lys Asn Glu Xaa Glu Leu Leu Glu Leu Asp Lys Trp Ala Ser Leu
            20                  25                  30

Trp Asn Trp Phe
        35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Any amino acid which is linked by a hydrocarbon
      staple
<220> FEATURE:
<221> NAME/KEY: MOD_RES
<222> LOCATION: (22)..(22)
<223> OTHER INFORMATION: Any amino acid which is linked by a hydrocarbon
      staple

<400> SEQUENCE: 31

Tyr Thr Ser Leu Ile His Ser Leu Ile Glu Glu Ser Gln Asn Gln Gln
1               5                   10                  15

Glu Xaa Asn Glu Gln Xaa Leu Leu Glu Leu Asp Lys Trp Ala Ser Leu
            20                  25                  30

Trp Asn Trp Phe
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Any amino acid which is linked by a hydrocarbon
      staple
<220> FEATURE:
<221> NAME/KEY: MOD_RES
<222> LOCATION: (26)..(26)
<223> OTHER INFORMATION: Any amino acid which is linked by a hydrocarbon
      staple

<400> SEQUENCE: 32

Tyr Thr Ser Leu Ile His Ser Leu Ile Glu Glu Ser Gln Asn Gln Gln
1               5                   10                  15

Glu Lys Asn Glu Gln Xaa Leu Leu Glu Xaa Asp Lys Trp Ala Ser Leu
            20                  25                  30

Trp Asn Trp Phe
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
```

```
          polypeptide
<220> FEATURE:
<221> NAME/KEY: MOD_RES
<222> LOCATION: (28)..(28)
<223> OTHER INFORMATION: Any amino acid which is linked by a hydrocarbon
      staple
<220> FEATURE:
<221> NAME/KEY: MOD_RES
<222> LOCATION: (32)..(32)
<223> OTHER INFORMATION: Any amino acid which is linked by a hydrocarbon
      staple

<400> SEQUENCE: 33

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Xaa Trp Ala Ser Xaa
            20                  25                  30

Trp Asn Trp Phe
            35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid which is linked by a hydrocarbon
      staple
<220> FEATURE:
<221> NAME/KEY: MOD_RES
<222> LOCATION: (34)..(34)
<223> OTHER INFORMATION: Any amino acid which is linked by a hydrocarbon
      staple

<400> SEQUENCE: 34

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Xaa Ser Leu
            20                  25                  30

Trp Xaa Trp Phe
            35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid which is linked by a hydrocarbon
      staple
<220> FEATURE:
<221> NAME/KEY: MOD_RES
<222> LOCATION: (15)..(15)
<223> OTHER INFORMATION: Any amino acid which is linked by a hydrocarbon
      staple
<220> FEATURE:
<221> NAME/KEY: MOD_RES
<222> LOCATION: (22)..(22)
<223> OTHER INFORMATION: Any amino acid which is linked by a hydrocarbon
      staple
<220> FEATURE:
<221> NAME/KEY: MOD_RES
<222> LOCATION: (26)..(26)
```

```
<223> OTHER INFORMATION: Any amino acid which is linked by a hydrocarbon
      staple

<400> SEQUENCE: 35

Tyr Thr Ser Leu Ile His Ser Leu Ile Glu Xaa Ser Gln Asn Xaa Gln
1               5                   10                  15

Glu Lys Asn Glu Gln Xaa Leu Leu Glu Xaa Asp Lys Trp Ala Ser Leu
            20                  25                  30

Trp Asn Trp Phe
            35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple
<220> FEATURE:
<221> NAME/KEY: MOD_RES
<222> LOCATION: (30)..(30)
<223> OTHER INFORMATION: Any amino acid which is linked by a hydrocarbon
      staple
<220> FEATURE:
<221> NAME/KEY: MOD_RES
<222> LOCATION: (34)..(34)
<223> OTHER INFORMATION: Any amino acid which is linked by a hydrocarbon
      staple

<400> SEQUENCE: 36

Tyr Thr Ser Xaa Ile His Ser Xaa Ile Glu Glu Ser Gln Asn Gln Gln
1               5                   10                  15

Glu Lys Asn Glu Gln Glu Leu Leu Glu Leu Asp Lys Trp Xaa Ser Leu
            20                  25                  30

Trp Xaa Trp Phe
            35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Any amino acid which is linked by a hydrocarbon
      staple
<220> FEATURE:
<221> NAME/KEY: MOD_RES
<222> LOCATION: (21)..(21)
<223> OTHER INFORMATION: Any amino acid which is linked by a hydrocarbon
      staple
<220> FEATURE:
<221> NAME/KEY: MOD_RES
<222> LOCATION: (30)..(30)
<223> OTHER INFORMATION: Any amino acid which is linked by a hydrocarbon
      staple
<220> FEATURE:
<221> NAME/KEY: MOD_RES
```

```
<222> LOCATION: (34)..(34)
<223> OTHER INFORMATION: Any amino acid which is linked by a hydrocarbon
      staple

<400> SEQUENCE: 37

Tyr Thr Ser Leu Ile His Ser Leu Ile Glu Glu Ser Gln Asn Gln Gln
1               5                   10                  15

Xaa Lys Asn Glu Xaa Glu Leu Leu Glu Leu Asp Lys Trp Xaa Ser Leu
            20                  25                  30

Trp Xaa Trp Phe
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple
<220> FEATURE:
<221> NAME/KEY: MOD_RES
<222> LOCATION: (17)..(17)
<223> OTHER INFORMATION: Any amino acid which is linked by a hydrocarbon
      staple
<220> FEATURE:
<221> NAME/KEY: MOD_RES
<222> LOCATION: (21)..(21)
<223> OTHER INFORMATION: Any amino acid which is linked by a hydrocarbon
      staple

<400> SEQUENCE: 38

Tyr Thr Ser Xaa Ile His Ser Xaa Ile Glu Glu Ser Gln Asn Gln Gln
1               5                   10                  15

Xaa Lys Asn Glu Xaa Glu Leu Leu Glu Leu Asp Lys Trp Ala Ser Leu
            20                  25                  30

Trp Asn Trp Phe
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple
<220> FEATURE:
<221> NAME/KEY: MOD_RES
<222> LOCATION: (28)..(28)
<223> OTHER INFORMATION: Any amino acid which is linked by a hydrocarbon
      staple
<220> FEATURE:
```

```
<221> NAME/KEY: MOD_RES
<222> LOCATION: (32)..(32)
<223> OTHER INFORMATION: Any amino acid which is linked by a hydrocarbon
      staple

<400> SEQUENCE: 39

Tyr Thr Ser Xaa Ile His Ser Xaa Ile Glu Glu Ser Gln Asn Gln Gln
1               5                   10                  15

Glu Lys Asn Glu Gln Glu Leu Leu Glu Leu Asp Xaa Trp Ala Ser Xaa
            20                  25                  30

Trp Asn Trp Phe
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid which is linked by a hydrocarbon
      staple
<220> FEATURE:
<221> NAME/KEY: MOD_RES
<222> LOCATION: (15)..(15)
<223> OTHER INFORMATION: Any amino acid which is linked by a hydrocarbon
      staple
<220> FEATURE:
<221> NAME/KEY: MOD_RES
<222> LOCATION: (28)..(28)
<223> OTHER INFORMATION: Any amino acid which is linked by a hydrocarbon
      staple
<220> FEATURE:
<221> NAME/KEY: MOD_RES
<222> LOCATION: (32)..(32)
<223> OTHER INFORMATION: Any amino acid which is linked by a hydrocarbon
      staple

<400> SEQUENCE: 40

Tyr Thr Ser Leu Ile His Ser Leu Ile Glu Xaa Ser Gln Asn Xaa Gln
1               5                   10                  15

Glu Lys Asn Glu Gln Glu Leu Leu Glu Leu Asp Xaa Trp Ala Ser Xaa
            20                  25                  30

Trp Asn Trp Phe
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (8)..(8)
<223> OTHER INFORMATION: Any amino acid which is linked by a hydrocarbon
      staple
<220> FEATURE:
<221> NAME/KEY: MOD_RES
<222> LOCATION: (17)..(17)
<223> OTHER INFORMATION: Any amino acid which is linked by a hydrocarbon
      staple
```

```
<220> FEATURE:
<221> NAME/KEY: MOD_RES
<222> LOCATION: (21)..(21)
<223> OTHER INFORMATION: Any amino acid which is linked by a hydrocarbon
      staple
<220> FEATURE:
<221> NAME/KEY: MOD_RES
<222> LOCATION: (28)..(28)
<223> OTHER INFORMATION: Any amino acid which is linked by a hydrocarbon
      staple
<220> FEATURE:
<221> NAME/KEY: MOD_RES
<222> LOCATION: (32)..(32)
<223> OTHER INFORMATION: Any amino acid which is linked by a hydrocarbon
      staple

<400> SEQUENCE: 41

Tyr Thr Ser Xaa Ile His Ser Xaa Ile Glu Glu Ser Gln Asn Gln Gln
1               5                   10                  15

Xaa Lys Asn Glu Xaa Glu Leu Leu Glu Leu Asp Xaa Trp Ala Ser Xaa
            20                  25                  30

Trp Asn Trp Phe
            35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple
<220> FEATURE:
<221> NAME/KEY: MOD_RES
<222> LOCATION: (28)..(28)
<223> OTHER INFORMATION: Any amino acid which is linked by a hydrocarbon
      staple
<220> FEATURE:
<221> NAME/KEY: MOD_RES
<222> LOCATION: (32)..(32)
<223> OTHER INFORMATION: Any amino acid which is linked by a hydrocarbon
      staple

<400> SEQUENCE: 42

Xaa Thr Trp Xaa Xaa Trp Asp Arg Xaa Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
            35

<210> SEQ ID NO 43
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (5)..(5)
<223> OTHER INFORMATION: Any amino acid which is linked by a hydrocarbon
      staple
<220> FEATURE:
<221> NAME/KEY: MOD_RES
<222> LOCATION: (9)..(9)
<223> OTHER INFORMATION: Any amino acid which is linked by a hydrocarbon
      staple
<220> FEATURE:
<221> NAME/KEY: MOD_RES
<222> LOCATION: (27)..(27)
<223> OTHER INFORMATION: Any amino acid which is linked by a hydrocarbon
      staple
<220> FEATURE:
<221> NAME/KEY: MOD_RES
<222> LOCATION: (31)..(31)
<223> OTHER INFORMATION: Any amino acid which is linked by a hydrocarbon
      staple

<400> SEQUENCE: 43

Xaa Thr Trp Xaa Xaa Trp Asp Arg Xaa Ile Asn Asn Tyr Thr Ser Leu
1               5                   10                  15

Ile His Ser Leu Ile Glu Glu Ser Gln Asn Xaa Gln Glu Lys Xaa Glu
            20                  25                  30

Gln Glu Leu Leu Glu
        35

<210> SEQ ID NO 44
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(23)
```

```
<223> OTHER INFORMATION: Any amino acid
<220> FEATURE:
<221> NAME/KEY: MOD_RES
<222> LOCATION: (25)..(26)
<223> OTHER INFORMATION: Any amino acid
<220> FEATURE:
<221> NAME/KEY: MOD_RES
<222> LOCATION: (28)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (35)..(37)
<223> OTHER INFORMATION: Any amino acid

<400> SEQUENCE: 44

Xaa Xaa Trp Xaa Xaa Trp Xaa Xaa Xaa Ile Xaa Xaa Tyr Xaa Xaa Xaa
1               5                   10                  15

Ile Xaa Xaa Leu Xaa Xaa Xaa Ser Xaa Xaa Gln Xaa Xaa Xaa Asn Xaa
            20                  25                  30

Xaa Glu Xaa Xaa Xaa Leu
        35

<210> SEQ ID NO 45
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (22)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(34)
<223> OTHER INFORMATION: Any amino acid
<220> FEATURE:
<221> NAME/KEY: MOD_RES
```

```
<222> LOCATION: (36)..(36)
<223> OTHER INFORMATION: Any amino acid

<400> SEQUENCE: 45

Xaa Thr Trp Xaa Xaa Trp Asp Arg Xaa Ile Xaa Xaa Tyr Xaa Xaa Xaa
1               5                   10                  15

Ile Xaa Xaa Leu Ile Xaa Xaa Xaa Gln Xaa Xaa Gln Glu Lys Xaa Glu
            20                  25                  30

Xaa Xaa Leu Xaa Glu Leu
        35

<210> SEQ ID NO 46
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Any amino acid which is linked by a hydrocarbon
      staple
<220> FEATURE:
<221> NAME/KEY: MOD_RES
<222> LOCATION: (5)..(5)
<223> OTHER INFORMATION: Met or Nle
<220> FEATURE:
<221> NAME/KEY: MOD_RES
<222> LOCATION: (9)..(9)
<223> OTHER INFORMATION: Any amino acid which is linked by a hydrocarbon
      staple

<400> SEQUENCE: 47

Xaa Thr Trp Xaa Xaa Glu Trp Asp Xaa Arg Glu Ile Asn Asn Tyr Thr
1               5                   10                  15

Ser Leu Ile His Ser Leu
            20

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: Met or Nle
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (29)..(29)
<223> OTHER INFORMATION: Any amino acid which is linked by a hydrocarbon
      staple
<220> FEATURE:
<221> NAME/KEY: MOD_RES
<222> LOCATION: (34)..(34)
<223> OTHER INFORMATION: Any amino acid which is linked by a hydrocarbon
      staple

<400> SEQUENCE: 48

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Xaa Glu Lys Asn
            20                  25                  30

Glu Xaa Gln Glu Leu Leu Glu
        35

<210> SEQ ID NO 49
<211> LENGTH: 856
<212> TYPE: PRT
<213> ORGANISM: Human immunodeficiency virus-1

<400> SEQUENCE: 49

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
```

-continued

```
            225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
                275                 280                 285

Asn Thr Ser Val Glu Ile Asn Cys Thr Arg Pro Asn Asn Asn Thr Arg
            290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655
```

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
        690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
                740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
        770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
        850                 855

<210> SEQ ID NO 50
<211> LENGTH: 843
<212> TYPE: PRT
<213> ORGANISM: Human immunodeficiency virus-1

<400> SEQUENCE: 50

Met Arg Ala Thr Glu Ile Arg Lys Asn Tyr Gln His Leu Trp Lys Gly
1               5                   10                  15

Gly Thr Leu Leu Leu Gly Met Leu Met Ile Cys Ser Ala Ala Glu Gln
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Lys Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Thr Ser Ser Ser Trp
        130                 135                 140

Glu Thr Met Glu Lys Gly Glu Ile Lys Asn Cys Ser Phe Asn Ile Thr
145                 150                 155                 160

Thr Ser Ile Arg Asp Lys Val Gln Lys Glu Tyr Ala Leu Phe Tyr Asn

```
            165                 170                 175
Leu Asp Val Val Pro Ile Asp Asn Ala Ser Tyr Arg Leu Ile Ser Cys
            180                 185                 190

Asn Thr Ser Val Ile Thr Gln Ala Cys Pro Lys Val Ser Phe Glu Pro
            195                 200                 205

Ile Pro Ile His Tyr Cys Ala Pro Ala Gly Phe Ala Ile Leu Lys Cys
            210                 215                 220

Asn Asp Lys Lys Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
            245                 250                 255

Leu Asn Gly Ser Leu Ala Glu Glu Ile Val Ile Arg Ser Glu Asn
            260                 265                 270

Phe Thr Asn Asn Ala Lys Thr Ile Ile Val Gln Leu Asn Glu Ser Val
            275                 280                 285

Val Ile Asn Cys Thr Arg Pro Asn Asn Asn Thr Arg Lys Ser Ile Asn
            290                 295                 300

Ile Gly Pro Gly Arg Ala Leu Tyr Thr Thr Gly Glu Ile Ile Gly Asp
305                 310                 315                 320

Ile Arg Gln Ala His Cys Asn Leu Ser Lys Thr Gln Trp Glu Asn Thr
            325                 330                 335

Leu Glu Gln Ile Ala Ile Lys Leu Lys Glu Gln Phe Gly Asn Asn Lys
            340                 345                 350

Thr Ile Ile Phe Asn Pro Ser Ser Gly Gly Asp Pro Glu Ile Val Thr
            355                 360                 365

His Ser Phe Asn Cys Gly Gly Glu Phe Phe Tyr Cys Asn Ser Thr Gln
            370                 375                 380

Leu Phe Thr Trp Asn Asp Thr Arg Lys Leu Asn Asn Thr Gly Arg Asn
385                 390                 395                 400

Ile Thr Leu Pro Cys Arg Ile Lys Gln Ile Ile Asn Met Trp Gln Glu
            405                 410                 415

Val Gly Lys Ala Met Tyr Ala Pro Pro Ile Arg Gly Gln Ile Arg Cys
            420                 425                 430

Ser Ser Asn Ile Thr Gly Leu Leu Leu Thr Arg Asp Gly Gly Lys Asp
            435                 440                 445

Thr Asn Gly Thr Glu Ile Phe Arg Pro Gly Gly Gly Asp Met Arg Asp
450                 455                 460

Asn Trp Arg Ser Glu Leu Tyr Lys Tyr Lys Val Val Lys Ile Glu Pro
465                 470                 475                 480

Leu Gly Val Ala Pro Thr Lys Ala Lys Arg Arg Val Val Gln Arg Glu
            485                 490                 495

Lys Arg Ala Val Gly Leu Gly Ala Leu Phe Leu Gly Phe Leu Gly Ala
            500                 505                 510

Ala Gly Ser Thr Met Gly Ala Ala Ser Ile Thr Leu Thr Val Gln Ala
            515                 520                 525

Arg Gln Leu Leu Ser Gly Ile Val Gln Gln Asn Asn Leu Leu Arg
            530                 535                 540

Ala Ile Glu Ala Gln Gln His Leu Leu Gln Leu Thr Val Trp Gly Ile
545                 550                 555                 560

Lys Gln Leu Gln Ala Arg Val Leu Ala Val Glu Arg Tyr Leu Arg Asp
            565                 570                 575

Gln Gln Leu Leu Gly Ile Trp Gly Cys Ser Gly Lys Leu Ile Cys Thr
            580                 585                 590
```

-continued

```
Thr Thr Val Pro Trp Asn Thr Ser Trp Ser Asn Lys Ser Leu Asn Glu
        595                 600                 605

Ile Trp Asp Asn Met Thr Trp Met Lys Trp Glu Arg Glu Ile Asp Asn
610                 615                 620

Tyr Thr His Ile Ile Tyr Ser Leu Ile Glu Gln Ser Gln Asn Gln Gln
625                 630                 635                 640

Glu Lys Asn Glu Gln Glu Leu Leu Ala Leu Asp Lys Trp Ala Ser Leu
                645                 650                 655

Trp Asn Trp Phe Asp Ile Thr Lys Trp Leu Trp Tyr Ile Lys Ile Phe
                660                 665                 670

Ile Met Ile Val Gly Gly Leu Ile Gly Leu Arg Ile Val Phe Val Val
            675                 680                 685

Leu Ser Ile Val Asn Arg Val Arg Gln Gly Tyr Ser Pro Leu Ser Phe
            690                 695                 700

Gln Thr His Leu Pro Ala Gln Arg Gly Pro Asp Arg Pro Asp Gly Ile
705                 710                 715                 720

Glu Glu Glu Gly Gly Glu Arg Asp Arg Asp Arg Ser Gly Pro Leu Val
                725                 730                 735

Asp Gly Phe Leu Ala Ile Ile Trp Val Asp Leu Arg Ser Leu Cys Leu
                740                 745                 750

Phe Ser Tyr His Arg Leu Arg Asp Leu Leu Leu Ile Val Thr Arg Ile
            755                 760                 765

Val Glu Leu Leu Gly Arg Arg Gly Trp Gly Val Leu Lys Tyr Trp Trp
            770                 775                 780

Asn Leu Leu Gln Tyr Trp Ile Gln Glu Leu Lys Asn Ser Ala Val Ser
785                 790                 795                 800

Leu Leu Asn Ala Thr Ala Ile Ala Val Ala Glu Gly Thr Asp Arg Val
                805                 810                 815

Ile Glu Ile Leu Gln Arg Ala Phe Arg Ala Val Leu His Ile Pro Val
                820                 825                 830

Arg Ile Arg Gln Gly Leu Glu Arg Ala Leu Leu
            835                 840

<210> SEQ ID NO 51
<211> LENGTH: 65
<212> TYPE: PRT
<213> ORGANISM: Human parainfluenza virus

<400> SEQUENCE: 51

Ala Leu Gly Val Ala Thr Ser Ala Gln Ile Thr Ala Ala Val Ala Leu
1               5                   10                  15

Val Glu Ala Lys Gln Ala Arg Ser Asp Ile Glu Lys Leu Lys Glu Ala
                20                  25                  30

Ile Arg Asp Thr Asn Lys Ala Val Gln Ser Val Gln Ser Ser Ile Gly
            35                  40                  45

Asn Leu Ile Val Ala Ile Lys Ser Val Gln Asp Tyr Val Asn Lys Glu
        50                  55                  60

Ile
65

<210> SEQ ID NO 52
<211> LENGTH: 50
<212> TYPE: PRT
<213> ORGANISM: Human T-lymphotropic virus 1

<400> SEQUENCE: 52
```

Met Ser Leu Ala Ser Gly Lys Ser Leu Leu His Glu Val Asp Lys Asp
1               5                   10                  15

Ile Ser Gln Leu Thr Gln Ala Ile Val Lys Asn His Lys Asn Leu Leu
            20                  25                  30

Lys Ile Ala Gln Tyr Ala Ala Gln Asn Arg Arg Gly Leu Asp Leu Leu
        35                  40                  45

Phe Trp
    50

<210> SEQ ID NO 53
<211> LENGTH: 42
<212> TYPE: PRT
<213> ORGANISM: Marburg virus

<400> SEQUENCE: 53

Asn Asn Leu Val Cys Arg Leu Arg Arg Leu Ala Asn Gln Thr Ala Lys
1               5                   10                  15

Ser Leu Glu Leu Leu Leu Arg Val Thr Thr Glu Glu Arg Thr Phe Ser
            20                  25                  30

Leu Ile Asn Arg His Ala Ile Asp Phe Leu
        35                  40

<210> SEQ ID NO 54
<211> LENGTH: 43
<212> TYPE: PRT
<213> ORGANISM: Human immunodeficiency virus-1

<400> SEQUENCE: 54

Trp Asn Asn Met Thr Trp Met Glu Trp Glu Lys Glu Ile Asp Asn Tyr
1               5                   10                  15

Thr Ser Ile Ile Tyr Thr Leu Leu Glu Thr Ser Gln Asn Gln Gln Glu
            20                  25                  30

Lys Asn Glu Gln Glu Leu Leu Glu Leu Asp Lys
        35                  40

<210> SEQ ID NO 55
<211> LENGTH: 56
<212> TYPE: PRT
<213> ORGANISM: Human parainfluenza virus

<400> SEQUENCE: 55

Tyr Thr Pro Asn Asp Ile Thr Leu Asn Asn Ser Val Ala Leu Asp Pro
1               5                   10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
    50                  55

<210> SEQ ID NO 56
<211> LENGTH: 30
<212> TYPE: PRT
<213> ORGANISM: Human T-lymphotropic virus 1

<400> SEQUENCE: 56

Cys Cys Phe Leu Asn Ile Thr Asn Ser His Val Ser Ile Leu Gln Glu
1               5                   10                  15

Arg Pro Pro Leu Glu Asn Arg Val Leu Thr Gly Trp Gly Leu

```
                    20                  25                  30

<210> SEQ ID NO 57
<211> LENGTH: 20
<212> TYPE: PRT
<213> ORGANISM: Marburg virus

<400> SEQUENCE: 57

Ile Glu Asp Leu Ser Arg Asn Ile Ser Glu Gln Ile Asp Gln Ile Lys
1               5                   10                  15

Lys Asp Glu Gln
            20

<210> SEQ ID NO 58
<211> LENGTH: 36
<212> TYPE: PRT
<213> ORGANISM: Human immunodeficiency virus-1

<400> SEQUENCE: 58

Tyr Thr His Ile Ile Tyr Ser Leu Ile Glu Gln Ser Gln Asn Gln Gln
1               5                   10                  15

Glu Lys Asn Glu Gln Glu Leu Leu Ala Leu Asp Lys Trp Ala Ser Leu
            20                  25                  30

Trp Asn Trp Phe
        35

<210> SEQ ID NO 59
<211> LENGTH: 36
<212> TYPE: PRT
<213> ORGANISM: Human immunodeficiency virus-1

<400> SEQUENCE: 59

Met Thr Met Lys Trp Glu Arg Glu Ile Asp Asn Tyr Thr His Ile Ile
1               5                   10                  15

Tyr Ser Leu Ile Glu Gln Ser Gln Asn Gln Gln Glu Lys Asn Glu Gln
            20                  25                  30

Glu Leu Leu Ala
        35

<210> SEQ ID NO 60
<211> LENGTH: 20
<212> TYPE: PRT
<213> ORGANISM: Human immunodeficiency virus-1
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 60

Xaa Thr Trp Xaa Glu Trp Asp Arg Glu Ile Asn Asn Tyr Thr Ser Leu
1               5                   10                  15

Ile His Ser Leu
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                         peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: S5 amino acid
<220> FEATURE:
<221> NAME/KEY: MOD_RES
<222> LOCATION: (8)..(8)
<223> OTHER INFORMATION: S5 amino acid

<400> SEQUENCE: 61

Xaa Thr Trp Xaa Glu Trp Asp Xaa Glu Ile Asn Asn Tyr Thr Ser Leu
1               5                   10                  15

Ile His Ser Leu
            20

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Trp Gln Glu Trp Glu Arg Val Asp Phe Leu Glu Glu Asn Ile Thr Ala
1               5                   10                  15

Leu Leu Glu Glu Ala Gln Ile Gln Gln Glu Lys
            20                  25

<210> SEQ ID NO 63
<211> LENGTH: 6
<212> TYPE: PRT
<213> ORGANISM: Simian immunodeficiency virus

<400> SEQUENCE: 63

Gln Gln Glu Lys Asn Glu
1               5

<210> SEQ ID NO 64
<211> LENGTH: 8
<212> TYPE: PRT
<213> ORGANISM: Human immunodeficiency virus-1

<400> SEQUENCE: 64

Leu Asp Lys Trp Ala Ser Leu Trp
1               5

<210> SEQ ID NO 65
<211> LENGTH: 5
<212> TYPE: PRT
<213> ORGANISM: Simian immunodeficiency virus

<400> SEQUENCE: 65

Trp Gln Glu Trp Glu
1               5

<210> SEQ ID NO 66
<211> LENGTH: 38
<212> TYPE: PRT
<213> ORGANISM: Human immunodeficiency virus-1

<400> SEQUENCE: 66
```

```
Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu
            35

<210> SEQ ID NO 67
<211> LENGTH: 48
<212> TYPE: PRT
<213> ORGANISM: Human immunodeficiency virus-1
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 67

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Ser Leu Trp Asn Trp Phe
            35                  40                  45

<210> SEQ ID NO 68
<211> LENGTH: 37
<212> TYPE: PRT
<213> ORGANISM: Human immunodeficiency virus-1
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 68

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu
            35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (28)..(28)
```

```
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 69

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: S5 amino acid
<220> FEATURE:
<221> NAME/KEY: MOD_RES
<222> LOCATION: (8)..(8)
<223> OTHER INFORMATION: S5 amino acid

<400> SEQUENCE: 70

Xaa Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (22)..(22)
<223> OTHER INFORMATION: S5 amino acid
<220> FEATURE:
<221> NAME/KEY: MOD_RES
<222> LOCATION: (26)..(26)
<223> OTHER INFORMATION: S5 amino acid

<400> SEQUENCE: 71

Xaa Thr Trp Xaa Glu Trp Asp Arg Glu Ile Asn Asn Tyr Thr Ser Leu
1               5                   10                  15
```

-continued

Ile His Ser Leu Ile Xaa Glu Ser Gln Xaa Gln Gln Glu Lys Asn Glu
            20                  25                  30

Gln Glu Leu Leu Glu
        35

<210> SEQ ID NO 72
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: S5 amino acid
<220> FEATURE:
<221> NAME/KEY: MOD_RES
<222> LOCATION: (7)..(7)
<223> OTHER INFORMATION: S5 amino acid

<400> SEQUENCE: 72

Tyr Thr Xaa Leu Ile His Xaa Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 73
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: S5 amino acid
<220> FEATURE:
<221> NAME/KEY: MOD_RES
<222> LOCATION: (20)..(20)
<223> OTHER INFORMATION: S5 amino acid

<400> SEQUENCE: 73

Tyr Thr Ser Leu Ile His Ser Leu Ile Glu Glu Ser Gln Asn Gln Xaa
1               5                   10                  15

Glu Lys Asn Xaa Gln Glu Leu Leu Glu Leu Asp Lys Trp Ala Ser Leu
            20                  25                  30

Trp Asn Trp Phe
        35

<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

```
<400> SEQUENCE: 74

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Xaa Lys Trp Ala Xaa Leu
            20                  25                  30

Trp Asn Trp Phe
        35

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: S5 amino acid
<220> FEATURE:
<221> NAME/KEY: MOD_RES
<222> LOCATION: (33)..(33)
<223> OTHER INFORMATION: S5 amino acid

<400> SEQUENCE: 75

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Xaa Ala Ser Leu
            20                  25                  30

Xaa Asn Trp Phe
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: S5 amino acid
<220> FEATURE:
<221> NAME/KEY: MOD_RES
<222> LOCATION: (9)..(9)
<223> OTHER INFORMATION: S5 amino acid

<400> SEQUENCE: 76

Tyr Thr Ser Leu Xaa His Ser Leu Xaa Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: S5 amino acid
```

```
<220> FEATURE:
<221> NAME/KEY: MOD_RES
<222> LOCATION: (14)..(14)
<223> OTHER INFORMATION: S5 amino acid

<400> SEQUENCE: 77

Tyr Thr Ser Leu Ile His Ser Leu Ile Xaa Glu Ser Gln Xaa Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 78
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: S5 amino acid
<220> FEATURE:
<221> NAME/KEY: MOD_RES
<222> LOCATION: (21)..(21)
<223> OTHER INFORMATION: S5 amino acid

<400> SEQUENCE: 78

Tyr Thr Ser Leu Ile His Ser Leu Ile Glu Glu Ser Gln Asn Gln Gln
1               5                   10                  15

Xaa Lys Asn Glu Xaa Glu Leu Leu Glu Leu Asp Lys Trp Ala Ser Leu
            20                  25                  30

Trp Asn Trp Phe
        35

<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: S5 amino acid
<220> FEATURE:
<221> NAME/KEY: MOD_RES
<222> LOCATION: (25)..(25)
<223> OTHER INFORMATION: S5 amino acid

<400> SEQUENCE: 79

Tyr Thr Ser Leu Ile His Ser Leu Ile Glu Glu Ser Gln Asn Gln Gln
1               5                   10                  15

Glu Lys Asn Glu Xaa Glu Leu Leu Xaa Leu Asp Lys Trp Ala Ser Leu
            20                  25                  30

Trp Asn Trp Phe
        35

<210> SEQ ID NO 80
<211> LENGTH: 48
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 80

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 81

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: S5 amino acid
<220> FEATURE:
<221> NAME/KEY: MOD_RES
<222> LOCATION: (8)..(8)
<223> OTHER INFORMATION: S5 amino acid
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid
```

<400> SEQUENCE: 82

Xaa Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 83
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: S5 amino acid
<220> FEATURE:
<221> NAME/KEY: MOD_RES
<222> LOCATION: (11)..(11)
<223> OTHER INFORMATION: S5 amino acid
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 83

Xaa Thr Trp Xaa Glu Trp Xaa Arg Glu Ile Xaa Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (11)..(11)
<223> OTHER INFORMATION: S5 amino acid
<220> FEATURE:
<221> NAME/KEY: MOD_RES
<222> LOCATION: (15)..(15)
<223> OTHER INFORMATION: S5 amino acid

```
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 84

Xaa Thr Trp Xaa Glu Trp Asp Arg Glu Ile Xaa Asn Tyr Thr Xaa Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (15)..(15)
<223> OTHER INFORMATION: S5 amino acid
<220> FEATURE:
<221> NAME/KEY: MOD_RES
<222> LOCATION: (19)..(19)
<223> OTHER INFORMATION: S5 amino acid
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 85

Xaa Thr Trp Xaa Glu Trp Asp Arg Glu Ile Asn Asn Tyr Thr Xaa Leu
1               5                   10                  15

Ile His Xaa Leu Ile Glu Glu Ser Gln Asn Gln Xaa Glu Lys Asn Xaa
            20                  25                  30

Gln Glu Leu Leu Glu
        35

<210> SEQ ID NO 86
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (4)..(4)
<223> OTHER INFORMATION: S5 amino acid
<220> FEATURE:
<221> NAME/KEY: MOD_RES
<222> LOCATION: (8)..(8)
<223> OTHER INFORMATION: S5 amino acid
<220> FEATURE:
<221> NAME/KEY: MOD_RES
<222> LOCATION: (22)..(22)
<223> OTHER INFORMATION: S5 amino acid
<220> FEATURE:
<221> NAME/KEY: MOD_RES
<222> LOCATION: (26)..(26)
<223> OTHER INFORMATION: S5 amino acid

<400> SEQUENCE: 86

Xaa Thr Trp Xaa Glu Trp Asp Xaa Glu Ile Asn Asn Tyr Thr Ser Leu
1               5                   10                  15

Ile His Ser Leu Ile Xaa Glu Ser Gln Xaa Gln Gln Glu Lys Asn Glu
            20                  25                  30

Gln Glu Leu Leu Glu
        35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: S5 amino acid
<220> FEATURE:
<221> NAME/KEY: MOD_RES
<222> LOCATION: (8)..(8)
<223> OTHER INFORMATION: S5 amino acid
<220> FEATURE:
<221> NAME/KEY: MOD_RES
<222> LOCATION: (15)..(15)
<223> OTHER INFORMATION: S5 amino acid
<220> FEATURE:
<221> NAME/KEY: MOD_RES
<222> LOCATION: (19)..(19)
<223> OTHER INFORMATION: S5 amino acid
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 87

Xaa Thr Trp Xaa Glu Trp Asp Xaa Glu Ile Asn Asn Tyr Thr Xaa Leu
1               5                   10                  15

Ile His Xaa Leu Ile Glu Glu Ser Gln Asn Gln Xaa Glu Lys Asn Xaa
            20                  25                  30

Gln Glu Leu Leu Glu
        35
```

```
<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: S5 amino acid
<220> FEATURE:
<221> NAME/KEY: MOD_RES
<222> LOCATION: (7)..(7)
<223> OTHER INFORMATION: S5 amino acid
<220> FEATURE:
<221> NAME/KEY: MOD_RES
<222> LOCATION: (29)..(29)
<223> OTHER INFORMATION: S5 amino acid
<220> FEATURE:
<221> NAME/KEY: MOD_RES
<222> LOCATION: (33)..(33)
<223> OTHER INFORMATION: S5 amino acid

<400> SEQUENCE: 88

Tyr Thr Xaa Leu Ile His Xaa Leu Ile Glu Glu Ser Gln Asn Gln Gln
1               5                   10                  15

Glu Lys Asn Glu Gln Glu Leu Leu Glu Leu Asp Lys Xaa Ala Ser Leu
            20                  25                  30

Xaa Asn Trp Phe
        35

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: S5 amino acid
<220> FEATURE:
<221> NAME/KEY: MOD_RES
<222> LOCATION: (7)..(7)
<223> OTHER INFORMATION: S5 amino acid
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

<400> SEQUENCE: 89

Tyr Thr Xaa Leu Ile His Xaa Leu Ile Glu Glu Ser Gln Asn Gln Gln
1               5                   10                  15

Glu Lys Asn Glu Gln Glu Leu Leu Glu Leu Xaa Lys Trp Ala Xaa Leu
            20                  25                  30

Trp Asn Trp Phe
        35

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (16)..(16)
<223> OTHER INFORMATION: S5 amino acid
<220> FEATURE:
<221> NAME/KEY: MOD_RES
<222> LOCATION: (20)..(20)
<223> OTHER INFORMATION: S5 amino acid
<220> FEATURE:
<221> NAME/KEY: MOD_RES
<222> LOCATION: (29)..(29)
<223> OTHER INFORMATION: S5 amino acid
<220> FEATURE:
<221> NAME/KEY: MOD_RES
<222> LOCATION: (33)..(33)
<223> OTHER INFORMATION: S5 amino acid

<400> SEQUENCE: 90

Tyr Thr Ser Leu Ile His Ser Leu Ile Glu Glu Ser Gln Asn Gln Xaa
1               5                   10                  15

Glu Lys Asn Xaa Gln Glu Leu Leu Glu Leu Asp Lys Xaa Ala Ser Leu
            20                  25                  30

Xaa Asn Trp Phe
        35

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: S5 amino acid
<220> FEATURE:
<221> NAME/KEY: MOD_RES
<222> LOCATION: (7)..(7)
<223> OTHER INFORMATION: S5 amino acid
<220> FEATURE:
<221> NAME/KEY: MOD_RES
<222> LOCATION: (16)..(16)
<223> OTHER INFORMATION: S5 amino acid
<220> FEATURE:
<221> NAME/KEY: MOD_RES
<222> LOCATION: (20)..(20)
<223> OTHER INFORMATION: S5 amino acid

<400> SEQUENCE: 91

Tyr Thr Xaa Leu Ile His Xaa Leu Ile Glu Glu Ser Gln Asn Gln Xaa
1               5                   10                  15

Glu Lys Asn Xaa Gln Glu Leu Leu Glu Leu Asp Lys Trp Ala Ser Leu
            20                  25                  30

Trp Asn Trp Phe
        35

<210> SEQ ID NO 92
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: S5 amino acid
```

```
<220> FEATURE:
<221> NAME/KEY: MOD_RES
<222> LOCATION: (14)..(14)
<223> OTHER INFORMATION: S5 amino acid
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

<400> SEQUENCE: 92

Tyr Thr Ser Leu Ile His Ser Leu Ile Xaa Glu Ser Gln Xaa Gln Gln
1               5                   10                  15

Glu Lys Asn Glu Gln Glu Leu Leu Glu Leu Xaa Lys Trp Ala Xaa Leu
            20                  25                  30

Trp Asn Trp Phe
        35

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: S5 amino acid
<220> FEATURE:
<221> NAME/KEY: MOD_RES
<222> LOCATION: (14)..(14)
<223> OTHER INFORMATION: S5 amino acid
<220> FEATURE:
<221> NAME/KEY: MOD_RES
<222> LOCATION: (21)..(21)
<223> OTHER INFORMATION: S5 amino acid
<220> FEATURE:
<221> NAME/KEY: MOD_RES
<222> LOCATION: (25)..(25)
<223> OTHER INFORMATION: S5 amino acid

<400> SEQUENCE: 93

Tyr Thr Ser Leu Ile His Ser Leu Ile Xaa Glu Ser Gln Xaa Gln Gln
1               5                   10                  15

Glu Lys Asn Glu Xaa Glu Leu Leu Xaa Leu Asp Lys Trp Ala Ser Leu
            20                  25                  30

Trp Asn Trp Phe
        35

<210> SEQ ID NO 94
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: S5 amino acid
<220> FEATURE:
<221> NAME/KEY: MOD_RES
<222> LOCATION: (7)..(7)
<223> OTHER INFORMATION: S5 amino acid
```

```
<220> FEATURE:
<221> NAME/KEY: MOD_RES
<222> LOCATION: (16)..(16)
<223> OTHER INFORMATION: S5 amino acid
<220> FEATURE:
<221> NAME/KEY: MOD_RES
<222> LOCATION: (20)..(20)
<223> OTHER INFORMATION: S5 amino acid
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

<400> SEQUENCE: 94

Tyr Thr Xaa Leu Ile His Xaa Leu Ile Glu Glu Ser Gln Asn Gln Xaa
1               5                   10                  15

Glu Lys Asn Xaa Gln Glu Leu Leu Glu Leu Xaa Lys Trp Ala Xaa Leu
            20                  25                  30

Trp Asn Trp Phe
        35

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: S5 amino acid
<220> FEATURE:
<221> NAME/KEY: MOD_RES
<222> LOCATION: (9)..(9)
<223> OTHER INFORMATION: S5 amino acid

<400> SEQUENCE: 95

Xaa Thr Trp Xaa Xaa Trp Asp Arg Xaa Ile Asn Asn Tyr Thr Ser Leu
1               5                   10                  15

Ile His Ser Leu Ile Glu Glu Ser Gln Asn Gln Glu Lys Asn Glu
            20                  25                  30

Gln Glu Leu Leu Glu
        35

<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
```

```
-continued

<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

<400> SEQUENCE: 96

Xaa Thr Trp Xaa Glu Trp Asp Arg Glu Ile Asn Asn Tyr Thr Ser Leu
 1               5                  10                  15

Ile His Ser Leu Ile Glu Glu Ser Gln Asn Xaa Gln Glu Lys Xaa Glu
            20                  25                  30

Gln Glu Leu Leu Glu
        35

<210> SEQ ID NO 97
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: S5 amino acid
<220> FEATURE:
<221> NAME/KEY: MOD_RES
<222> LOCATION: (9)..(9)
<223> OTHER INFORMATION: S5 amino acid
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 97

Xaa Thr Trp Xaa Xaa Trp Asp Arg Xaa Ile Asn Asn Tyr Thr Ser Leu
 1               5                  10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: S5 amino acid
<220> FEATURE:
<221> NAME/KEY: MOD_RES
<222> LOCATION: (9)..(9)
<223> OTHER INFORMATION: S5 amino acid
<220> FEATURE:
<221> NAME/KEY: MOD_RES
<222> LOCATION: (27)..(27)
<223> OTHER INFORMATION: S5 amino acid
<220> FEATURE:
<221> NAME/KEY: MOD_RES
<222> LOCATION: (31)..(31)
<223> OTHER INFORMATION: S5 amino acid

<400> SEQUENCE: 98

Xaa Thr Trp Xaa Xaa Trp Asp Arg Xaa Ile Asn Asn Tyr Thr Ser Leu
1               5                   10                  15

Ile His Ser Leu Ile Glu Glu Ser Gln Asn Xaa Gln Glu Lys Xaa Glu
            20                  25                  30

Gln Glu Leu Leu Glu
        35

<210> SEQ ID NO 99
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 99

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 100
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (28)..(28)
<223> OTHER INFORMATION: S5 amino acid
<220> FEATURE:
<221> NAME/KEY: MOD_RES
<222> LOCATION: (32)..(32)
<223> OTHER INFORMATION: S5 amino acid

<400> SEQUENCE: 100

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Xaa Glu Lys Asn Xaa
                20                  25                  30

Gln Glu Leu Leu Glu
                35
```